(12) United States Patent
Frache

(10) Patent No.: US 11,701,478 B2
(45) Date of Patent: Jul. 18, 2023

(54) METHOD FOR COATING MICROSTRUCTURED COMPONENTS

(71) Applicant: BOEHRINGER INGELHEIM INTERNATIONAL GMBH, Ingelheim am Rhein (DE)

(72) Inventor: Daniel Frache, Gau-Odernheim (DE)

(73) Assignee: BOEHRINGER INGELHEIM INTERNATIONAL GMBH, Ingelheim am Rhein (DE)

(*) Notice: Subject to any disclaimer, the term of this patent is extended or adjusted under 35 U.S.C. 154(b) by 1145 days.

(21) Appl. No.: 15/765,889

(22) PCT Filed: Oct. 6, 2016

(86) PCT No.: PCT/EP2016/073929
§ 371 (c)(1),
(2) Date: Apr. 4, 2018

(87) PCT Pub. No.: WO2017/060386
PCT Pub. Date: Apr. 13, 2017

(65) Prior Publication Data
US 2018/0296775 A1    Oct. 18, 2018

(30) Foreign Application Priority Data
Oct. 9, 2015    (EP) .................................. 15189061

(51) Int. Cl.
*A61M 11/00*    (2006.01)
*B05B 11/00*    (2023.01)
(Continued)

(52) U.S. Cl.
CPC ........ *A61M 11/006* (2014.02); *A61M 15/009* (2013.01); *A61M 15/0065* (2013.01);
(Continued)

(58) Field of Classification Search
CPC ............ A61M 11/006; A61M 15/0068; A61M 15/0065; A61M 2205/0238;
(Continued)

(56) References Cited

U.S. PATENT DOCUMENTS

2012/0138713 A1    6/2012    Schuy et al.

FOREIGN PATENT DOCUMENTS

CA           2513167 A1     10/2004
DE    102005015573 B4      1/2014
(Continued)

OTHER PUBLICATIONS

Abstract in English for DE 102005015573, Oct. 5, 2006.
(Continued)

*Primary Examiner* — Robert S Walters, Jr.
(74) *Attorney, Agent, or Firm* — Morgan, Lewis & Bockius LLP

(57) ABSTRACT

The present disclosure provides a method for the surface modification of microstructured components having a polar surface, in particular for high-pressure applications. According to the method, a microstructured component is contacted, in particular treated, with a modification reagent, wherein the surface properties of the component are modified by chemical and/or physical interaction of the component surface and of the modification reagent.

14 Claims, 13 Drawing Sheets

Figure 1:
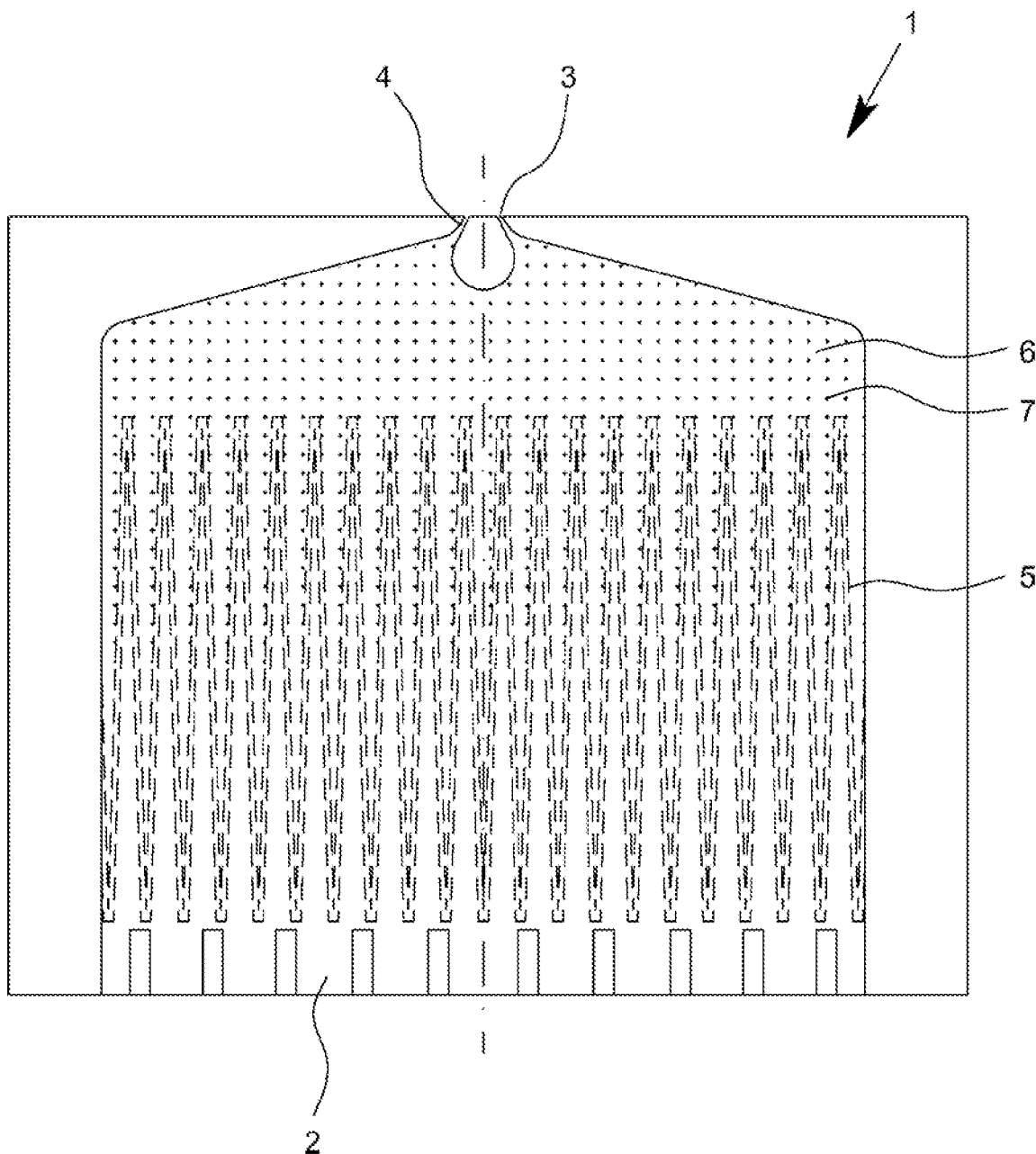

(51) Int. Cl.
 *A61M 15/00*   (2006.01)
 *B81C 1/00*   (2006.01)
 *B05B 13/04*   (2006.01)
 *B05B 1/16*   (2006.01)
 *B05B 1/20*   (2006.01)
 *B05B 1/04*   (2006.01)
 *B01J 2/06*   (2006.01)
 *B05D 7/00*   (2006.01)
 *B01J 2/04*   (2006.01)
 *B05D 7/24*   (2006.01)
 *C09D 183/08*   (2006.01)
 *C03C 17/30*   (2006.01)
 *B05B 11/10*   (2023.01)
 *B05D 5/08*   (2006.01)

(52) U.S. Cl.
 CPC ............ *A61M 15/0068* (2014.02); *B01J 2/04* (2013.01); *B01J 2/06* (2013.01); *B05B 1/042* (2013.01); *B05B 1/16* (2013.01); *B05B 1/202* (2013.01); *B05B 11/0032* (2013.01); *B05B 13/0436* (2013.01); *B05D 7/00* (2013.01); *B05D 7/24* (2013.01); *B81C 1/00* (2013.01); *B81C 1/00015* (2013.01); *B81C 1/0038* (2013.01); *B81C 1/0065* (2013.01); *B81C 1/00206* (2013.01); *B81C 1/00341* (2013.01); *B81C 1/00349* (2013.01); *B81C 1/00642* (2013.01); *B81C 1/00682* (2013.01); *C03C 17/30* (2013.01); *C09D 183/08* (2013.01); *A61M 2205/0238* (2013.01); *A61M 2205/70* (2013.01); *A61M 2205/7545* (2013.01); *A61M 2205/7563* (2013.01); *A61M 2207/00* (2013.01); *B05B 11/1091* (2023.01); *B05D 5/08* (2013.01); *B05D 2518/12* (2013.01); *B81C 2201/01* (2013.01); *B81C 2201/0161* (2013.01); *B81C 2201/0174* (2013.01); *B81C 2201/0197* (2013.01)

(58) Field of Classification Search
 CPC ...... A61M 2205/70; A61M 2205/7545; A61M 2207/00; B01J 2/04; B01J 2/06; B05B 1/042; B05B 1/16; B05B 1/202; B05B 11/0032; B05B 13/0436; B05B 11/3091; B05D 7/00; B05D 7/24; B05D 5/08; B05D 2518/12; B81C 1/00; B81C 1/00206; B81C 1/00015; B81C 1/00341; B81C 1/00349; B81C 1/0038; B81C 1/00642; B81C 1/0065; B81C 1/00682; B81C 2201/01; B81C 2201/0161; B81C 2201/0174; B81C 2201/0197; C03C 17/30; C09D 183/08

See application file for complete search history.

(56) References Cited

FOREIGN PATENT DOCUMENTS

| JP | 2007517529 A | 7/2007 | | |
|---|---|---|---|---|
| JP | 2010500338 A | 1/2010 | | |
| JP | 2013510704 A | 3/2013 | | |
| JP | 2010505615 A | 11/2013 | | |
| JP | 2012521875 A | 2/2015 | | |
| WO | 2004089551 A2 | 10/2004 | | |
| WO | WO-2005068399 A1 | * 7/2005 | ........... | C04B 41/009 |
| WO | 2010112358 A2 | 10/2010 | | |
| WO | WO-2015048539 A1 | * 4/2015 | ............... | B05D 5/08 |

OTHER PUBLICATIONS

Dalby et al., "A review of the development of Respimat <(>R) Soft Mist (TM) Inhaler", International Journal of Pharmaceutics, vol. 283, No. 1-2, pp. 1-9.

Fadeev et al., "Trialkylsilane Monolayers Covalently Attached to Silicon Surfaces: Wettability Studies Indicating That Molecular Topography Contributes to Contact Angle Hysteresis", American Chemical Society, 1999, vol. 15, pp. 3759-3766.

International Search Report and Written Opinion for Corresponding Application, PCT/EP2016/073929, dated Jan. 20, 2017.

Notice of Reasons for Refusal for Japanese Patent Application No. 2018518412 dated Jul. 13, 2022, 9 pages.

Decision to Grant for European Patent Application No. 16781345.0 dated Apr. 1, 2021, 2 pages.

International Preliminary Report on Patentability for PCT/EP2016/073929 dated Apr. 10, 2018, 9 pages.

Notice of Reasons for Refusal for Japanese Patent Application No. 2018518412 dated Sep. 15, 2020, 6 pages.

Decision of Refusal for Japanese Patent Application No. 2018518412 dated Aug. 12, 2021, 8 pages.

Reconsideration Report by Examiner Before Appeal for Japanese Patent Application No. 2018518412 dated Feb. 22, 2022, 5 pages.

* cited by examiner

METHOD FOR COATING MICROSTRUCTURED COMPONENTS

The present invention relates to the field of microfluidics. In particular, the present invention relates to a method for modifying, in particular hydrophobing, surfaces of microstructured substrates or components having polar surfaces.

The present invention also relates to a microstructured component comprising a surface modification. Moreover, the present invention relates to a microstructured component, in particular a nozzle system, of a microfluidic system having a modified surface.

Furthermore, the present invention relates to a discharge apparatus, in particular an atomiser for fluids, preferably in the medical field.

Lastly, the present invention relates to a method for assessing surface modifications of microstructured components.

In medicine, atomisers are used in particular as inhalation devices for treating respiratory diseases. For example, asthmatic diseases and chronic bronchitis are treated using inhalation therapies. For modern, specialist inhalation therapy, bronchial asthma and chronic bronchitis (also referred to as COPD chronic obstructive pulmonary disease) are the main indications. The two illnesses are "obstructive respiratory diseases", which account for around 90% of all respiratory diseases in total.

With its characteristic progressive deterioration of respiratory power, chronic bronchitis is one of the main causes of invalidity and death worldwide. In particular, complications and the associated stays in hospital mean bronchial asthma and COPD cause high costs for healthcare budgets around the world. With instances of the diseases increasing globally, treatment of and research into these two respiratory diseases will need to be high priorities in the future.

The aim of drug therapy by inhalation is to deposit an active substance in the lungs. Since many of the compounds used for the therapy may also have systemic effects, applying these active substances by inhalation has many advantages over oral or intravenous administration. Ideally, only the affected organ is treated, and locally high effective concentrations can be achieved. In addition, the onset of action generally occurs rapidly and systemic side effects are rare. With new bronchodilators and anti-inflammatories appearing on the market over the last few years, the situation for many asthma and COPD patients has improved. Yet much of this improvement is also down to innovations in the field of device development (cf. Ambrosino, N. and P. Paggiaro, *The management of asthma and chronic obstructive pulmonary disease: current status and future perspectives*. Expert. Rev. Respir. Med., 2012. 6(1): pp. 117-127).

The success of an inhalation therapy is dependent on the amount of medicinal product inhaled and the distribution thereof in the airways. Their distribution is affected in many different ways by a wide range of factors. These include the characteristic properties of the aerosol itself, the inhalation device used for the application, the nature of the inhalation performed by the patient and the anatomy of the airways (cf. Ganderton, D., *Targeted delivery of inhaled drugs: current challenges and future goals*. J. Aerosol Med., 1999. 12 Suppl 1: pp. S3-8; Pavia, D., *Efficacy and safety of inhalation therapy in chronic obstructive pulmonary disease and asthma*. Respirology, 1997. 2 Suppl 1: pp. S5-10).

One particularly important property of the aerosol is its particle size distribution since this has a significant impact on the deposition of aerosol particles in the airways. Aerosol particles having an aerodynamic diameter of from 2 to 5 µm perform well when inhaled into the smaller bronchioles and peripheral airways (cf. Ariyananda, P. L., J. E. Agnew, and S. W. Clarke, *Aerosol delivery systems for bronchial asthma*. Postgrad. Med. J., 1996. 72(845): pp. 151-156). By contrast, relatively large particles collide with the upper airways while smaller particles in turn end up in the alveoli and some may even be exhaled again.

To apply a medicinal product by inhalation, many portable devices are available (also referred to as devices or inhalers). These include pressurised metered dose inhalers (pMDI), which are operated using chlorofluorocarbons (CFC) or hydrofluoroalkanes (HFA), and dry powder inhalers (DPI). For many years, CFC-MDI inhalers formed the basis for bronchial asthma and chronic bronchitis treatment. However, many patients had trouble using this inhaler group and did not receive the optimum therapeutic effect in their inhalation therapy. The limitations of pMDIs and the movement towards environmentally friendly, propellant-free inhalers have sped up the development of new inhalation devices.

According to Ganderton (see above), an optimum inhalation device meets the following requirements:
high deposition of active ingredient in the lungs
slow aerosol discharge
simple to handle inhalation device
feedback to patient after dose administered
presence of a meter or content indicator
convenient format
environmentally friendly
reusable.

When Boehringer Ingelheim brought the Respimat® Soft Mist™ inhaler onto the market in 2003, a new inhalation device that met a large number of the above requirements became available. The Respimat® Soft Mist™ inhaler is a propellant-free atomiser that produces the aerosol using the mechanical energy of a spring and the collision of two liquid jets. Owing to its different principle for generating the aerosol, the inhaler could not be assigned to any of the above categories of inhalation devices; instead, it created a new type of inhalation device: soft mist inhalers (SMI). The aerosol cloud of an SMI is slower than that of a pMDI or DPI and has a much higher fine particle fraction (FPF). Owing to the relatively long duration of spray, the patient can coordinate the inhalation of the aerosol effectively and the relatively high fine particle fraction makes the deposition thereof in the deeper airways very efficient. The high fraction of respirable aerosol particles makes it possible to reduce the dose applied and thus reduces the likelihood of undesired medicinal product effects occurring (cf. Dalby, R., M. Spallek, and T. Voshaar, *A review of the development of Respimat Soft Mist Inhaler*. Int. J. Pharm., 2004. 283(1-2): pp. 1-9). WO 91/14468 A1 discloses an SMI-type apparatus for the propellant-free administration of a metered amount of a liquid medicinal product to be inhaled.

Compared with other inhalation methods in the prior art, therefore, SMI-type devices or inhalers allow respiratory diseases to be treated in a much more efficient and gentle manner. WO 2009/047173 A2 discloses an example of an SMI device. In the atomiser described therein, liquid medicinal product formulations are stored in a container and conveyed into a pressure chamber through a conveying tube in order to eventually be emitted through a nozzle. The nozzle has a liquid inlet side and a liquid outlet side. On the liquid inlet side, there is an opening through which a liquid from the pressure chamber can enter the nozzle. On the opposite side, the liquid then exits through two nozzle openings that are oriented such that the liquid jets exiting the openings collide with one another and are atomised as a result. This atomisation principle will be referred to as "double jet impinging" (DJI) in the following.

SMI-type inhalers are suitable for discharging liquid formulations, preferably based on water or water-ethanol mixtures. Within a few seconds, preferably over a time period or duration of spray of from 1 to 2 seconds, they can atomise a small amount of a liquid formulation into an aerosol suitable for inhalation therapy at the necessary therapeutic doses. By means of this device, amounts of less than 100 µl, preferably less than 20 µl, can be atomised into an aerosol using such a stroke, for example, that the inhalable proportion is preferably more than 60% and/or actually corresponds to the therapeutically effective amount.

Using the SMI-type inhalers being discussed here, a medicinal product solution is transformed, by means of a high pressure (preferably more than 50 bar) of up to 1000 bar, preferably of up to 300 bar, into a low-speed, respirable aerosol cloud that can be inhaled by the patient.

When using inhalers having small nozzle openings, the nozzle outlets can in rare cases become blocked by formulation solution residues adhering to the nozzle outlets as impurities when the atomiser is being used. This leads to the liquid jets being deflected and, in particular when DJI nozzles are used, to a change in the fine particle fraction. Precipitation of particles in the region of micronozzles can lead to the nozzle becoming blocked or clogged, which has an adverse effect on the functioning of the atomiser. This phenomenon is summarised below by the term "jet divergency". It goes without saying that the occurrence of this effect is dependent on the constituents and compositions of the formulations. In general, however, it would also be desirable to reduce nozzle blockages, which often occur due to particle accumulations, in formulations for which this effect is more likely than in others. The occurrence of accumulations is known, for example, from microfluidic systems containing free-flowing suspensions.

The occurrence of clogging in microchannels is a complex phenomenon. The potential mechanisms include the particles binding to the channel wall surface due to the presence of attraction forces and the subsequent clogging by accumulations in the flow path or by "hydrodynamic bridging". Hydrodynamic bridging refers to the phenomenon whereby particles smaller than the channel diameter reach a constriction at the same time and then block said constriction. The effect depends on both the colloidal repulsion forces and the tensile force applied. Particles are transported to the channel wall e.g. by inertia forces, Brownian motion, sedimentation or interception. The effectiveness of the particles binding always depends on the ratio of attraction and repulsion forces.

It is desirable, for example, to extend the range of application of SMIs and DJI nozzle technology to include complex formulations, for example those based on ethanolic solvents. Beneficial applications in this regard are in the field of inhalation corticoid therapy. In the field of highly effective corticosteroids specifically, the option to use an SMI to transform small amounts of formulation into a slow spray cloud would mean more effective inhalation can be expected than is currently the case in conventional inhalation devices.

The basic pharmacological therapy for bronchial asthma involves an inhaled corticosteroid (ICS) containing a long-acting $P_2$ agonist (LABA) being administered alone or in combination with other substances. The first choice in drug therapy for chronic bronchitis is the sole administration of a bronchodilator from the range of LABAs and LAMAs (long-acting antimuscarinic antagonists). Depending on the sensitivity of the COPD to a corticoid therapy, however, therapy with an ICS is also possible.

Expanding inhalation therapy by means of SMI or DJI technology would be desirable in general since it would allow drugs to be administered in a gentler and more effective manner. In this case, however, and in particular with complex formulations, the problem is that active ingredients adhere to the inhaler and can thus lead to the spray pattern deteriorating and ultimately to a nozzle blockage.

In addition, medicinal product formulations having long-term stability often have pHs that can cause reactions within the inhaler and for example the precipitation of poorly soluble compounds, which can in turn cause nozzle blockages due to particle adhesion.

Since the use of SMI-type inhalers could further reduce the occurrence of undesirable medicinal product effects, there have been many tests carried out on preventing particle adhesion and expanding the use of SMI-type inhalers and DJI-type nozzles.

To prevent impurity particles adhering in the region of the nozzle openings, WO 2004/089551 A1 discloses a microstructure or nanostructure for DJI-type nozzles and SMI-type inhalers, in which the outer surface of the liquid outlet side is microstructured or nanostructured.

In addition, WO 2010/112358 A2 discloses a method for coating an in particular microstructured surface of a component that consists of different materials, in particular glass and silicon, and the surface of which is first activated and then coated. The component is preferably a DJI nozzle that can be used in SMI-type inhalers. The component surface is activated by an oxidising solution, a basic solution or an acidic oxidising solution.

By means of the aforementioned methods and modifications to DJI nozzles, clogging or blockage of the nozzle outlet openings can be delayed or in some cases prevented. However, some of these methods are very complex and expensive, in particular in the case of the microstructured outlet openings according to WO 2004/089551 A1, or often do not reliably lead to the desired results.

The object of the present invention is therefore to mitigate or at least substantially to prevent the aforementioned problems that occur in the prior art.

In addition, another object of the present invention is to provide an improved nozzle system for the propellant-free discharge of liquids from inhalers that allows for the use of a wider range of active ingredient combinations, achieves considerably better use and performance properties and in particular has self-cleaning properties, as well as providing a method by which the use properties of nozzles can be improved and in particular self-cleaning properties on nozzles can be achieved or surface properties of nozzles can be altered.

Another object of the present invention is to expand the range of use of inhalers, in particular SMI-type inhalers.

According to a first aspect of the present invention, the present invention relates to a method for modifying, in particular hydrophobing, surfaces of microstructured components having a polar surface, in particular for high-pressure applications, wherein a microstructured component comprising silicon is brought into contact, in particular treated, with a modification reagent such that the surface properties of the component are modified by chemical and/or physical interaction between the component surface and the modification reagent, wherein the modification reagent comprises at least one modifier selected from the group consisting of silanes, siloxanes, polysiloxanes, and/or siliconates and mixtures thereof, and the modification reagent containing the modifier is present in an amount of from 0.001 to 2 mol/l based on the modification reagent. In one embodiment, the modifier is a siloxane selected from the group consisting of: alkylsiloxanes, alkylalkoxysiloxanes, arylsiloxanes and arylalkoxysiloxanes and mixtures thereof, in particular alkylsiloxanes and alkylalkoxysiloxanes and mixtures thereof, and is preferably an alkylalkoxysiloxane. In one embodiment, the modifier is a silane having organic $C_1$-$C_{20}$ groups, in particular $C_8$-$C_{18}$ groups, preferably $C_{10}$-$C_{16}$ groups. In one embodiment, the modifier is a silane of general formula I:

$$R^1{}_{4-(n+m)}SiR^2{}_m X_n \qquad (I)$$

wherein $R^1$=alkyl, in particular $C_1$-$C_{20}$ alkyl, preferably $C_8$-$C_{18}$ alkyl, preferably $C_{10}$-$C_{16}$ alkyl; aryl, in particular $C_6$-$C_{20}$ aryl, preferably $C_6$-$C_{10}$ aryl; olefin, in particular terminal olefin, preferably $C_2$-$C_{20}$ olefin, preferably $C_8$-$C_{18}$ olefin, particularly preferably $C_{10}$-$C_{16}$ olefin; fluoroalkyl, in particular $C_1$-$C_{20}$ fluoroalkyl, preferably $C_8$-$C_{18}$ fluoroalkyl, preferably $C_{10}$-$C_{16}$ fluoroalkyl, in particular comprising 1 to 40 fluorine atoms, preferably 5 to 35 fluorine atoms, preferably 10 to 30 fluorine atoms; fluoroaryl, in particular $C_6$-$C_{20}$ fluoroaryl, preferably $C_6$-$C_{10}$ fluoroaryl, in particular comprising 3 to 20 fluorine atoms, preferably 5 to 20 fluorine atoms; fluoroolefin, in particular terminal fluoroolefin, preferably $C_2$-$C_{20}$ fluoroolefin, preferably $C_8$-$C_{18}$ fluoroolefin, particularly preferably $C_{10}$-$C_{16}$ fluoroolefin, in particular comprising 1 to 30 fluorine atoms, preferably 3 to 25 fluorine atoms, preferably 5 to 25 fluorine atoms; $R^2$=alkyl, in particular $C_1$-$C_3$ alkyl, preferably methyl; X=halide, in particular chloride and/or bromide, preferably chloride; alkoxy, in particular $C_1$-$C_6$ alkoxy, particularly preferably $C_1$-$C_4$ alkoxy, most preferably $C_1$ and/or $C_2$ alkoxy; n=1 to 3, in particular 3; and m=0 to 2, in particular 0 or 2, preferably 0. In one embodiment, the silane comprises three reactive chemical functions and/or groups, in particular three hydrolysable chemical functions and/or groups, and is preferably a trialkoxysilane. In one embodiment, the silane is selected from fluoroalkyltrialkoxysilanes, the silane in particular being 1H,1H,2H,2H-tridecafluorooctyltriethoxysilane. In one embodiment, the silane is an alkyltrialkoxysilane, in Particular selected from the group consisting of $C_{12}$ alkyltrialkoxysilanes, $C_{14}$ alkyltrialkoxysilanes and $C_{16}$ alkyltrialkoxysilanes and mixtures thereof. In one embodiment, the modifier is dried and/or hardened after being brought into contact with, in particular applied to, the component. In one embodiment, the modifier is dried and/or hardened at temperatures in the range of from 20 to 250° C., in particular from 30 to 220° C., preferably from 50 to 200° C., preferably from 80 to 180° C., particularly preferably from 100 to 150° C., most preferably from 110 to 140° C. In one embodiment, the modifier is dried and/or hardened for a period of from 0.1 to 10 hours, in particular from 0.2 to 8 hours, preferably from 0.5 to 5 hours, preferably from 0.75 to 3 hours, particularly preferably from 1 to 2 hours. In one embodiment, the surface of the component is activated before the surface is brought into contact with the modification reagent. In one embodiment, the excess modification reagent is removed before or after the method step of drying and/or hardening, in particular after the method step of drying and/or hardening, by treating the component in a spin rinse dryer. In one embodiment, the method further comprises the step of determining the quality of the surface modification, in particular the hydrophobing, for each component. In one embodiment, the quality of the surface modification is determined using optical methods, in particular on the basis of image data, in particular by comparing measured parameters with target values in a spatially resolved manner. In one embodiment, the components are catagorised on the basis of the determination of the quality of the surface modification, in particular faulty components are discarded. In one embodiment, the microstructured component comprises glass, in particular silicate glass, preferably quartz glass and/or borosilicate glass, preferably borosilicate glass. In one embodiment, the component comprises elementary silicon. In one embodiment, the component comprises at least two different materials, in particular silicon and glass, the materials in particular comprising polar surfaces. In one embodiment, the surfaces of the materials of the component are modified together. In one embodiment, the component comprises microstructures in the form of channels, the channels in particular having a diameter in the range of from 0.1 to 50 µm, in particular from 0.5 to 40 µm, preferably from 1 to 20 µm, preferably from 2 to 15 µm, particularly preferably from 2.5 to 10 µm, most preferably from 3 to 8 µm. In one embodiment, the microstructures are made in the at least one of the component materials, in particular elementary silicon, in particular by drilling, milling, laser-cutting or etching, preferably by etching. In one embodiment, the microstructure is a microfluidic system. In one embodiment, the component comprises at least one inlet opening and at least one outlet opening, preferably two outlet openings, for fluids, in particular for liquids. In one embodiment, the outlet openings form nozzles for discharging a liquid. In one embodiment, the component comprises a filter region between the inlet opening and outlet opening. In one embodiment, the inner surface of the component is in particular at least substantially modified, the inner surfaces in particular being formed by channels. In one embodiment, the outer surface of the component is modified, in particular in the region of the outlet openings. In one embodiment, the entire surface of the component is modified. In one embodiment, the properties of the component surface can be adjusted in a targeted manner by means of the surface modification, in particular the hydrophobing. In one embodiment, a layer, in particular a hydrophobing layer, is applied to the surface of the component by bringing the modification reagent into contact with the surface of the component. In one embodiment, the layer is applied to the component in the form of a monolayer. In one embodiment, the layer is applied to the component in at a layer thickness of from 0.1 to 200 nm, in particular from 0.2 to 100 nm, preferably from 0.3 to 50 nm, preferably from 0.4 to 10 nm, particularly preferably from 0.5 to 3 nm. In one embodiment, the layer is bound to the component by means of chemical bonds, in particular by means of covalent bonds. In one embodiment, the siloxane is selected from $C_1$-$C_{20}$ alkylsiloxanes, in particular $C_8$-$C_{18}$ alkylsiloxanes, preferably $C_{10}$-$C_{16}$ alkylsiloxanes, and/or the siloxane is selected from $C_1$-$C_{20}$ alkylalkoxysiloxanes, in particular $C_8$-Cis alkylalkoxysiloxanes, preferably $C_{10}$-$C_{16}$ alkylalkoxysiloxanes, and/or the siloxane is selected from $C_6$-$C_{20}$ arylsiloxanes, in particular $C_6$-$C_{18}$ arylsiloxanes, preferably $C_6$-$C_{15}$ arylsiloxanes, and/or the siloxane is selected from $C_6$-$C_{20}$ arylalkoxysiloxanes, in particular $C_6$-$C_{18}$ arylalkoxysiloxanes, preferably $C_6$-$C_{15}$ arylalkoxysiloxanes. In one embodiment, the modifier is a polysiloxane selected from the group consisting of alkylpolysiloxanes, alkylalkoxypolysiloxanes, arylpolysiloxanes and arylalkoxypolysiloxanes and mixtures thereof, and is preferably a alkylalkoxypolysiloxane. In an embodiment, the modifier is a silane according to general formula II:

$$R^1_{4-(n+m)}SiR^2_mX_n \quad (II)$$

wherein:

R1=alkyl, in particular $C_1$-$C_{20}$ alkyl, preferably $C_8$-$C_{18}$ alkyl, preferably $C_{10}$-$C_{16}$ alkyl; fluoroalkyl, in particular $C_1$-$C_{20}$ fluoroalkyl, preferably $C_8$-$C_{18}$ fluoroalkyl, preferably $C_{10}$-$C_{16}$ fluoroalkyl, in particular comprising 1 to 40 fluorine atoms, preferably 5 to 35 fluorine atoms, preferably 10 to 30 fluorine atoms; $R^2$=alkyl, in particular $C_1$-$C_3$ alkyl, preferably methyl; X=halide, in particular chloride; alkoxy, in particular $C_1$-$C_6$ alkoxy, particularly preferably $C_1$-$C_4$ alkoxy, most preferably $C_1$ and/or $C_2$ alkoxy; and n=1 to 3, in particular 3, and m=0 to 2, preferably 0. In another embodiment, the modifier is a silane according to general formula III:

$$R_{4-n}SiX_n \quad (III)$$

wherein:

R=alkyl, in particular $C_1$-$C_{20}$ alkyl, preferably $C_8$-$C_{18}$ alkyl, preferably $C_{10}$-$C_{16}$ alkyl; fluoroalkyl, in particular $C_1$-$C_{20}$ fluoroalkyl, preferably $C_8$-$C_{18}$ fluoroalkyl, preferably $C_{10}$-$C_{16}$ fluoroalkyl, in particular comprising 1 to 40 fluorine atoms, preferably 5 to 35 fluorine atoms, preferably 10 to 30 fluorine atoms; X=alkoxy, preferably $C_1$-$C_4$ alkoxy, most preferably $C_1$ and/or $C_2$ alkoxy; and n=1 to 4, in particular 3. In another embodiment, the modifier is a silane according to general formula IV:

$$R^1_{4-(n+m)}SiR^2_mX_n \quad (IV)$$

wherein:

$R^1$=fluoroalkyl, in particular $C_1$-$C_{20}$ fluoroalkyl, preferably $C_8$-$C_{18}$ fluoroalkyl, preferably $C_{10}$-$C_{16}$ fluoroalkyl, in particular comprising 1 to 40 fluorine atoms, preferably 5 to 35 fluorine atoms, preferably 10 to 30 fluorine atoms; fluoroaryl, in particular $C_6$-$C_{20}$ fluoroaryl, preferably $C_6$-$C_{10}$ fluoroaryl, in particular comprising 3 to 20 fluorine atoms, preferably 5 to 20 fluorine atoms; fluoroolefin, in particular terminal fluoroolefin, preferably $C_2$-$C_{20}$ fluoroolefin, preferably $C_8$-$C_{18}$ fluoroolefin, particularly preferably $C_{10}$-$C_{16}$ fluoroolefin, in particular comprising 1 to 30 fluorine atoms, preferably 3 to 25 fluorine atoms, preferably 5 to 25 fluorine atoms; $R^2$=alkyl, in particular $C_1$-$C_3$ alkyl, preferably methyl; X=halide, in particular chloride and/or bromide, preferably chloride; alkoxy, in particular $C_1$-$C_6$ alkoxy, particularly preferably $C_1$-$C_4$ alkoxy, most preferably $C_1$ and/or $C_2$ alkoxy; n=1 to 3, in particular 3; and m=0 to 2, in particular 0 or 2, preferably 0. In another embodiment, the modifier is a silane according to general formula V:

$$R_{4-n}SiX_n \quad (V)$$

wherein:

R=fluoroalkyl, in particular $C_1$-$C_{20}$ fluoroalkyl, preferably $C_8$-$C_{18}$ fluoroalkyl, preferably $C_{10}$-$C_{16}$ fluoroalkyl, in particular comprising 1 to 40 fluorine atoms, preferably 5 to 35 fluorine atoms, preferably 10 to 30 fluorine atoms; X=alkoxy, preferably $C_1$-$C_4$ alkoxy, most preferably $C_1$ and/or $C_2$ alkoxy; and n=1 to 4, in particular 3. In another embodiment, the modifier is a silane according to general formula VI:

$$R^1_{4-(n+m)}SiR^2_mX_n \quad (VI)$$

wherein:

$R^1$=alkyl, in particular $C_1$-$C_{20}$ alkyl, preferably $C_8$-$C_{18}$ alkyl, preferably $C_{10}$-$C_{16}$ alkyl; aryl, in particular $C_6$-$C_{20}$ aryl, preferably $C_6$-$C_{10}$ aryl; olefin, in particular terminal olefin, preferably $C_2$-$C_{20}$ olefin, preferably $C_8$-$C_{18}$ olefin, particularly preferably $C_{10}$-$C_{16}$ olefin; $R^2$=alkyl, in particular $C_1$-$C_3$ alkyl, preferably methyl; X=halide, in particular chloride and/or bromide, preferably chloride; alkoxy, in particular $C_1$-$C_6$ alkoxy, particularly preferably $C_1$-$C_4$ alkoxy, most preferably $C_1$ and/or $C_2$ alkoxy; n=1 to 3, in particular 3; and m=0 to 2, in particular 0 or 2, preferably 0. In another embodiment, the modifier is a silane according to general formula VII:

$$R_{4-n}SiX_n \quad (VII)$$

wherein:

R=alkyl, in particular $C_1$-$C_{20}$ alkyl, preferably $C_8$-$C_{18}$ alkyl, preferably $C_{10}$-$C_{16}$ alkyl; X=alkoxy, preferably $C_1$-$C_4$ alkoxy, most preferably $C_1$ and/or $C_2$ alkoxy; and n=1 to 4, in particular 3. In one embodiment, the modification reagent is used in the form of a solution and/or dispersion, water and/or organic solvents in particular being used as the solvent and/or dispersion medium. In one embodiment, water and/or polar organic solvents are used as the solvent and/or dispersion medium, in particular selected from the group consisting of primary and secondary alcohols, ketones, ethers, amines, amides, esters, sulphoxides and mixtures thereof, in particular methanol, ethanol, isopropanol, dimethylether, diethylether, acetic acid ethylether, THF, DMF, DMSO and mixtures thereof, preferably ethanol and isopropanol and mixtures thereof. In one embodiment, non-polar organic solvents are used as the solvent and/or dispersion medium, in particular toluene, tetrachloromethane, chloroform, alkanes and mixtures thereof, in particular toluene, tetrachloromethane, $C_5$-$C_9$ alkanes, in particular pentane, hexane, heptane and/or octane, and mixtures thereof. In one embodiment, the modification reagent contains the modifier in concentrations of from 0.005 to 0.5 mol/l, preferably from 0.01 to 0.1 mol/l, preferably from 0.02 to 0.05 mol/l, based on the modification reagent. In one embodiment, the component is brought into contact with the modification reagent for a period of from 5 minutes to 20 hours, in particular from 30 minutes to 15 hours, preferably from 1 to 10 hours, preferably from 2 to 8 hours, particularly preferably from 4 to 7 hours. In one embodiment, the component is brought into contact with the modification reagent at a temperature in the range of from 10 to 50° C., in particular from 15 to 40° C., preferably from 20 to 30° C. In one embodiment, while in contact with the modifier, the component is treated with ultrasound at least intermittently, in particular at fixed intervals. In another aspect, the present disclosure provides a method of modifying, in particular hydrophobing, surfaces of microstructured components, in particular for high-pressure applications, as described above, wherein: (a) in a first method step, the surface of a microstructured component is activated, (b) in a subsequent method step, the microstructured component is brought into contact, in particular treated, with a modification reagent containing at least one modifier, (c) in a subsequent method step, the modifier is dried and/or hardened, and (d) in a final method step, the quality of the surface modification is determined. In one embodiment, the component is activated chemically and/or physically, preferably chemically. In one embodiment, the component is activated by the action of an activation reagent, in particular an activation solution. In one embodiment, the component is activated under acidic and/or basic conditions. In one embodiment, the component is activated under oxidising conditions, in particular under acidic and/or basic oxidising conditions. In one embodiment, the activation reagent is selected from the group consisting of acids and bases, in particular alkaline solutions and/or solutions of tetramethylammonium hydroxide, mineral acids, halogenated organic acids, piranha solution, SC-1 solutions, and mixtures thereof, in particular SC-1 solutions. In one embodiment, the activation reagent comprises water, aqueous ammonia solution and aqueous hydrogen peroxide solution in a volume-to-volume ratio in the range of from 10:1:1 to 5:2:2, preferably from 8:1:1 to 5:2:1, particularly preferably of 5:1:1, the aqueous ammonia solution comprises from 5 to 30 wt. % $NH_3$, particularly preferably 25 wt. % $NH_3$, based on the ammonia solution, and/or the aqueous hydrogen peroxide solution can comprise from 10 to 40 wt. % $H_2O_2$, preferably 30 wt. % $H_2O_2$, based on the aqueous hydrogen peroxide solution. In one embodiment, the activation solution can comprise sulphuric acid and aqueous hydrogen peroxide solution in a volume-to-volume ratio of from 20:1 to 1:1, in particular from 10:1 to 1:1, preferably from 5:1 to 1:1, preferably from 3:1 to 1:1, particularly preferably of 7:3, the sulphuric acid can be concentrated, in particular can comprise a content of from 99.0 to 99.9 wt. % $H_2SO_4$, and/or the aqueous hydrogen peroxide solution can comprise 10 to 40 wt. % $H_2O_2$, preferably 30 wt. % $H_2O_2$, based on the aqueous hydrogen peroxide solution. In one embodiment, the activation reagent is an alkaline lye, in particular caustic soda, the activation reagent comprises at least one alkali metal hydroxide, in particular sodium and/or potassium hydroxide, preferably sodium hydroxide, in amounts of from 5 to 25 wt. %, preferably of 20 wt. %, based on the activation reagent. In one embodiment, the component to be treated with the activation reagent for a period of from 0.1 to 10 hours, in particular from 0.5 to 8 hours, preferably from 1 to 5 hours. In one embodiment, the component is treated with the activation reagent at temperatures in the range of from 20 to 100° C., in particular from 30 to 90° C., preferably from 40 to 85° C., preferably from 50 to 80° C., particularly preferably from 60 to 75° C. In one embodiment, the component is cleaned, in particular is degreased, prior to activation and/or surface modification.

According to a second aspect of the present invention, the present invention relates to a microstructured component comprising a surface modification, in particular a coating, obtainable by a method comprising contacting, in particular treating, the surface of the microstructured component with a modification reagent, wherein the surface properties of the component are modified by the chemical and/or physical interaction between the microstructured component surface and the modification reagent, the modification reagent comprising at least one modifier selected from the group consisting of: silanes, siloxanes, polysiloxanes and/or siliconates and mixtures thereof, and wherein the at least one modifier is at a concentration of from 0.001 to 2 mol/l based on the modification reagent. In another aspect, the present disclosure relates to a microstructured component, in particular a nozzle system, preferably for use in a microfluidic system, comprising at least one inlet opening, at least one outlet opening and inner surfaces formed by microstructures, characterised in that the inner surfaces are modified, in particular coated, at least in part. In one embodiment, the microstructured component is characterised in that the outer surface of the component is modified, in particular coated, at least in part. In one embodiment, the component comprises channels that directly or indirectly connect the outlet opening to the inlet opening. In one embodiment, the outer surface of the component is modified, in particular coated, in particular in the region of the outlet opening. In one embodiment, the surface of the component is modified to be rendered hydrophobic, in particular is hydrophobed. In one embodiment, the surface of the component is modified by transformation using a modification reagent. In one embodiment, the modification reagent contains at least a silane, a siloxane, a polysiloxane and/or a siliconate. In one embodiment, the component comprises two outlet openings. In one embodiment, the channels of the outlet openings are oriented towards one another at an angle of from 50 to 130°, in particular from 60 to 120°, preferably from 70 to 110°, preferably from 80 to 100°, particularly preferably from 85 to 95°, most preferably at 90°. In one embodiment, the component further comprises a filter region, preferably between the inlet opening and outlet opening. In one embodiment, the microstructures, in particular the channels, have a depth and/or diameter in the range of from 0.1 to 50 μm, in particular from 0.5 to 40 μm, preferably from 1 to 20 μm, preferably from 2 to 15 μm, particularly preferably from 2.5 to 10 μm, most preferably from 3 to 8 μm. In one embodiment, the component consists of at least two different materials, in particular of glass and silicon. In one embodiment, the different materials are in particular at least substantially square, in particular plate-like. In one embodiment, the different materials are rigidly interconnected, in particular bonded. In one embodiment, at least one of the materials is microstructured on a side on which the material is connected to a second material, and thus there is a microstructure within the component as a result of the connection between the different materials.

According to a further aspect of the present invention, the present invention relates to a discharge apparatus, in particular an atomiser, for fluids, in particular for medicinal liquids, preferably liquid medicinal products, comprising at least one microstructured component comprising a surface modification, in particular a coating, obtainable by a method comprising contacting, in particular treating, the surface of the microstructured component with a modification reagent, wherein the surface properties of the component are modified by the chemical and/or physical interaction between the microstructured component surface and the modification reagent, the modification reagent comprising at least one modifier selected from the group consisting of: silanes, siloxanes, polysiloxanes and/or siliconates and mixtures thereof, and wherein the at least one modifier is at a concentration of from 0.001 to 2 mol/l based on the modification reagent. In one embodiment, the discharge apparatus comprises at least one liquid medicinal product. In one embodiment, the medicinal product is a dispersion or solution of at least one pharmaceutical active ingredient. In one embodiment, the pharmaceutical active ingredient is selected from the group consisting of terbutalin, salbutamol, trospium, in particular trospium chloride, flutropium, in particular flutropium bromide, tiotropium, in particular tiotropium bromide, oxitropium, in particular oxitropium bromide, ipratropium, in particular ipratropium bromide, fenoterol, budesonide, fluticasone, in particular fluticasone propionate, glycopyrronium, in particular glycopyrronium bromide, ciclesonide and beclometasone, in particular beclometasone propionate, and the physiologically compatible salts and derivatives thereof. In one embodiment, the solution or dispersion contains the active ingredient in amounts of from 0.01 to 100 mmol/l, in particular 0.05 to 80 mmol/l, preferably from 0.1 to 50 mmol/l, preferably from 0.5 to 20 mmol/l, particularly preferably from 0.6 to 10 mmol/l, most preferably from 0.8 to 5 mmol/1, based on the solution or dispersion. In one embodiment, the solvent or dispersion medium is selected from the group consisting of organic solvents, in particular ethanol or isopropanol, preferably ethanol, and water, and mixtures thereof. In one embodiment, the solvent or dispersion medium is selected from ethanol and water and mixtures thereof, preferably mixtures thereof, the volume-to-volume ratio of water to ethanol in the mixtures in particular varying in the range of from 10:1 to 1:50, in particular from 5:1 to 1:30, preferably from 2:1 to 1:20, preferably from 1:1 to 1:15, particularly preferably 1:2 to 1:10. In one embodiment, the solution or dispersion has a pH in the range of from 2 to 8, in particular from 2.2 to 7, preferably from 2.5 to 6.5, preferably from 2.8 to 6.

Lastly, according to a further aspect of the present invention, the present invention also relates to a method for assessing the surface modification as a microstructured component, characterised in that a provocation solution is repeatedly conducted through the microstructured component, in particular at high pressure, and the flow behaviour of the provocation solution as it exits the microstructured component is observed. In one embodiment, the quality of the surface modification, in particular the suitability of the modification reagent, is determined by the flow behaviour over time, in particular the change in the flow behaviour over time, of the provocation solution as it exits the microstructured component. In one embodiment, the flow behaviour of the provocation solution as it exits the microstructured component is observed by optical, in particular photographic, methods. In one embodiment, the microstructured component is a nozzle body, in particular a DJI nozzle. In one embodiment, the provocation solution is aqueous and/or alcoholic, in particular is a water-ethanol mixture, the provocation solution in particular having a volume-to-volume ratio of alcohol to water in the range of from 1:1 to 20:1, in particular from 3:1 to 15:1, preferably from 6:1 to 12:1, preferably of 9:1. In one embodiment, the provocation solution has a pH of at most 4, in particular of at most 3, preferably of at most 2, and/or in that the provocation solution has a pH in the range of from 0 to 4, in particular from 0.1 to 3, preferably from 1 to 2. In one embodiment, the provocation solution comprises at least one additional substance selected from silicic acids and organic chemical compounds, in particular active ingredients. In one embodiment, the provocation solution comprises the organic chemical compound, in particular the active ingredient, in amounts of from 0.01 to 5 mmol/1, in particular from 0.1 to 3 mmol/1, preferably from 0.5 to 2 mmol/1, preferably of 1 mmol/1, based on the provocation solution, and/or in that the provocation solution comprises silicic acid in amounts of from 0.001 to 2 wt. %, in particular from 0.01 to 1 wt. %, preferably from 0.05 to 0.5 wt. %, preferably of 0.1 wt. %, based on the provocation solution.

It goes without saying that, in order to avoid repetitions, special characteristics, features, designs and embodiments, and advantages or the like set out below in relation to just one aspect of the invention apply mutatis mutandis to the other aspects of the invention, without this having to be specifically mentioned.

It is also self-evident that no values, numbers or ranges set out below shall be construed as being limiting; instead, a person skilled in the art may of course deviate from the stated ranges or details in individual cases or applications, without departing from the scope of the present invention.

In addition, all the values, parameters or the like stated in the following can be determined or defined using standardised or explicitly stated determination methods or determination methods that are routine for a person skilled in the relevant art.

Moreover, it goes without saying that a person skilled in the art knows they can select all weight-based or volume-based percentage values in such a way as to come to a total of 100%; this is self-evident.

On this basis, the present invention will now be described below in more detail.

According to a first aspect of the present invention, the present invention thus relates to a method for modifying, in particular hydrophobing, surfaces of substrates or fluidic components, in particular microstructured components (such as nozzle bodies), having polar surfaces, in particular for high-pressure applications, a substrate or microstructured component being brought into contact, in particular treated, with a modification reagent, the surface properties of the substrate being modified by chemical and/or physical interaction between the component surface and the modification reagent, the modification reagent comprising at least one modifier and the modifier being selected from the group consisting of silanes, siloxanes, polysiloxanes and/or siliconates and mixtures thereof.

Within the context of the present invention, by modifying the surface of substrates or microstructured components, it has been possible to modify the surface properties thereof such that the adhesion of substances, in particular of residues of liquid solutions or dispersions conducted over or through the microstructured substrate or component, can be increased or reduced as required.

Within the context of the present invention, it is possible, by coating the substrate or microstructured component, in particular to manipulate the surface properties of the substrate or component in a targeted manner such that the interaction between the substrate or component surface and the substances, in particular fluids conducted over the surface, can be altered or reduced in a targeted manner.

Within the context of the present invention, it is possible in particular to reduce the wetting of the substrate surface by fluids conducted through or over the substrate. This is done in particular by hydrophobing the surface, i.e. the surface is preferably treated with a hydrophobic substance, as a result of which the surface energy of the substrate is reduced in particular and hydrophilic substances can no longer interact with the surface to the same extent as before.

Within the context of the present invention, treating the surface with the modification reagent should be taken to mean that the physical and/or chemical properties of the substrate surface are altered.

The substrate or microstructured component can be treated with the modification reagent in any suitable manner. Usually, however, the substrate is brought into contact with a solution or dispersion of the modification reagent, in particular is sprayed with or dipped into a solution or dispersion of the modification reagent.

In particular, within the context of the present invention, the surface modification is surprisingly able to bring excellent results even in high-pressure applications. The surface modification obtainable using the method according to the invention is not usually damaged or destroyed even at high pressures of up to 1,000 bar, in particular at pressures in the range of from 50 to 1,000 bar, in particular from 200 to 600 bar, preferably from 250 to 350 bar (tested for laminar flows running substantially in parallel with the modified surface).

Within the context of the present invention, the polar surface of the microstructured substrate is preferably formed by polar functional chemical groups. Within the context of the present invention, polar functional chemical groups should be understood to be chemical functional groups such as hydroxy groups, ester groups, carbonyl groups, amine groups, sulphane groups or similar groups that have a permanent dipole moment and render the surface of the microstructured substrate receptive in particular to interaction with other polar groups.

Within the context of the present invention, microstructured components should be understood in particular to be components that comprise, on their outer or inner surfaces, structures, e.g. in the form of channels or reliefs, having an extension in at least one spatial direction of no more than 100 µm, in particular no more than 50 µm, preferably no more than 20 µm, particularly preferably in the range of from 2 µm to 8 µm. Within the context of the present invention, it is possible to modify the surface properties of particularly fine microstructures while retaining the shape of the structure and not covering the shape or reducing the contour sharpness thereof by transformation using a coating reagent or by applying a coating.

Within the context of the present invention, the microstructured component can comprise at least two different materials. Where, within the context of the present invention, the microstructured component comprises at least two different materials, these materials usually each have polar surfaces.

Within the context of the present invention, it has also proven effective for all the materials of the microstructured component to have polar surfaces.

Within the context of the present invention, the surfaces of the materials of the component are generally modified together. Modifying the component surfaces together or simultaneously results in a particularly simple and quick modification since each material does not have to be hydrophobed separately. Coating together or simultaneously should be understood to mean that the various materials of the component are modified together preferably in terms of time and/or location. This means that the various materials of the component are preferably first interconnected and then the surface of this composite is modified, in particular by transformation using a modification reagent or modifier.

As regards the material that can be used for the microstructured component within the context of the present invention, it has proven effective for the component to comprise glass, in particular silicate glass, preferably quartz glass and/or borosilicate glass, preferably borosilicate glass, e.g. in the form of a cover on microstructures. Glass, in particular silicate glass, is a shape-retaining, sturdy, chemically inert material. In particular, glass does not usually react with organic compounds as contained in drugs or pharmaceutical compositions for example.

In addition, good results have also been achieved within the context of the present invention if the component comprises silicon, in particular elementary silicon. Where the component comprises elementary silicon, it has proven effective for at least part of the component to consist of or contain a silicon wafer. Elementary silicon has a polar surface since silicon, as a base metalloid, is always covered with a thin native oxide layer. This oxide layer is exceptionally capable of binding modification reagents or modifiers. In addition, silicon can be produced on microstructures very effectively, i.e. microstructures can be applied to silicon, in particular silicon wafers, in a simple manner. This can be done, for example, by established methods in semiconductor technology such as etching.

Within the context of the present invention, particularly good results are obtained if the component comprises, in particular consists of, elementary silicon and glass. Within the context of the present invention, therefore, it is preferable for the microstructured component to consist of glass and elementary silicon that in particular has a native oxide layer.

As regards the shape of the materials used for the component, this can vary greatly. However, it has proven effective for the different materials of the component to be in particular at least substantially square, preferably plate-like. Preferably, the different materials of the component are glass wafers and/or silicon wafers. Having the materials in a square or plate-like design makes mechanical processing simpler and allows the materials to be connected in a simple manner. Since the materials are usually connected via their largest surfaces, very sturdy composites can be obtained, in particular in the case of plate-like materials such as wafers.

Within the context of the present invention, the materials of the microstructured component can be connected in any conceivable manner, the aim being to obtain a bonded composite that is impermeable to both gases and liquids. Preferably, the different materials, in particular the glass and silicon wafers, are rigidly interconnected, for example glued, pressed or connected by means of "bonding". For further details on the bonding, reference is made here to European patent document EP 1 644 129 B1.

Within the context of the present invention, the different materials are preferably interconnected without joining agents such as adhesives, since using joining agents may leave residues in the microstructures of the component and thus the component may function less effectively or not at all.

It has been found that the method according to the invention can also be applied to the surface modification of substrates or components having any form of microstructure. Good results are obtained for components having microstructures in the form of channels. In this respect, the channels can have a diameter in the range of from 0.1 to 50 µm, in particular from 0.5 to 40 µm, preferably from 1 to 20 µm, preferably from 2 to 15 µm, particularly preferably from 2.5 to 10 µm, most preferably from 3 to 8 µm. The method according to the invention allows for the surfaces of very fine microstructures to be modified, in particular coated, without the contour sharpness of the microstructures being lost or reduced. Within the context of the present invention, the channels of the microstructured component should be understood to be channels within the microstructured component.

As regards making the microstructures in the component or component surface, these can likewise be made in many different ways. Within the context of the present invention, however, the microstructures are usually made in at least one of the component materials. In this regard, the microstructures can be made in at least one of the component materials by for example drilling, milling, laser cutting or etching, preferably by etching. Preferably, elementary silicon is provided with microstructures. Where elementary silicon is used, the microstructure is preferably made in the component material by etching. In silicon, fine microstructures can be made on a large scale and in a particularly simple manner using etching technology. To produce internal surfaces, i.e. cavities, such as channels, in the microstructured component, the microstructure is preferably made in the surface of one of the component materials, in particular in elementary silicon, and then the material is joined to a second material, in particular glass, such that the microstructure is covered by the second material and is located within the composite material or the "sandwich composite".

Within the context of the present invention, the component is generally a microfluidic system. The microstructured component thus preferably comprises channels or cavities that have a diameter of just a few micrometres and through which fluids are conducted. A particular feature of microfluidics is that fluids, in particular liquids and gases, preferably liquids, behave differently in narrow spaces than macroscopic fluids. For example, frictional forces often play a bigger role in microfluidic systems than in macroscopic systems. Capillary forces and the interaction between the fluid and the surface of the microfluidic system are also of much greater significance than in macroscopic systems, for example. In this way, it is possible for the use properties of microstructured components to be significantly altered by surface modification. Within the context of the present invention, microfluidic systems are also preferred since, in particular in medicinal product applications, especially low amounts of highly potent medicinal products have to be discharged and atomised in as uniform a manner as possible.

According to the basic principle, microfluidic systems can be divided into five different groups in principle. These are capillary-driven systems, pressure-driven systems, centrifugally-driven systems, electrokinetic systems and acoustically driven systems. In the following, some examples will be briefly explained.

In capillary-driven systems, such as lateral flow tests (LAT), also referred to as “test strips”, e.g. pregnancy test strips, the liquid is transported by means of capillary forces present.

By contrast, in “linear actuated devices”, which come under pressure-driven systems, the liquid is moved by mechanical dislocation (e.g. a pump plunger). In this case, the movement of the liquid is often restricted to one direction. This technology is integrated very frequently with calibration solutions and reaction buffers.

Centrifugally-driven systems, also known as centrifugal microfluidics, use inertia and capillary forces present in the system. Relevant inertia forces in this case are centrifugal force, Euler forces and Coriolis forces. The basic substrates are often discoid and the active liquid transport is generally directed outwards.

Electrokinetic systems use electrical charges, electrical fields, electrical field gradients or temporarily fluctuating electrical fields. This is made possible by using electrodes, making it possible for the wide range of effects (electrophoresis, dielectrophoresis, osmotic flow, polarisation) to be superimposed on one another depending on the liquid used.

Acoustically driven systems are, for example, surface acoustic waves intended for liquid transport. Surface acoustic waves (SAW) should be understood to be acoustic shock waves on a solid surface. An acoustic shock wave generates a pressure when it impinges on a droplet. If this pressure exceeds a critical value, the droplet moves on the substrate surface. Generally, the solid surface is generally coated so as to be hydrophobic and thus simplifies the droplet movement. By positioning various SAW sources on a substrate, the movement of the droplet on the substrate can be designed as desired.

Preferably, the microfluidic system used within the context of the present invention is a pressure-driven microfluidic system, preferably a nozzle system for an SMI-type inhaler, as described below. Due to its microfluidic component being the nozzle body, which preferably includes channel, filter and nozzle structures, the inhaler described below belongs to the group of pressure-driven systems, in particular to linear actuated devices.

As regards the design of the microstructured component, this can likewise vary widely. However, for the preferred application according to the invention it has proven effective for the component to comprise at least one inlet opening and at least one outlet opening, preferably two outlet openings, for fluids, in particular for liquids. The inlet and outlet openings are preferably connected, i.e. within the component there are cavities and channels through which preferably a fluid, in particular a liquid, preferably a liquid pharmaceutical composition, can be conducted.

Within the context of the present invention, particularly good results are obtained if the outlet openings form nozzles for discharging a liquid. Within the context of the present invention, the outlet openings preferably form nozzles through which a liquid, in particular a liquid pharmaceutical composition, is conducted out of the microstructured component, in particular pressed out under pressure, preferably sprayed. The liquid is preferably atomised when it exits the outlet openings or thereafter; this can be done for example by using specifically designed nozzles or by liquid jets impinging on one another as they exit the nozzles (for example in the DJI nozzles preferred in this case).

According to a preferred embodiment of the present invention, the component comprises a filter region between the inlet opening and outlet opening(s). By means of a filter region, it is possible for relatively large particles located for example within a liquid reservoir storing the liquid to be discharged, in particular the pharmaceutical composition, to be kept away from the outlet openings, in particular from the nozzles, such that the nozzles do not become clogged by relatively large particles or the liquid jet exiting the outlet openings is not deflected.

Within the context of the present invention, the inner surface of the component is usually in particular at least substantially modified. Within the context of the present invention, preferably the entire inner surface of the component is modified. In this regard, however, it is particularly important for the channels that open into the outlet openings, in particular into the nozzles, to be modified such as to prevent deposits in this region that quickly lead to the nozzles narrowing and thus to the spray pattern changing. In addition, nozzles should be prevented from becoming blocked or clogged as far as possible.

Within the context of the present invention, an inner surface of the microstructured component should be understood to be the surface within the microstructured component that is formed by cavities such as channels and nozzles. These cavities form the microfluidic system through which fluids, in particular liquids, are conducted in order to ultimately be atomised.

According to a preferred embodiment of the present invention, the outer surface of the component is also modified, in particular in the region of the outlet openings. Modifying the outer surface of the component, in particular in the region of the outlet opening, i.e. in the nozzle region, also prevents particles or dried constituents of the discharged liquid from being deposited.

Within the context of the present invention, the outer surface of the microstructured component should be understood to be the outer surface of the microstructured component, i.e. the surface that is usually visible from the outside.

Within the context of the present invention, inner surfaces can be produced, for example, by providing the outer surface of a material or of a first component part with a microstructure and then applying an additional material or a second component part to this first material, in particular to the microstructure produced (e.g. in the form of a cover). As a result, the outer microstructure of one material or of the first component part becomes an inner microstructure of the composite material or component.

Within the context of the present invention, the entire surface, i.e. the inner and outer surfaces, can be modified.

Within the context of the present invention, it is possible for the properties of the component surface to be adjusted in a targeted manner by the surface modification, in particular by the hydrophobing. Within the context of the present invention, the properties of the component surface can be adjusted in particular by selecting a suitable modifier or modification reagent.

In this respect, the modification reagent can be brought into contact with the surface of the substrate or component in any conceivable manner. Particularly good results are obtained, however, if bringing the modification reagent into contact with the surface of the substrate applies a layer, in particular a hydrophobing layer, to the surface of the substrate or component.

In this case, a layer within the context of the present invention should be understood to be not only the binder layer, such as a paint layer usually having a thickness of several micrometres, but also a monomolecular layer, which consists of a single molecule layer ("monolayers").

A layer of this kind is often also referred to as a surface functionalisation or modification, in particular when the layer is in the form of a monolayer or is formed as a monolayer. Within the context of the present invention, it is possible for the modification, in particular the coating, to be repeated multiple times such that a plurality of layers are applied. However, it is preferable for only one coating method step to be carried out, i.e. for just one layer, in particular a monolayer, to be applied.

Within the context of the present invention, particularly good results are obtained if the layer is applied to the substrate or component in the form of a monolayer. Applying monolayers makes it possible to achieve extremely thin coatings, i.e. a minimum amount of coating agent or modifier is used. Where, within the context of the present invention, the layer is applied to the substrate or component in the form of a monolayer, the monolayer is usually applied to the substrate or component as a "self-assembled monolayer" (SAM). Applying the layer in the form of a monolayer is advantageous in that the complete shape of the structures of the components is retained and contour sharpness is not lost as a result of the coating agent or modifier.

The layer applied to the substrate or component should preferably be so thin as to prevent any changes to the geometry or topology of the microstructures and such that their contour sharpness is retained. Usually, deposits as a result of particles occur in the front region of the channel structures, for example in the region of the nozzle bodies. Therefore, the coatings should be sufficiently thin for the channel geometries to be unchanged or only changed to a minor extent in this region. In addition, sufficient mechanical stability is essential for withstanding the strong forces during application. To produce thin layers or monolayers, a multiplicity of methods can be used. Usually, the Langmuir-Blodgett method is used (preferred for planar substrates; as regards the production and characterisation of "Langmuir films", reference is merely made here to the relevant prior art, e.g. Paso, K., et al., *Hydrophobic monolayer preparation by Langmuir-Blodgett and chemical adsorption techniques.* Journal of Colloid and Interface Science, 2008. 325(1): pp. 228-235) as well as adsorption from a gas phase or, as preferred in this case, from a produced solution ("solution adsorption"). The layers produced using the latter method are also referred to as SAMs. In the following, the production of self-assembled monolayers by means of liquid coating will be described in more detail. To coat a composite material as preferably used within the context of the present invention and which is often also referred to as a sandwich system, the solution adsorption method is usually the most suitable method since it allows for uniform precipitation of molecules in a complex microstructure owing to its excellent ability to penetrate cracks. In addition, capillary effects generally assist wetting of internal microstructures by a liquid modification reagent.

A self-assembled monolayer is a single layer of an organic molecule applied to a solid substrate from a liquid or gas phase. When a suitable substrate and organic molecule are selected, the molecules are chemically adsorbed by means of a chemical reaction with the substrate surface when the substrate is introduced into the gas or liquid phase.

When a self-assembled monolayer is formed from a liquid phase, the molecules position themselves on the substrate on the basis of intermolecular interactions and orient themselves relative to one another. A monolayer having a high degree of order is thus produced. Once the monolayer is completely formed, the growth of the layer stops since the substrate surface covered by molecules cannot continue to participate in the reaction. An organic ultra-thin film of this kind is referred to as a self-assembled monolayer since it forms spontaneously in a self-organising manner. The two-dimensional arrangement of the SAMs is formed in processes in which the system reached a state of equilibrium. This means that SAMs can indeed come very close to a thermodynamically stable state.

Practical examples of substrate materials in the combination of substrates and organic molecules are aluminium oxide, silver oxide or glass, gold, silver, copper or gallium arsenide and silicon oxide, titanium oxide or other oxides. Related examples of organic molecules in combination with substrates are carboxylic acids, organic sulphur compounds such as thiols, or (other) organic components. A typical combination is, for example, gold as a substrate material with thiol.

Since the molecules adsorb on the surface over the entire surface area of the substrate surface, it is possible to modify the surface properties of the substrate as desired, depending on the selection of the end terminal group. This relates not only to reducing the free surface energy by selecting an alkyl or fluoroalkyl group but can also relate to the reactivity thereof as a result of the selection of e.g. an amino or epoxy group.

Linking the bond (a siloxane bond in the case of a silicon-containing substrate) provides organosilane SAMs with stability of a covalent nature. The bond is not only linked to the surface, but, depending on the molecule selection, can also be linked to the neighbouring molecules, such as to produce a bond network (a siloxane network in the case of a silicon-containing substrate). It is for this reason that organosilane SAMs are considerably more stable than other SAMs in terms of mechanical strength and chemical stability.

Therefore, they provide the greatest number of possibilities in terms of practical use as regards the surface modification or surface functionalisation.

The thickness of an SAM is often just 1 to 2 nm and depends on the molecule length. SAMs are advantageous in that, unlike comparably large polymers, they do not vary in terms of molecule size as is common in polymers. As regards preventing adhesion in microstructures by means of surface modification, SAMs are thus the coatings preferably used within the context of the present invention.

As regards the layer thickness of the layer applied to the substrate or component, this can vary in particular according to the combination of substrate material and organic molecules. For example, the layer thickness may be influenced not only by the length of the molecules used for the coating, but also by their spatial arrangement on the surface and/or the formation of a plurality of molecule layers on top of one another. Within the context of the present invention, however, particularly good results are obtained if the layer is applied to the substrate or component at a layer thickness of from 0.1 to 200 nm, in particular from 0.2 to 100 nm, preferably from 0.3 to 50 nm, preferably from 0.4 to 10 nm, particularly preferably from 0.5 to 5 nm.

Within the context of the present invention, the layer is usually bound to the substrate or component by means of chemical bonds, in particular covalent bonds. In other words, within the context of the present invention, covalent bonds are formed between the modifier or coating agent and the substrate or component surface since these allow for particularly durable and stable compounds.

According to a preferred embodiment of the present invention, the modification reagent comprises at least one modifier, in particular at least one of the aforementioned organosilicon compounds. The modifier can be either an individual substance or a mixture of various substances.

Within the context of the present invention, the modification reagent is a substance or substance mixture with which the component or substrate is brought into contact. The modification reagent can for example be in the form of a solution or dispersion.

Within the context of the present invention, a modifier should be understood to be a chemical compound that interacts with the surface physically or chemically, for example by physisorption or chemisorption, and is bound to the surface of the component, possibly following a chemical reaction.

Within the context of the present invention, where the surface is modified as a coating, the modification reagent and the modifier are thus also referred to as coating reagents and coating agents.

As explained above, the modifier is selected from the group consisting of silanes, siloxanes, polysiloxanes and/or siliconates and mixtures thereof, in particular silanes, siloxanes and/or siliconates and mixtures thereof, preferably silanes.

By using silanes in particular, it is possible to achieve particularly thin layers, in particular monolayers, that also form a particularly sturdy composite with the substrate or component surface. In addition, silanes having many different organic groups can be commercially obtained and are also easy to manufacture, so the substrate or component surface can be modified by reaction with silanes as desired, in particular can be hydrophobed as desired.

A molecule having the structure $SiR_nX_{4-n}$ (R=organic group, X=reactive chemical group) is generally referred to as an organosilane. It is derived from the structure $SiH_4$, in which hydrogen is replaced by reactive chemical groups or organic side chains. An organic film can, for example, be formed by the functional group reacting with a hydroxy group of an oxidised substrate or component surface.

Chlorosilanes, e.g. trichloroalkylsilanes and/or alkoxyalkylsilanes, are often used as the starting material for the synthesis of a silane-based layer, in particular of an organosilane SAM. Trialkoxysilanes are precursor compounds and have to be hydrolytically split before reacting with the substrate or component surface. Compared with other SAMs, the reaction pathways of these compounds are relatively complex since each molecule has up to three reactive groups that could form a compound with the surface or one another. To provide the silanol intended for the reaction with the substrate or component surface, a small proportion of water is necessary since this is usually based on a hydrolysis reaction of the chlorine groups or alkoxy groups. Next, these silanol molecules react with free hydroxy groups of the substrate or component surface, and the siloxane scaffold can be formed via a condensation reaction; this process is also referred to as chemisorption. Following this reaction, the molecules are immobilised on the surface. Since each molecule carries a plurality of reactive groups, the siloxane bond is linked not only to molecules on the substrate or component surface, but also horizontally between adjacent molecules. This horizontal polymerisation plays a significant role in the two-dimensional arrangement of an organosilane self-assembled monolayer and generates the stability of such a coating by means of Van der Waals forces, the hydrophobic interactions and electrostatic interactions.

Where the modifier is a siloxane, it has proven effective for the modifier to be a siloxane selected from the group consisting of alkylsiloxanes, alkylalkoxysiloxanes, arylsiloxanes and arylalkoxysiloxanes and mixtures thereof, in particular alkylsiloxanes and alkylalkoxysiloxanes and mixtures thereof, the siloxane being an alkylalkoxysiloxane.

In this regard, the siloxane can be selected from $C_1$-$C_{20}$ alkylsiloxanes, in particular $C_1$-$C_{15}$ alkylsiloxanes, preferably $C_1$-$C_{12}$ alkylsiloxanes. It is also possible for the siloxane to be selected from $C_1$-$C_{20}$ alkylalkoxysiloxanes, in particular $C_1$-$C_{15}$ alkylalkoxysiloxanes, preferably $C_1$-$C_{12}$ alkylalkoxysiloxanes. In addition, the siloxane can be selected from $C_6$-$C_{20}$ arylsiloxanes, in particular $C_6$-$C_{18}$ arylsiloxanes, preferably $C_6$-$C_{15}$ arylsiloxanes. Furthermore, the siloxane can be selected from $C_6$-$C_{20}$ arylalkoxysiloxanes, in particular $C_6$-$C_{18}$ arylalkoxysiloxanes, preferably $C_6$-$C_{15}$ arylalkoxysiloxanes.

Likewise, within the context of the present invention, good results are obtained if the siloxane has a weight-average molecular weight $M_w$ in the range of from 200 to 10,000 g/mol, in particular from 500 to 8,000 g/mol, preferably from 700 to 5,000 g/mol, preferably from 1,000 to 4,000 g/mol, particularly preferably from 1,500 to 3,000 g/mol. Therefore, where siloxanes are used within the context of the present invention, low-molecular-weight siloxanes are preferably used.

The siloxanes used within the context of the present invention can also be fluorinated, in particular partially fluorinated or perfluorinated, in order to further increase the hydrophobicity of the coating obtained.

Where, within the context of the present invention, the modifier is a polysiloxane, it has also proven effective for the modifier to be a polysiloxane selected from the group consisting of alkylpolysiloxanes, arylalkoxypolysiloxanes, arylpolysiloxanes and arylalkoxypolysiloxanes and mixtures thereof, in particular alkylpolysiloxanes and alkylalkoxypolysiloxanes and mixtures thereof, and to preferably be an alkylalkoxypolysiloxane.

In this regard, the polysiloxane can be selected from $C_1$-$C_{20}$ alkylpolysiloxanes, in particular $C_1$-$C_{15}$ alkylpolysiloxanes, preferably $C_1$-$C_{12}$ alkylpolysiloxanes.

The polysiloxane can also be selected from $C_1$-$C_{20}$ alkylalkoxypolysiloxanes, in particular $C_1$-$C_{15}$ alkylalkoxypolysiloxanes, preferably $C_1$-$C_{12}$ alkylalkoxypolysiloxanes.

Equally, the polysiloxane can be selected from $C_6$-$C_{20}$ arylpolysiloxanes, in particular $C_6$-$C_{18}$ arylpolysiloxanes, preferably $C_6$-$C_{15}$ arylpolysiloxanes.

Furthermore, the polysiloxane can be selected from $C_6$-$C_{20}$ arylalkoxypolysiloxanes, in particular $C_6$-$C_{18}$ arylalkoxypolysiloxanes, preferably $C_6$-$C_{15}$ arylalkoxypolysiloxanes.

In addition, within the context of the present invention, good results can likewise be obtained if the polysiloxane has a weight-average molecular weight $M_w$ in the range of from 3,000 to 25,000 g/mol.

As regards the use of polysiloxanes, it is also possible to use partially fluorinated or perfluorinated polysiloxanes in order to increase the hydrophobicity of the coating.

Owing to the high molecular weight of the polysiloxanes, within the context of the present invention it is less preferable to use polysiloxanes compared with the use of low-molecular-weight compounds, in particular siloxanes and silanes, preferably silanes. When selecting the polysiloxanes, it must be ensured that, depending on the microstructure to be coated, they can be applied to the substrate or component surface in layer thicknesses that do not cover or clog the microstructures, weaken the contour sharpness thereof, or alter their geometry. Within the context of the present invention, it is particularly preferable to use silanes since silanes allow for particularly low layer thicknesses, in particular monolayers.

Where, within the context of the present invention, a silane is used as the modifier, a silane according to general formula I $$R^1_{4-(n+m)}SiR^2_mX_n \qquad (I)$$

can be used, where
$R^1$=alkyl, in particular $C_1$-$C_{20}$ alkyl, preferably $C_8$-$C_{18}$ alkyl, preferably $C_{10}$-$C_{16}$ alkyl;
aryl, in particular $C_6$-$C_{20}$ aryl, preferably $C_6$-$C_{10}$ aryl;
olefin, in particular terminal olefin, preferably $C_2$-$C_{20}$ olefin, preferably $C_8$-$C_{18}$ olefin, particularly preferably $C_{10}$-$C_{16}$ olefin;
fluoroalkyl, in particular $C_1$-$C_{20}$ fluoroalkyl, preferably $C_8$-$C_{18}$ fluoroalkyl, preferably $C_{10}$-$C_{16}$ fluoroalkyl, in particular comprising 1 to 40 fluorine atoms, preferably 5 to 35 fluorine atoms, preferably 10 to 30 fluorine atoms;
fluoroaryl, in particular $C_6$-$C_{20}$ fluoroaryl, preferably $C_6$-$C_{10}$ fluoroaryl, in particular comprising 3 to 20 fluorine atoms, preferably 5 to 20 fluorine atoms;
fluoroolefin, in particular terminal fluoroolefin, preferably $C_2$-$C_{20}$ fluoroolefin, preferably $C_8$-$C_{18}$ fluoroolefin, particularly preferably $C_{10}$-$C_{16}$ fluoroolefin, in particular comprising 1 to 30 fluorine atoms, preferably 3 to 25 fluorine atoms, preferably 5 to 25 fluorine atoms;
$R^2$=alkyl, in particular $C_1$-$C_3$ alkyl, preferably methyl;
X=halide, in particular chloride and/or bromide, preferably chloride;
alkoxy, in particular $C_1$-$C_6$ alkoxy, particularly preferably $C_1$-$C_4$ alkoxy, most preferably $C_1$ and/or $C_2$ alkoxy; and
n=1 to 3, in particular 3, and
m=0 to 2, in particular 0 or 2, preferably 0.

In addition, within the scope of the present invention, the group X can also be formed by additional reactive, in particular hydrolysable, chemical groups.

Within the context of the present invention, particularly good results are obtained if, for the modifier, a silane according to general formula II $$R^1_{4-(n+m)}SiR^2_mX_n \qquad (II)$$

Is used, where
$R^1$=alkyl, in particular $C_1$-$C_{20}$ alkyl, preferably $C_8$-$C_{18}$ alkyl, preferably $C_{10}$-$C_{16}$ alkyl;
fluoroalkyl, in particular $C_1$-$C_{20}$ fluoroalkyl, preferably $C_8$-$C_{18}$ fluoroalkyl, preferably $C_{10}$-$C_{16}$ fluoroalkyl, in particular comprising 1 to 40 fluorine atoms, preferably 5 to 35 fluorine atoms, preferably 10 to 30 fluorine atoms;
$R^2$=alkyl, in particular $C_1$-$C_3$ alkyl, preferably methyl;
X=halide, in particular chloride;
alkoxy, in particular $C_1$-$C_6$ alkoxy, particularly preferably $C_1$-$C_4$ alkoxy, most preferably $C_1$ and/or $C_2$ alkoxy; and
n=1 to 3, in particular 3, and
m=0 to 2, in particular 0 or 2, preferably 0.

It is particularly preferable in this regard if, for the modifier, a silane according to general formula III $$R_{4-n}SiX_n \qquad (III)$$

Is used, where
R=alkyl, in particular $C_1$-$C_{20}$ alkyl, preferably $C_8$-$C_{18}$ alkyl, preferably $C_{10}$-$C_{16}$ alkyl;
fluoroalkyl, in particular $C_1$-$C_{20}$ fluoroalkyl, preferably $C_8$-$C_{18}$ fluoroalkyl, preferably $C_{10}$-$C_{16}$ fluoroalkyl, in particular comprising 1 to 40 fluorine atoms, preferably 5 to 35 fluorine atoms, preferably 10 to 30 fluorine atoms;
X=alkoxy, preferably $C_1$-$C_4$ alkoxy, most preferably $C_1$ and/or $C_2$ alkoxy; and
n=1 to 4, in particular 3.

According to a preferred embodiment of the present invention, fluorinated silanes are used as modifiers. In this regard, good results are obtained if, for the modifier, a silane according to general formula IV $$R^1_{4-(n+m)}SiR^2_mX_n \qquad (IV)$$

Is used, where
$R^1$=fluoroalkyl, in particular $C_1$-$C_{20}$ fluoroalkyl, preferably $C_8$-$C_{18}$ fluoroalkyl, preferably $C_{10}$-$C_{16}$ fluoroalkyl, in particular comprising 1 to 40 fluorine atoms, preferably 5 to 35 fluorine atoms, preferably 10 to 30 fluorine atoms;
fluoroaryl, in particular $C_6$-$C_{20}$ fluoroaryl, preferably $C_6$-$C_{10}$ fluoroaryl, in particular comprising 3 to 20 fluorine atoms, preferably 5 to 20 fluorine atoms;
fluoroolefin, in particular terminal fluoroolefin, preferably $C_2$-$C_{20}$ fluoroolefin, preferably $C_8$-$C_{18}$ fluoroolefin, particularly preferably $C_{10}$-$C_{16}$ fluoroolefin, in particular comprising 1 to 30 fluorine atoms, preferably 3 to 25 fluorine atoms, preferably 5 to 25 fluorine atoms;
$R^2$=alkyl, in particular $C_1$-$C_3$ alkyl, preferably methyl;
X=halide, in particular chloride and/or bromide, preferably chloride;
alkoxy, in particular $C_1$-$C_6$ alkoxy, particularly preferably $C_1$-$C_4$ alkoxy, most preferably $C_1$ and/or $C_2$ alkoxy; and
n=1 to 3, in particular 3, and
m=0 to 2, in particular 0 or 2, preferably 0.

In this regard, it has proven effective if, for the modifier, a silane according to general formula V $$R_{4-n}SiX_n \qquad (V)$$

is used where
R=fluoroalkyl, in particular $C_1$-$C_{20}$ fluoroalkyl, preferably $C_8$-$C_{18}$ fluoroalkyl, preferably $C_{10}$-$C_{16}$ fluoroalkyl, in particular comprising 1 to 40 fluorine atoms, preferably 5 to 35 fluorine atoms, preferably 10 to 30 fluorine atoms;
X=alkoxy, preferably $C_1$-$C_4$ alkoxy, most preferably $C_1$ and/or $C_2$ alkoxy; and
n=1 to 4, in particular 3.

In the case of fluorosilanes, in particular fluoroalkylsilanes, that comprise alkoxy groups, particularly durable coatings having excellent long-term performance can be achieved on microstructured components or substrates. The coatings have excellent hydrophobicity and remain bound to the substrate or component for long periods of time, even in high-pressure applications.

According to another, particularly preferred embodiment of the present invention, for the modifier, a silane according to general formula VI

$$R^1_{4-(n+m)}SiR^2_mX_n \quad (VI)$$

is used, where
R$^1$=alkyl, in particular C$_1$-C$_{20}$ alkyl, preferably C$_8$-C$_{18}$ alkyl, preferably C$_{10}$-C$_{16}$ alkyl;
aryl, in particular C$_6$-C$_{20}$ aryl, preferably C$_6$-C$_{10}$ aryl;
olefin, in particular terminal olefin, preferably C$_2$-C$_{20}$ olefin, preferably C$_8$-C$_{18}$ olefin, particularly preferably C$_{10}$-C$_{16}$ olefin;
R$^2$=alkyl, in particular C$_1$-C$_3$ alkyl, preferably methyl;
X=halide, in particular chloride and/or bromide, preferably chloride;
alkoxy, in particular C$_1$-C$_6$ alkoxy, particularly preferably C$_1$-C$_4$ alkoxy, most preferably C$_1$ and/or C$_2$ alkoxy; and
n=1 to 3, in particular 3, and
m=0 to 2, in particular 0 or 2, preferably 0.

In this regard, particularly good results are obtained if, for the modifier, a silane according to general formula VII

$$R_{4-n}SiX_n \quad (VII)$$

is used, where
R=alkyl, in particular C$_1$-C$_{20}$ alkyl, preferably C$_8$-C$_{18}$ alkyl, preferably C$_{10}$-C$_{16}$ alkyl;
X=alkoxy, preferably C$_1$-C$_4$ alkoxy, most preferably C$_1$ and/or C$_2$ alkoxy; and
n=1 to 4, in particular 3.

It has also proven effective if the silane comprises three reactive chemical functions and/or groups, in particular three hydrolysable chemical functions and/or groups, and is preferably a trialkoxysilane.

Within the context of the present invention, good results are also obtained if a silane having organic C$_1$-C$_{20}$ groups, in particular C$_8$-C$_{18}$ groups, preferably C$_{10}$-C$_{16}$ groups, is used as the modifier. In this regard, it has proven effective for the organic groups to be non-hydrolysable and to preferably be selected from alkyl, aryl and olefin groups that may be partially fluorinated or perfluorinated.

Within the context of the present invention, good results are obtained if the silane is selected from fluoroalkyltrialkoxysilanes, the silane in particular being 1H,1H,2H,2H-tridecafluorooctyltriethoxysilane.

In addition, particularly good results are obtained if the silane is an alkyltrialkoxysilane, in particular selected from the group consisting of C$_{12}$ alkyltrialkoxysilanes, C$_{14}$ alkyltrialkoxysilanes and C$_{16}$ alkyltrialkoxysilanes and mixtures thereof.

As the applicant surprisingly found, coatings having properties that are comparable to coatings obtained by fluorinated compounds, in particular fluoroalkylsilanes, can be achieved on the basis of organosilanes, in particular alkylsilanes, preferably having C$_{10}$-C$_{16}$ alkyl groups, particularly preferably having C$_{12}$, C$_{14}$ or C$_{16}$ alkyl groups. The coatings according to the invention on the basis of alkylsilanes cannot be removed from the surface of the substrate or component in high-pressure applications, and also produce excellent results in stress tests or "provocation tests", in particular in terms of long-term performance.

As regards the composition of the modification reagent and its manner of application, in principle any suitable option can be used. Within the context of the present invention, however, it has proven effective for the modification reagent to be used in the form of a solution and/or dispersion.

In particular when using liquid dispersions or solutions, modification reagents can be set to have a very low content of modifiers suitable for coating microstructured components with monolayers.

Within the context of the present invention, water and/or organic solvents are generally used as solvents and/or dispersion media.

As regards the specific selection of solvent and/or dispersion medium, water and/or polar organic solvents can be selected as solvents and/or dispersion media. In this regard, it has proven effective for the polar organic solvents to be selected from the group consisting of primary and secondary alcohols, ketones, ethers, amines, amides, esters, sulphoxides and mixtures thereof, in particular methanol, ethanol, isopropanol, dimethylether, diethylether, acetic acid ethylether, THF, DMF, DMSO and mixtures thereof, preferably ethanol and isopropanol and mixtures thereof. Within the context of the present invention, mixtures of water and alcohols, in particular ethanol and/or isopropanol, are preferably used.

Likewise, however, non-polar organic solvents can also be used as the solvent and/or dispersion medium within the context of the present invention, in particular toluene, tetrachloromethane, chloroform, alkanes and mixtures thereof, in particular toluene, tetrachloromethane, C$_5$-C$_9$ alkanes, in particular pentane, hexane, heptane and/or octane, and mixtures thereof. Non-polar organic solvents are primarily used when the work will take place under anhydrous conditions.

The modifier can be used in any concentration that is suitable for producing particularly thin layers, preferably monolayers, on the substrate or component surface. However, it has proven effective within the context of the present invention for the modification reagent to contain the modifier in amounts of from 0.003 to 2 mol/l, in particular from 0.006 to 0.5 mol/l, preferably from 0.01 to 0.1 mol/l, preferably from 0.02 to 0.05 mol/l, based on the modification reagent.

As for the duration for which the substrate or component, in particular the substrate or component surface, is in contact with the modification reagent, this can vary over wide ranges depending on the other conditions. Within the context of the present invention, however, it has been found that very good results can be obtained if the substrate or component is brought into contact with the modification reagent for a period of from 5 minutes to 20 hours, in particular from 30 minutes to 15 hours, preferably from 1 to 10 hours, preferably from 2 to 8 hours, particularly preferably from 4 to 7 hours.

In terms of the temperatures at which the substrate or component is brought into contact with the modification reagent, the same applies here in that in principle any temperature that allows the substrate or component to be coated in a particularly thin, homogeneous layer is suitable. However, it has been shown that good results are obtained using the modifiers or modification reagents used within the context of the present invention if the substrate or component is brought into contact with the modification reagent at a temperature in the range of from 10 to 50° C., in particular from 15 to 40° C., preferably from 20 to 30° C.

Within the context of the present invention, it has proven particularly effective for the substrate or component to be treated with ultrasound at least intermittently, in particular at fixed intervals, while in contact with the modifier. Ultrasound treatment enables the modifier to be exchanged within the capillaries and channels of the microstructured component, allowing for particularly uniform coatings.

According to a preferred embodiment of the present invention, the modifier is dried and/or hardened after being brought into contact with the substrate or component, in particular after being applied to the substrate or component. Drying, hardening or cross-linking the modifier produces, on the substrate or component, a layer, preferably in the form of a monolayer, that is at least substantially closed and is durably and rigidly bound to the substrate or component.

The temperature ranges within which the modifier is dried, hardened or cross-linked can vary widely depending on the modifier. However, particularly good results are achieved, in particular where silanes and siloxanes are used as the modifier, when the modifier is dried and/or hardened at temperatures in the range of from 20 to 250° C., in particular from 30 to 220° C., preferably from 50 to 200° C., preferably from 80 to 180° C., particularly preferably from 100 to 150° C., most preferably from 110 to 140° C. Preferably, the modifier or the coating obtained using the modifier is tempered within the aforementioned temperature ranges, such that cross-linking takes place within the layer and the layer is bound to the substrate or component surface by means of chemical bonds, in particular covalent bonds.

As for the time for which the modifier is dried and/or hardened, this is likewise highly dependent on the properties of the modifier used in each case. Within the context of the present invention, however, it has proven advantageous if the modifier is dried and/or hardened for a period of from 0.1 to 10 hours, in particular from 0.2 to 8 hours, preferably from 0.5 to 5 hours, preferably from 0.75 to 3 hours, particularly preferably from 1 to 2 hours.

Within the context of the present invention, the excess modification reagent can also be removed prior to or following the method step of drying and/or hardening. To ensure that the coated substrate or surface-modified substrate or component subsequently functions properly in the long-term, it has proven effective to remove excess modification reagent or modifier not bound to the substrate or component surface. This can be done prior to the drying or hardening, for example by mechanical removal, in particular using towels or non-woven materials or contactlessly, or following the drying or hardening, for example by rinsing using water or a solvent. Where the coated microstructured surface is freed from excess modification reagent or modifier using a solvent, at least one alcohol, in particular isopropanol and/or ethanol, preferably isopropanol, is usually used.

In this regard, particularly good results are obtained if excess modification reagent is removed from the substrate or component surface, in particular from the microstructure, prior to the drying and/or hardening. This can effectively prevent the microstructure becoming clogged or its geometry changing. In particular when the microstructured system is a nozzle system, large increases in homogeneity and reproducibility of the coating can be achieved. In this regard, excess modification reagent is preferably removed mechanically, in particular contactlessly. In this regard, contactless removal of excess modification reagent should be understood within the context of the present invention to mean that the modification reagent is removed from the surface of the substrate or component, in particular in the region of the microstructure, without parts of the cleaning apparatus coming into contact with the surface being cleaned. Preferably, the excess modification reagent is removed by means of a pressurised gas, in particular by means of compressed air, or by the action of rotary forces, e.g. in a spin rinse dryer.

Within the context of the present invention, it is preferable for the excess modification reagent to be removed by means of a spin rinse dryer, i.e. under the effect of rotary forces. Particularly good results are obtained in this regard if the rotary forces acting on the component are in the range of from 5 to 12 g, in particular from 6 to 11 g, preferably from 8 to 10 g, where "g" denotes acceleration due to gravity of 9.81 ms$^{-2}$.

Removing excess modification reagent by means of rotary forces, in particular by means of a spin rinse dryer, is advantageous firstly in that the modification reagent is reliably removed from even the finest capillary structures of the microstructured component, and secondly in that the removal of the modification reagent does not cause any evaporation effects, which, for example, lead to other modifiers precipitating out or accumulating due to concentration effects.

In this context, removing the excess modification reagent by means of rotary forces is possible at room temperature, in particular within a temperature range of from 15 to 30° C. The excess modifier can also usually be removed by rotary forces in normal ambient air. Moreover, it is simple to remove excess modification reagent using rotary forces even on industrial scales.

According to a preferred embodiment of the present invention, the surface of the substrate or component is activated before the substrate or component is brought into contact with the modification reagent. In this regard, it has proven advantageous for all the materials of the component to be activated in one operation, i.e. in one method step.

In this case, activating the substrate or component surface should be understood within the context of the present invention to mean that the substrate or component surface is chemically or physically prepared for the subsequent surface modification. This can be done, for example, by producing functional reactive groups on the substrate or component surface that can subsequently form bonds, in particular covalent chemical bonds, with the modification reagent or modifier. Activation beforehand generally considerably increases the quality of the subsequent surface modification or coatings; in particular, the long-term performance of the surface-modified substrates or components is significantly improved since activation ensures a considerably better bond between the modifier and the substrate or component surface.

According to a preferred embodiment of the method according to the invention, the method according to the invention is a method for modifying, in particular hydrophobing, surfaces of microstructured components, in particular for high-pressure applications, as described above, wherein (a) in a first method step, the surface of a microstructured component is activated (optionally after a previous additional cleaning step), (b) in a subsequent method step, the microstructured component is brought into contact, in particular treated, with a modification reagent containing at least one modifier, and (c) in a subsequent method step, the modifier is dried and/or hardened and/or cross-linked.

As regards the method step of activating the substrate or component surface, this can be carried out in many different ways. Usually, however, the substrate or component is activated chemically and/or physically, preferably chemically. In physical activation, for example, the substrate or component surface is bombarded with particles or electromagnetic radiation, such as in sputtering or plasma/corona treatment. By means of the physical treatment, the surface of the substrates or components is cleaned and (preferably at the same time) reactive chemical groups, in particular polar reactive chemical groups, are formed on the surface of the substrate or component and allow the modifier, in particular silanes, to bond during the subsequent surface modification. In chemical activation, the substrate or component surface is chemically altered by being brought into contact, in particular treated or transformed, with a chemical reagent such that reactive chemical groups, in particular polar reactive chemical groups, are formed on the surface of the substrate or component.

Within the context of the present invention, it has proven effective for the substrate or component to be activated by the action of an activation reagent, in particular an activation solution. The activation reagent or activation solution contains chemical substances that can interact with the substrate or component surface and activate said surface by chemical transformation. Glass substrates or silicon substrates, which have a native oxide layer, are usually activated such that silanol groups, i.e. free hydroxy functions, that can subsequently react with the modifier are formed on the surface of the glass or silicon dioxide layer.

Generally, the substrate or component is activated under acidic and/or basic conditions. The acids or lyes are usually Brønsted acids or bases.

Within the context of the present invention, however, it has proven advantageous for the substrate or component to be activated under oxidising conditions, in particular under acidic and/or basic oxidising conditions, preferably under acidic oxidising conditions. Under oxidising conditions, in particular acidic to slightly basic oxidising conditions, the substrate or component surface is not only activated to an excellent extent. In the process, the visual properties of the glass or silicon substrates are preferably retained, which allows for simple quality control of the microstructured components using optical methods. In addition, activation under oxidising conditions significantly increases the silanol group density on the substrate or component.

As regards the activation reagent used within the context of the present invention, a multiplicity of reagents are suitable for this in principle. Particularly good results are obtained, however, if the activation reagent is selected from the group consisting of acids and lyes, in particular alkaline lyes, solutions of tetramethylammonium hydroxide, mineral acids, such as sulphuric acid, muriatic acid or nitric acid, halogenated organic acids, piranha solution, SC-1 solutions (SC-1=Standard Clean 1 according to the RCA method; RCA=Radio Corporation of America) and mixtures thereof, preferably SC-1 solutions. For further information on the RCA method, reference is made to Kern, W., *Cleaning Solutions based on hydrogen peroxide for use in silicon semiconductor technology*. RCA review, 1970. 31: pp. 187-206.

According to an embodiment of the present invention, the activation reagent can be water, aqueous ammonia solution and aqueous hydrogen peroxide solution in a volume-to-volume ratio in the range of from 10:1:1 to 5:2:2, preferably from 8:1:1 to 5:2:1, particularly preferably of 5:1:1. These solutions are also referred to as SC-1 solutions and were developed in semiconductor technology for the RCA method in order to clean silicon wafers.

In this regard, particularly good results are obtained if the aqueous ammonia solution comprises from 5 to 30 wt. % $NH_3$, particularly preferably 25 wt. % $NH_3$, based on the ammonia solution. Equally, the aqueous hydrogen peroxide solution can comprise from 10 to 40 wt. % $H_2O_2$, preferably 30 wt. % $H_2O_2$, based on the aqueous hydrogen peroxide solution. Activation reagents of the aforementioned type are exceptionally suitable for activating glass and silicon surfaces under mild, slightly alkaline conditions, producing almost no difficult to handle waste substances.

According to a further embodiment of the invention, the activation solution can comprise sulphuric acid and aqueous hydrogen peroxide solution in a volume-to-volume ratio of from 20:1 to 1:1, in particular from 10:1 to 1:1, preferably from 5:1 to 1:1, preferably from 3:1 to 1:1, particularly preferably of 7:3. These activation solutions are usually referred to as piranha solutions or Caro's acid.

In this respect, the sulphuric acid can be concentrated, in particular can comprise a content of from 99.0 to 99.9 wt. % $H_2SO_4$, based on the sulphuric acid. Equally, the aqueous hydrogen peroxide solution can comprise from 10 to 40 wt. % $H_2O_2$, particularly preferably 30 wt. % $H_2O_2$, based on the aqueous hydrogen peroxide solution.

In addition, the activation reagent can likewise be an alkaline lye, in particular caustic soda. In this regard, particularly good results are obtained if the activation reagent comprises at least one alkali metal hydroxide, in particular sodium and/or potassium hydroxide, preferably sodium hydroxide, in amounts of from 5 to 25 wt. %, preferably of 20 wt. %, based on the activation reagent. Excellent activation of the substrate or component surface can also be achieved using the aforementioned base activation reagents. In some cases, however, in particular when using highly alkaline activation reagents, glass and/or silicon substrates may become discoloured, which makes visual component checks more difficult; for this reason, this method is less preferable within the context of the present invention.

As for the duration for which the substrate or component surface is treated with the activation reagent, this can vary over wide ranges depending on the activation reagent used in each case. Within the context of the present invention, however, it has proven effective for the substrate or component to be treated with the activation reagent for a period of from 0.1 to 10 hours, in particular from 0.5 to 8 hours, preferably from 1 to 5 hours. Treating the substrate or component surface with the activation reagent for the aforementioned periods of time allows the substrate or component surface to be completely activated, without the surface of the substrate or component being noticeably corroded or eroded.

As for the temperatures at which the substrate or component is treated with the activation reagent, this can in turn vary over wide ranges depending on the activation reagent in each case. However, it has proven advantageous for the substrate or component to be treated with the activation reagent at temperatures in the range of from 20 to 100° C., in particular from 30 to 90° C., preferably from 40 to 85° C., preferably from 50 to 80° C., particularly preferably from 60 to 75° C. Increasing the temperature slightly increases the activation rate, as a result of which the substrate or component surface is activated very effectively and uniformly, even when mild activation reagents are used.

Within the context of the present invention, it is also preferable for the activated substrate or component (in particular when the substrate or component is based on glass or elementary silicon) to be washed with water following treatment with the activation reagent and to then be stored under water until it is brought into contact with the modification reagent. In addition, particularly good results are obtained if the activation solution is at least intermittently treated with ultrasound while the substrate or component surface is being activated by the activation reagent. Ultrasound treatment allows the activation solution to be thoroughly mixed particularly uniformly, and in particular allows the activation reagent to be thoroughly mixed and exchanged even in any capillaries and fine channels located within the substrate or component.

Within the context of the present invention, the substrate or component is usually cleaned prior to activation and/or surface modification, in particular is degreased and/or freed of particles. Cleaning, in particular degreasing, the substrate or component surface has proven particularly effective when a particularly uniform coating is desired. For example, greasy residues are not always completely removed from the substrate or component surface by the aforementioned activation reagents preferably used. In other words, the parts of the substrate or component covered with the grease or fatty acids are not accessible or only insufficiently accessible for the activation, for which reason the surface is not modified or is only poorly modified at these sites. For this reason, the substrate surface should be cleaned or degreased, preferably using organic solvents, before the substrate or component surface is treated with the activation reagent.

In this regard, it has proven effective for the substrate or component to be cleaned by being treated with an in particular volatile organic solvent, in particular an alcohol, preferably ethanol or isopropanol, or a non-polar aprotic solvent. In this respect, alkanes, e.g. pentane, hexane, heptane or octane, have proven particularly effective for removing even non-polar substances from the surface of the substrate or component.

According to a particular and preferred embodiment of the present invention, in a final method step, in particular a method step (d), the quality of the surface modification, in particular the hydrophobing, is determined. In this regard, it is preferable for the quality of the surface modification to be determined for each component. A final comprehensive quality check on the microstructured component is always beneficial and is necessary in particular when the microstructured component is to be fitted in medical devices, e.g. inhalation devices.

As regards determining the quality of the surface modification, this can be carried out in many different ways. Within the context of the present invention, however, particularly good results are obtained if the quality of the surface modification is determined using optical methods, in particular on the basis of image data. In this regard, it has proven effective for the surface modification to be determined using optical methods, in particular by comparing measured parameters with target values in a spatially resolved manner.

If the component consists in part of glass, preferably of glass and silicon, the transparency to visible light can be used for a particularly effective quality check when the material is glass. Optical methods can be used to check an at least partially transparent microstructured component in a simple automated manner since it is simple to detect deviations in the thickness of the surface modification, in particular of the coating, as well as clogging in the microstructure.

Within the context of the present invention, in this regard the components are usually categorised on the basis of the determination of the quality of the surface modification, in particular faulty components are discarded. In particular, a visual quality check on the microstructured components allows microstructured components for medical applications to be produced on industrial scales.

According to a preferred embodiment of the present invention, the present invention relates to a method for modifying, in particular hydrophobing, surfaces of microstructured components having a polar surface, in particular for high-pressure applications, a microstructured component being brought into contact, in particular treated, with a modification reagent, the surface properties of the substrate being modified by chemical and/or physical interaction between the component surface and the modification reagent, the modification reagent comprising at least one modifier and a silane according to general formula VI

$$R^1{}_{4-(n+m)}SiR^2{}_m X_n \qquad (VI)$$

being used for the modifier, where
$R^1$=alkyl, in particular $C_1$-$C_{20}$ alkyl, preferably $C_8$-$C_{18}$ alkyl, preferably $C_{10}$-$C_{16}$ alkyl;
 aryl, in particular $C_6$-$C_{20}$ aryl, preferably $C_6$-$C_{10}$ aryl;
 olefin, in particular terminal olefin, preferably $C_2$-$C_{20}$ olefin, preferably $C_8$-$C_{18}$ olefin, particularly preferably $C_{10}$-$C_{16}$ olefin;
$R^2$=alkyl, in particular $C_1$-$C_3$ alkyl, preferably methyl;
X=halide, in particular chloride and/or bromide, preferably chloride;
 alkoxy, in particular $C_1$-$C_6$ alkoxy, particularly preferably $C_1$-$C_4$ alkoxy, most preferably $C_1$ and/or $C_2$ alkoxy; and
n=1 to 3, in particular 3, and
m=0 to 2, in particular 0 or 2, preferably 0.

It goes without saying that further advantageous embodiments of the method according to the invention described in connection with other embodiments of the method according to the invention also apply mutatis mutandis to this special embodiment.

According to another preferred embodiment of the present invention, the present invention relates to a method for modifying, in particular hydrophobing, surfaces of microstructured components having a polar surface, in particular for high-pressure applications, a microstructured component being brought into contact, in particular treated, with a modification reagent, the surface properties of the substrate being modified by chemical and/or physical interaction between the component surface and the modification reagent, the modification reagent comprising at least one modifier and the modifier being selected from the group consisting of silanes, siloxanes, polysiloxanes and/or siliconates and mixtures thereof, the modifier being dried and/or hardened after being brought into contact with the component and excess modification reagent being removed following the method step of drying and/or hardening by treating the component in a spin rinse dryer.

It goes without saying that further advantageous embodiments of the method according to the invention set out in connection with other embodiments of the method according to the invention also apply mutatis mutandis to this special embodiment.

According to a likewise preferred embodiment of the present invention, the present invention relates to a method for modifying, in particular hydrophobing, surfaces of microstructured components having a polar surface, in particular for high-pressure applications, a microstructured component being brought into contact, in particular treated, with a modification reagent, the surface properties of the substrate being modified by chemical and/or physical interaction between the component surface and the modification reagent, the modification reagent comprising at least one modifier and the modifier being selected from the group consisting of silanes, siloxanes, polysiloxanes and/or siliconates and mixtures thereof, the quality of the surface modification being determined in a final method step.

It goes without saying that further advantageous embodiments of the method according to the invention set out in connection with other embodiments of the method according to the invention also apply mutatis mutandis to this special embodiment.

According to a second aspect of the present invention, the present invention also relates to a microstructured component comprising a surface modification, in particular a coating, obtainable according to one of the aforementioned methods.

For further details on this aspect of the invention, reference can be made to the above explanations on the method according to the invention, which apply mutatis mutandis to the microstructured component according to the invention.

According to a third aspect of the present invention, the present invention also relates to a microstructured component, in particular a nozzle system, of a microfluidic system, comprising at least one inlet opening, at least one outlet opening and inner surfaces formed by microstructures, the inner surfaces being modified, in particular coated, at least in part.

The microstructured component according to the invention is preferably a nozzle body used in SMI-type inhalers. Particularly preferably, the component according to the invention is a DJI nozzle.

According to a preferred embodiment of the present invention, the outer surface of the component is also modified, in particular coated, in particular in the region of the outlet opening. It is preferable to coat not only the inner surfaces of the microstructured component according to the invention, but also to coat at least some regions of the outer surface, at least in the region of the outlet opening(s), since coating at least the region of the outlet opening(s) prevents particles from being deposited in this region and thus effectively counteracts the nozzles being clogged or blocked.

Within the context of the present invention, particularly good results are obtained if the surface of the component is in particular at least substantially modified, in particular coated. Therefore, it is preferable within the context of the present invention for the entire surface of the component to be in particular at least substantially modified, in particular coated.

It has proven particularly effective for the surface of the component to be modified so as to be rendered hydrophobic, in particular to be hydrophobed. When using hydrophilic substrates specifically, e.g. glass or silicon substrates, the surface properties can be adjusted in a targeted manner by hydrophobing.

Generally, the surface of the component is modified by transformation using a modification reagent.

As regards the modification reagent, this can be selected from all suitable reagents. Within the context of the present invention, however, particularly good results are obtained if the modification reagent contains at least one silane, one siloxane, one polysiloxane and/or one siliconate. For further details on the preferred modification reagents, reference can be made to the above explanations regarding the method according to the invention.

According to a preferred embodiment of the present invention, the microstructured component comprises two outlet openings. In this regard, the component can in particular comprise channels that open into the outlet opening(s).

It is also common for the channels to directly or indirectly connect the inlet openings and the outlet openings. An indirect connection between the inlet opening and outlet opening by means of the channels should be understood to mean that there are additional parts of the microstructure provided between the inlet and outlet openings, such that the channels connect the individual regions or parts of the microstructure.

According to a preferred embodiment of the present invention, the channels of the outlet openings are oriented towards one another at an angle of from 50 to 130°, in particular from 60 to 120°, preferably from 70 to 110°, preferably from 80 to 100°, particularly preferably from 85 to 95°, most preferably at 90°. Preferably, the channels are oriented such that their linear extensions intersect and form the aforementioned angles. Since the channels are oriented towards one another, fluids exiting the outlet nozzles under pressure collide with one another at a slight distance from the microstructured component and are atomised by the impact. An impact disc is formed made of finely distributed aerosol having low kinetic energy, which allows pharmaceutical active ingredients to reach deep into the lungs.

Within the context of the present invention, the component generally comprises a filter region preferably arranged between the inlet opening and the outlet opening. By means of the filter region, fine impurities contained in the fluid intended to exit through the outlet openings, in particular through the nozzles, are retained. Impurities of this kind can, for example, be produced by the fluid reacting with the walls of the fluid storage tank. In addition, it is also possible for solids to precipitate out over time while the fluid is being stored.

Within the context of the present invention, the microstructures, in particular the channels, can also have a depth and/or diameter in the range of from 0.1 to 50 μm, in particular from 0.5 to 40 μm, preferably from 1 to 20 μm, preferably from 2 to 15 μm, particularly preferably from 2.5 to 10 μm, most preferably from 3 to 8 μm. The microstructure depth should be understood to be the height difference between the microstructure and the surrounding component surface in the case of outer surface structures. The depth of the microstructures can, for example, be precisely adjusted by material-removing methods, such as milling, drilling, laser cutting or, in the case of silicon wafers, etching.

According to a particular embodiment of the present invention (not set out in more detail), outer surfaces of the component are also microstructured in particular at least in part, in particular in the region of the outlet openings. Microstructuring in the region of the outlet openings makes it possible to again effectively counteract particle adhesion, thereby preventing the outlet opening(s) from becoming blocked or clogged.

Within the context of the present invention, the component usually consists of at least two different materials, in particular glass and silicon.

Furthermore, the different materials can in particular be at least substantially square, in particular plate-like. Having the materials in a square or plate-like shape means the two materials can be connected in a particularly solid durable lasting manner since large surfaces can be interconnected.

It is also preferable for the different materials to be rigidly interconnected, in particular bonded.

Within the context of the present invention, particularly good results are obtained if at least one of the different materials is microstructured, preferably on its surface. As explained above, microstructures can be obtained within a component that comprises more than one material by at least one of the materials comprising a microstructure in one of its surfaces. By connecting the two materials, an inner surface of the composite material can be produced from the outer surface of one material.

According to a preferred embodiment of the present invention, the microstructure is obtained within the component by connecting the different materials.

For further details on this aspect of the invention, reference can be made to the above explanations on the other aspects of the invention, which apply mutatis mutandis to the microstructured component according to the invention.

Lastly, according to a fourth aspect of the present invention, the present invention relates to a discharge apparatus, in particular an atomiser, for fluids, in particular for medical liquids, preferably liquid medicinal products, comprising at least one microstructured component as described above.

Within the context of the present invention, the discharge apparatus generally comprises at least one liquid medicinal product.

The medicinal products present in the discharge apparatus or emitted thereby are usually dispersions, suspensions or solutions of at least one pharmaceutical active ingredient.

In this regard, the pharmaceutical active ingredient can be selected from the group consisting of corticosteroids and/or (para)sympathomimetics.

Particularly good results are obtained within the context of the present invention if the pharmaceutical active ingredient is selected from the group consisting of terbutalin, salbutamol, trospium, in particular trospium chloride, flutropium, in particular flutropium bromide, tiotropium, in particular tiotropium bromide, oxitropium, in particular oxitropium bromide, ipratropium, in particular ipratropium bromide, fenoterol, budesonide, fluticasone, in particular fluticasone propionate, glycopyrronium, in particular glycopyrronium bromide, ciclesonide and beclometasone, in particular beclometasone propionate, and the physiologically compatible salts and derivatives thereof.

As regards the concentration of the pharmaceutical active ingredient in the solution or dispersion, this can of course vary over wide ranges. However, particularly good results are obtained if the solution or dispersion contains the active ingredient in amounts of from 0.01 to 100 mmol/l, in particular 0.05 to 80 mmol/l, preferably from 0.1 to 50 mmol/l, preferably from 0.5 to 20 mmol/l, particularly preferably from 0.6 to 10 mmol/l, most preferably from 0.8 to 5 mmol/l, based on the solution or dispersion. Within the above concentration ranges, the compositions can be discharged from the device and atomised particularly effectively, undesirable precipitation of substances also being effectively prevented in particular.

The solvent or dispersion medium can be selected from all physiologically compatible solvents or dispersion media. Usually, the solvent or dispersion medium is selected from the group consisting of organic solvents, in particular alcohols, preferably ethanol or isopropanol, preferably ethanol, and water, and mixtures thereof.

Within the context of the present invention, formulations comprising solvents or dispersion media consisting of ethanol and water and mixtures thereof are given particular consideration; preferably, mixtures of water and ethanol in the range of from 1:80 to 1:100, particularly preferably of 1:90, are selected. In principle, however, the volume-to-volume ratios of water to ethanol in the mixtures used as solvents or dispersion media can vary over wide ranges. In particular in terms of the particle size and particle size distribution in the aerosol obtained, suitable results can also be expected in view of the present tests for mixtures in which the volume-to-volume ratio of water to ethanol in the mixtures varies in the range of from 10:1 to 1:50, in particular from 5:1 to 1:30, preferably from 2:1 to 1:20, preferably from 1:1 to 1:15, particularly preferably 1:2 to 1:10.

In addition, it has proven effective if the solution or dispersion has a pH in the range of from 2 to 8, in particular from 2.2 to 7, preferably from 2.5 to 6.5, preferably from 2.8 to 6. Within the context of the present invention, it is possible to store solutions and dispersions of medicinal products in the acidic pH range with long-term stability and to discharge them without blocking or clogging the nozzles.

Within the context of the present invention, it is preferable for the medicinal product to be an aqueous or aqueous-ethanolic solution or dispersion of budesonide.

According to a preferred embodiment of the present invention, the medicinal product is a combination of (a) at least one active ingredient A selected from the group consisting of budesonide, fluticasone, ciclesonide and beclometasone, preferably ciclesonide, and the physiologically compatible salts and derivatives thereof, and (b) at least one active ingredient B selected from the group consisting of 6-hydroxy-8-{1-hydroxy-2-[2-(4-methoxy-phenyl)-1,1-dimethyl-ethylamino]-ethyl}-4H-benzo[1,4]oxazin-3-one;

6-hydroxy-8-{1-hydroxy-2-[2-(4-phenoxy-acetic acid ethyl ester)-1,1-dimethylethylamino]-ethyl}-4H-benzo[1,4]oxazin-3-one;

6-hydroxy-8-{1-hydroxy-2-[2-(4-phenoxy-acetic acid)-1,1-dimethylethylamino]-ethyl}-4H-benzo[1,4]oxazin-3-one;

8-{2-[1,1-dimethyl-2-(2,4,6-trimethylphenyl)-ethylamino]-1-hydroxy-ethyl}-6-hydroxy-4H-benzo[1,4]oxazin-3-one;

6-hydroxy-8-{1-hydroxy-2-[2-(4-hydroxy-phenyl)-1,1-dimethylethylamino]-ethyl}-4H-benzo[1,4]oxazin-3-one;

6-hydroxy-8-{1-hydroxy-2-[2-(4-isopropyl-phenyl)-1,1-dimethylethylamino]-ethyl}-4H-benzo[1,4]oxazin-3-one;

8-{2-[2-(4-ethyl-phenyl)-1,1-dimethyl-ethylamino]-1-hydroxy-ethyl}-6-hydroxy-4H-benzo[1,4]oxazin-3-one;

8-{2-[2-(4-fluoro-3-methyl-phenyl)-1,1-dimethyl-ethylamino]-1-hydroxy-ethyl}-6-hydroxy-4H-benzo[1,4]oxazin-3-one;

8-{2-[2-(4-fluoro-2-methyl-phenyl)-1,1-dimethyl-ethylamino]-1-hydroxy-ethyl}-6-hydroxy-4H-benzo[1,4]oxazin-3-one;

8-{2-[2-(2,4-difluoro-phenyl)-1,1-dimethyl-ethylamino]-1-hydroxy-ethyl}-6-hydroxy-4H-benzo[1,4]oxazin-3-one;

8-{2-[2-(3,5-difluoro-phenyl)-1,1-dimethyl-ethylamino]-1-hydroxy-ethyl}-6-hydroxy-4H-benzo[1,4]oxazin-3-one;

8-{2-[2-(4-ethoxy-phenyl)-1,1-dimethyl-ethylamino]-1-hydroxy-ethyl}-6-hydroxy-4H-benzo[1,4]oxazin-3-one;

8-{2-[2-(3,5-dimethyl-phenyl)-1,1-dimethyl-ethylamino]-1-hydroxy-ethyl}-6-hydroxy-4H-benzo[1,4]oxazin-3-one;

4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid;

8-{2-[2-(3,4-difluoro-phenyl)-1,1-dimethyl-ethylamino]-1-hydroxy-ethyl}-6-hydroxy-4H-benzo[1,4]oxazin-3-one;

8-{2-[2-(2-chloro-4-fluoro-phenyl)-1,1-dimethyl-ethylamino]-1-hydroxy-ethyl}-6-hydroxy-4H-benzo[1,4]oxazin-3-one;

8-{2-[2-(4-chloro-phenyl)-1,1-dimethyl-ethylamino]-1-hydroxy-ethyl}-6-hydroxy-4H-benzo[1,4]oxazin-3-one;

8-{2-[2-(4-bromo-phenyl)-1,1-dimethyl-ethylamino]-1-hydroxy-ethyl}-6-hydroxy-4H-benzo[1,4]oxazin-3-one;

8-{2-[2-(4-fluoro-phenyl)-1,1-dimethyl-ethylamino]-1-hydroxy-ethyl}-6-hydroxy-4H-benzo[1,4]oxazin-3-one;

8-{2-[2-(4-fluoro-3-methoxy-phenyl)-1,1-dimethyl-ethylamino]-1-hydroxy-ethyl}-6-hydroxy-4H-benzo[1,4]oxazin-3-one;
8-{2-[2-(4-fluoro-2,6-dimethyl-phenyl)-1,1-dimethyl-ethylamino]-1-hydroxy-ethyl}-6-hydroxy-4H-benzo[1,4]oxazin-3-one;
8-{2-[2-(4-chloro-2-methyl-phenyl)-1,1-dimethyl-ethylamino]-1-hydroxy-ethyl}-6-hydroxy-4H-benzo[1,4]oxazin-3-one;
8-{2-[2-(4-chloro-3-fluoro-phenyl)-1,1-dimethyl-ethylamino]-1-hydroxy-ethyl}-6-hydroxy-4H-benzo[1,4]oxazin-3-one;
8-{2-[2-(4-chloro-2-fluoro-phenyl)-1,1-dimethyl-ethylamino]-1-hydroxy-ethyl}-6-hydroxy-4H-benzo[1,4]oxazin-3-one;
8-{2-[2-(3-chloro-4-fluoro-phenyl)-1,1-dimethyl-ethylamino]-1-hydroxy-ethyl}-6-hydroxy-4H-benzo[1,4]oxazin-3-one;
8-{2-[2-(2,6-difluoro-4-methoxy-phenyl)-1,1-dimethyl-ethylamino]-1-hydroxy-ethyl}-6-hydroxy-4H-benzo[1,4]oxazin-3-one;
8-{2-[2-(2,5-difluoro-4-methoxy-phenyl)-1,1-dimethyl-ethylamino]-1-hydroxy-ethyl}-6-hydroxy-4H-benzo[1,4]oxazin-3-one;
8-{2-[2-(4-fluoro-3,5-dimethyl-phenyl)-1,1-dimethyl-ethylamino]-1-hydroxy-ethyl}-6-hydroxy-4H-benzo[1,4]oxazin-3-one;
8-{2-[2-(3,5-dichloro-phenyl)-1,1-dimethyl-ethylamino]-1-hydroxy-ethyl}-6-hydroxy-4H-benzo[1,4]oxazin-3-one;
8-{2-[2-(4-chloro-3-methyl-phenyl)-1,1-dimethyl-ethylamino]-1-hydroxy-ethyl}-6-hydroxy-4H-benzo[1,4]oxazin-3-one;
8-{2-[2-(3,4,5-trifluoro-phenyl)-1,1-dimethyl-ethylamino]-1-hydroxy-ethyl}-6-hydroxy-4H-benzo[1,4]oxazin-3-one;
8-{2-[2-(3-methyl-phenyl)-1,1-dimethyl-ethylamino]-1-hydroxy-ethyl}-6-hydroxy-4H-benzo[1,4]oxazin-3-one; and
8-{2-[2-(3,4-dichloro-phenyl)-1,1-dimethyl-ethylamino]-1-hydroxy-ethyl}-6-hydroxy-4H-benzo[1,4]oxazin-3-one, and the physiologically compatible salts and derivatives thereof.

According to another preferred embodiment of the present invention, the medicinal product is a combination of
(a) at least one active ingredient A, as described above,
(b) at least one active ingredient B, as described above, and
(c) at least one active ingredient C selected from the group consisting of trospium, in particular trospium chloride, flutropium, in particular flutropium bromide, tiotropium, in particular tiotropium bromide, oxitropium, in particular oxitropium bromide, ipratropium, in particular ipratropium bromide, glycopyrronium, in particular glycopyrronium bromide, and the physiologically compatible salts and derivatives thereof.

For further active ingredient combinations that are preferable within the context of the present invention, reference is made to WO 2008/020056 A1 and WO 2008/020057 A1.

For further details on this aspect of the invention, reference can be made to the above explanations on the other aspects of the invention, which apply mutatis mutandis to the discharge apparatus according to the invention.

Lastly, according to a fifth aspect of the present invention, the present invention also relates to a method for assessing the surface modification of a microstructured component, a provocation solution being repeatedly conducted through the microstructured component, in particular under high pressure, and the flow behaviour of the provocation solution being observed as it exits the microstructured component.

According to a preferred embodiment of the present invention, the quality of the surface modification, in particular the suitability of the modification reagent for the surface modification, is determined by the flow behaviour over time, in particular the change in the flow behaviour over time, of the provocation solution as it exits the microstructured component.

It has been surprisingly shown that suitable provocation solutions can in a targeted manner produce deposits in the microstructure of the microstructured component that alter the flow behaviour of the solution within the component and in particular as it exits the outlet openings, specifically over very short periods of time. When the microstructured component is used in practice, for example in inhalation devices, these disruptions to the flow behaviour do not occur.

The results from the provocation tests can be used to define improved microstructures, in particular nozzle geometries, and for example to test coating reagents for their suitability for surface modification. As a result, the use of a microstructured component and the discharge apparatus can be extended to include new fields of application and new materials.

In addition, the provocation tests can also be used to identify microstructured components having better long-term performance. In the case of modification reagents in particular, there must be a sufficiently large safety margin between the conditions under which the coating no longer fulfils its purpose and the usage conditions, so that, in particular in medical inhalation devices, the user is always reliably given the therapeutic dose of medicinal products.

Within the context of the present invention, a provocation solution should be understood to be a solution or dispersion by which changes to the flow behaviour in microstructured components can be caused under conditions that are far removed from the actual conditions under which the microstructured component is used. For example, the provocation solutions can contain reactive chemical substances or particles that can lead to the microstructures becoming clogged or the flow conditions within the microstructured component being altered.

Preferably, the provocation solution is conducted through the microstructure from 10 to 1,000 times, preferably from 15 to 500 times, preferably from 25 to 250 times.

Within the context of the present invention, the flow behaviour of the provocation solution as it exits the microstructured component can be determined by optical, in particular photographic, methods. In this regard, it is possible in particular to photograph the exit of the provocation solution from the outlet openings and categorise the image data by comparing it with a catalogue compiled beforehand. In particular, this method makes it possible to study the change in the flow behaviour over time.

According to a preferred embodiment of the present invention, the microstructured component is a nozzle body, in particular a DJI nozzle.

Within the context of the present invention, the provocation solution is usually aqueous and/or alcohol-based, in particular is a water-ethanol mixture. In this regard, it has proven effective for the provocation solution to have a volume-to-volume ratio of alcohol to water in the range of from 1:1 to 20:1, in particular from 3:1 to 15:1, preferably from 6:1 to 12:1, preferably of 9:1.

In this regard, the provocation solution can also have a pH of at most 4, in particular of at most 3, preferably of at most 2. Likewise, however, good results can also be obtained if the provocation solution has a pH in the range of from 0 to 4, in particular from 0.1 to 3, preferably from 1 to 2.

According to a particular embodiment of the present invention, the provocation solution comprises at least one additional substance selected from silicic acids and organic chemical compounds, in particular active ingredients.

Where the provocation solution comprises organic chemical compounds, it has proven effective for the provocation solution to comprise the organic chemical compound, in particular the active ingredient, in amounts of from 0.01 to 5 mmol/l, in particular from 0.1 to 3 mmol/l, preferably from 0.5 to 2 mmol/l, preferably of 1 mmol/l, based on the provocation solution.

To determine the suitability of coatings or to assess their durability, a multiplicity of active ingredients can be used. In the experiments carried out to date, it has been noted that fenoterol, for example, provides particularly convincing results.

Likewise, however, the provocation solution can also comprise silicic acid in amounts of from 0.001 to 2 wt. %, in particular from 0.01 to 1 wt. %, preferably from 0.05 to 0.5 wt. %, preferably of 0.1 wt. %, based on the provocation solution.

For further details on this aspect of the invention, reference can be made to the above explanations on the other aspects of the invention, which apply mutatis mutandis to the method according to the invention for assessing the surface modification of a microstructured component.

The individual features of the present invention can be used independently of one another or combined.

Figure 2:
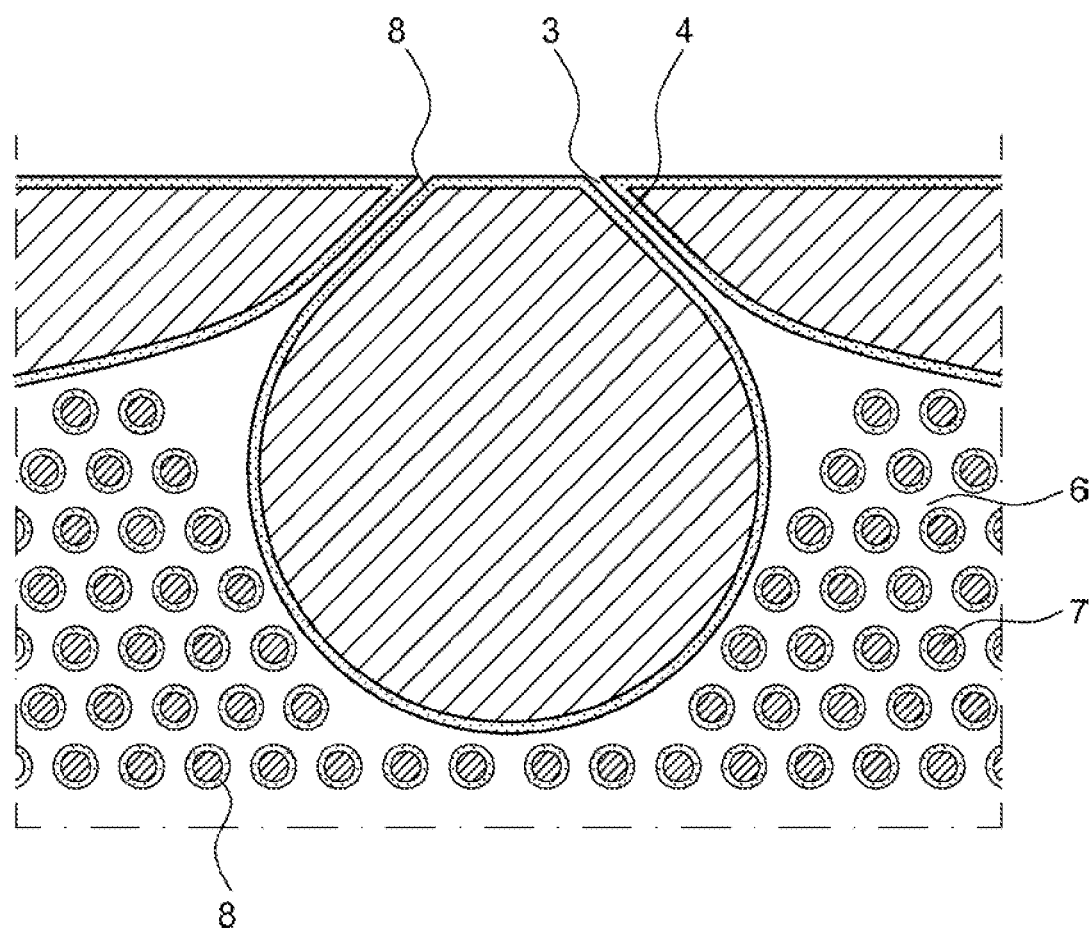
Figure 3:
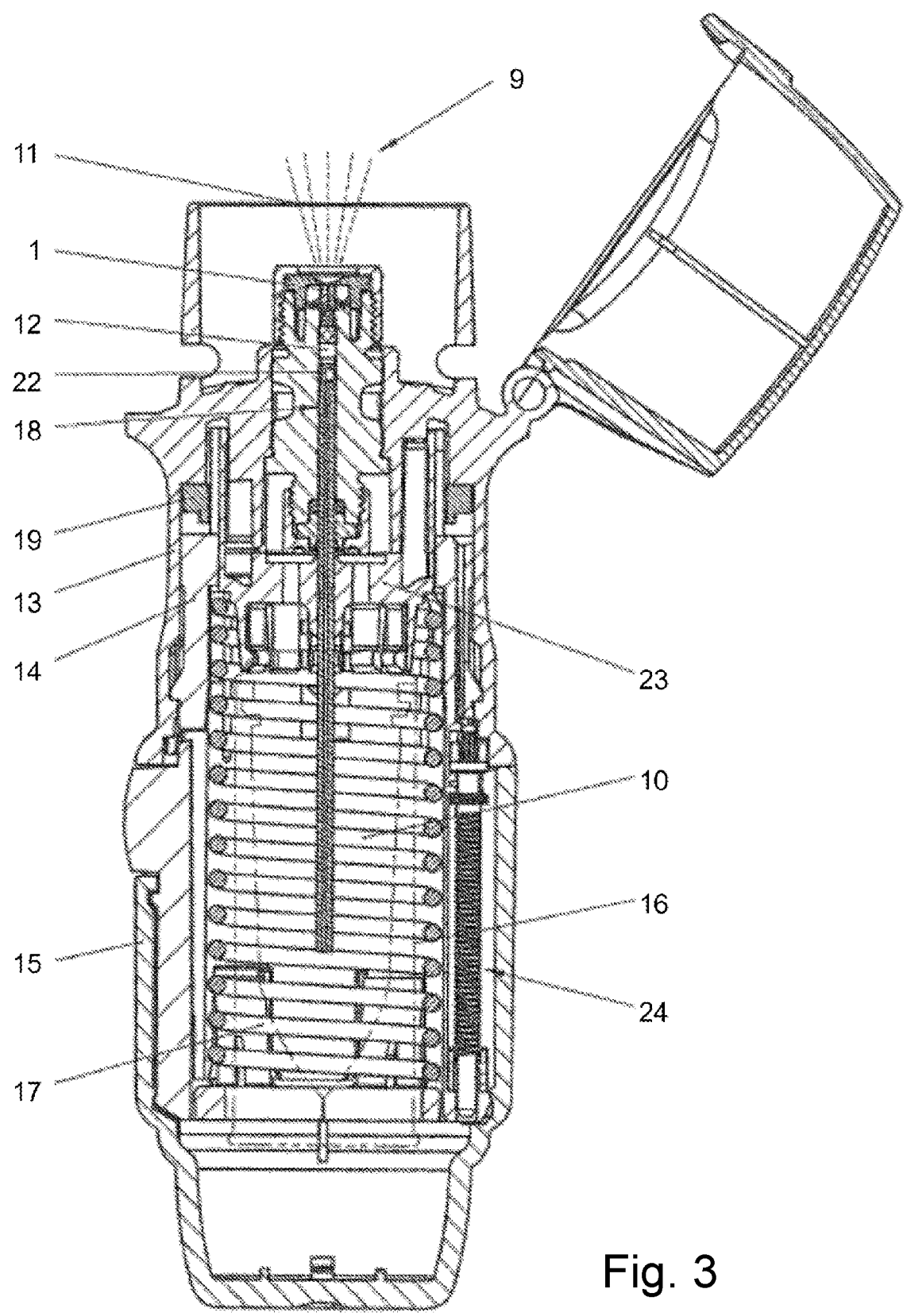
Figure 4:
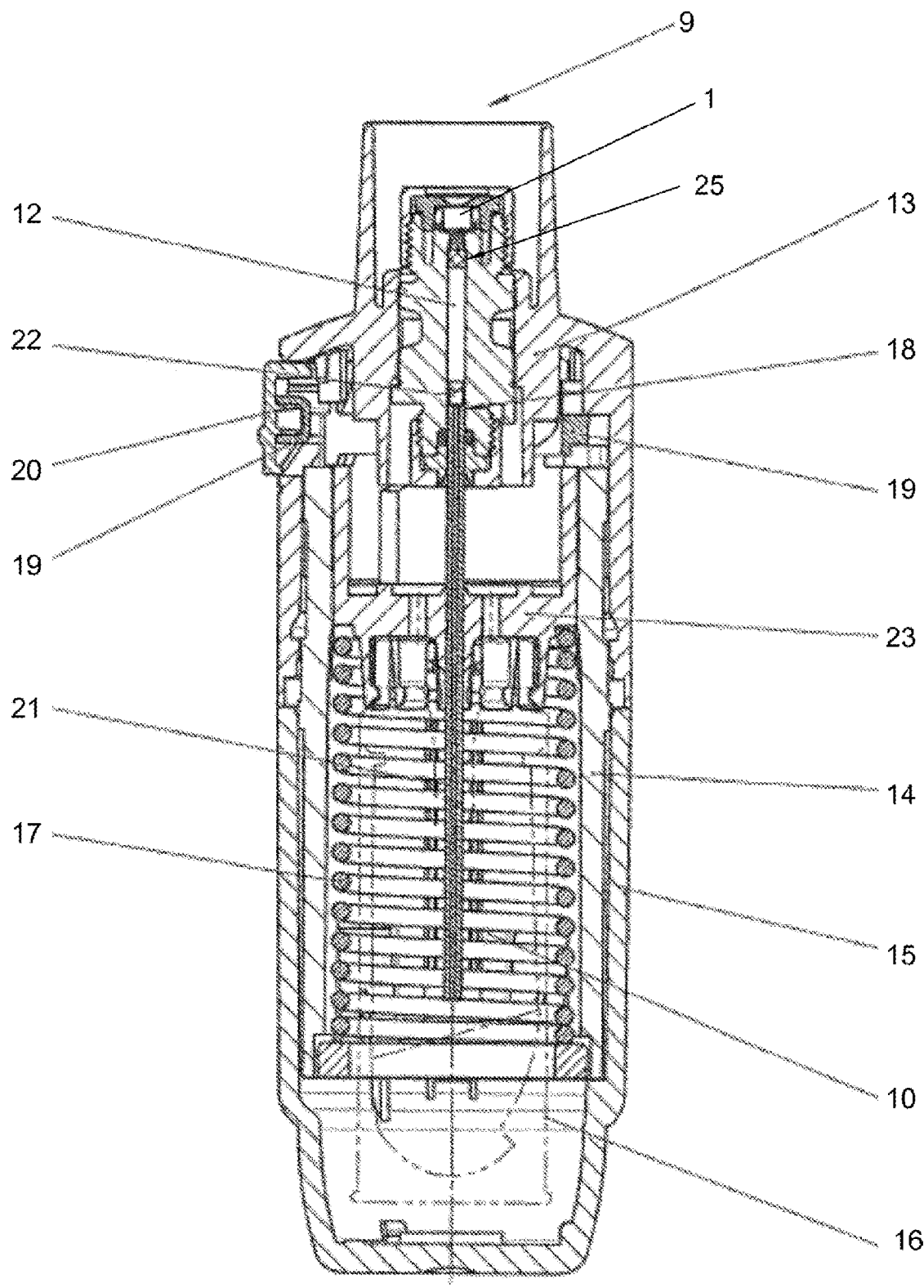
Figure 5:
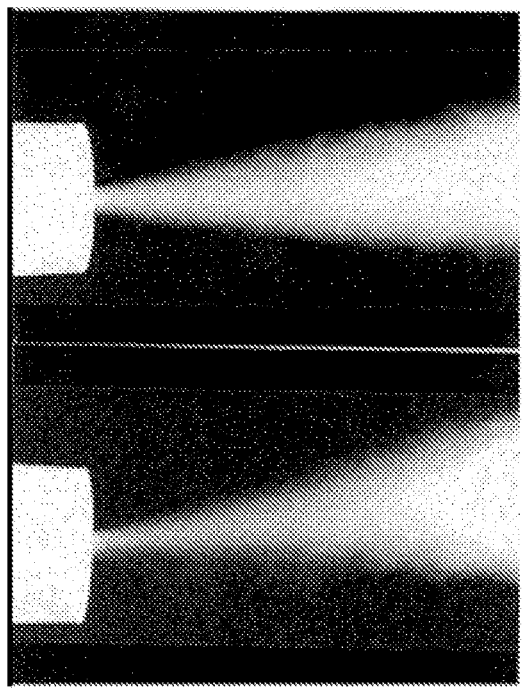
Figure 6:
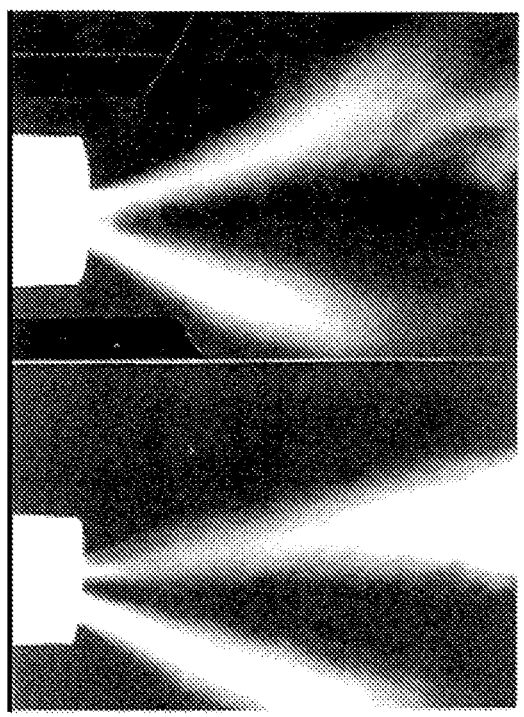
Figure 7:
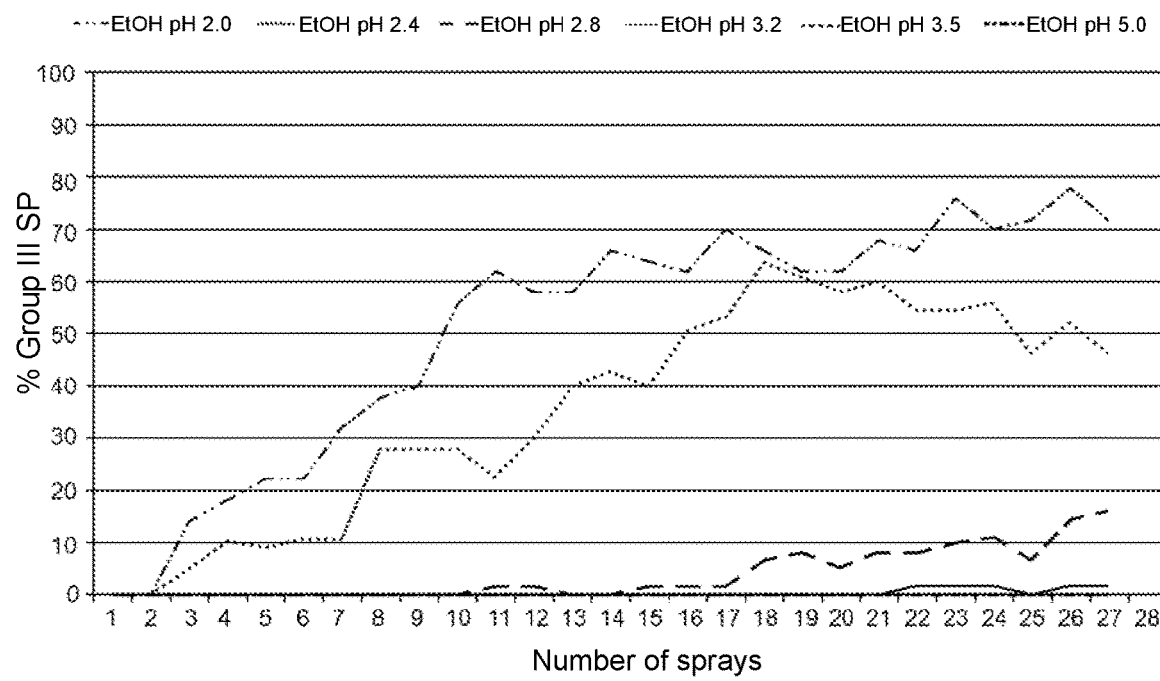
Figure 8:
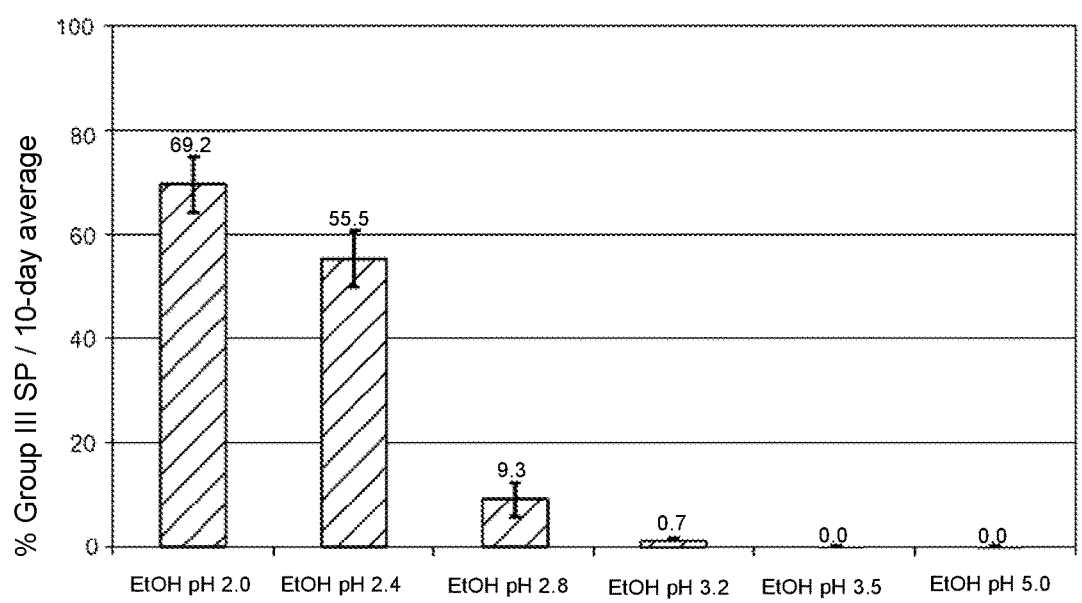
Figure 9:
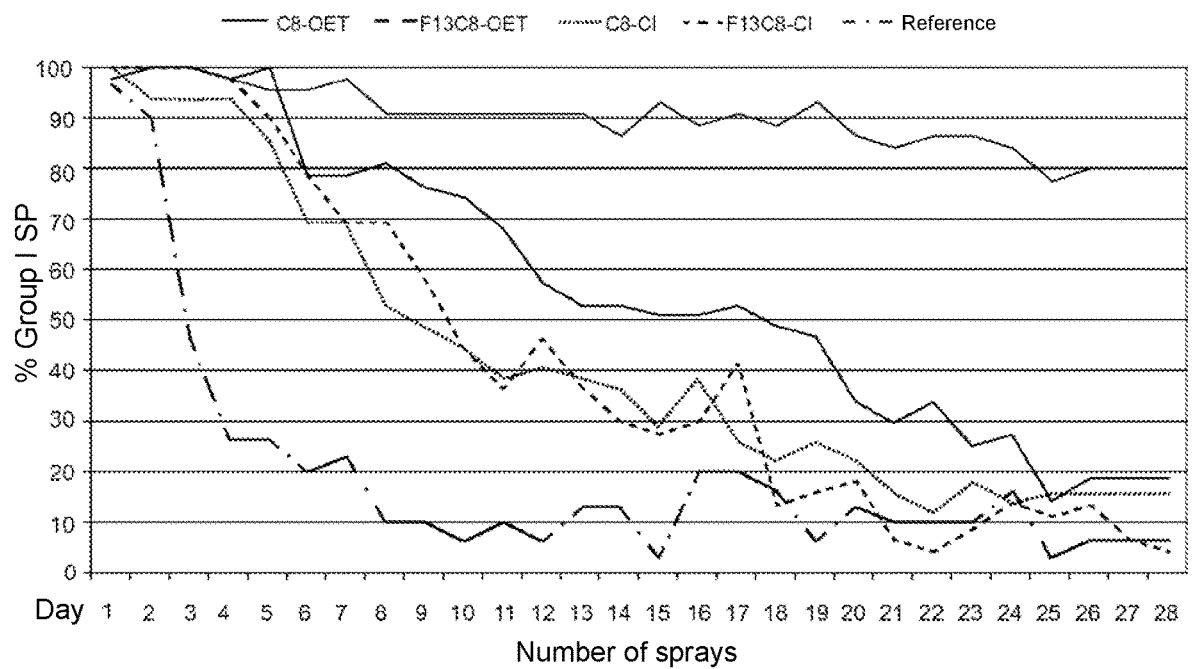
Figure 10:
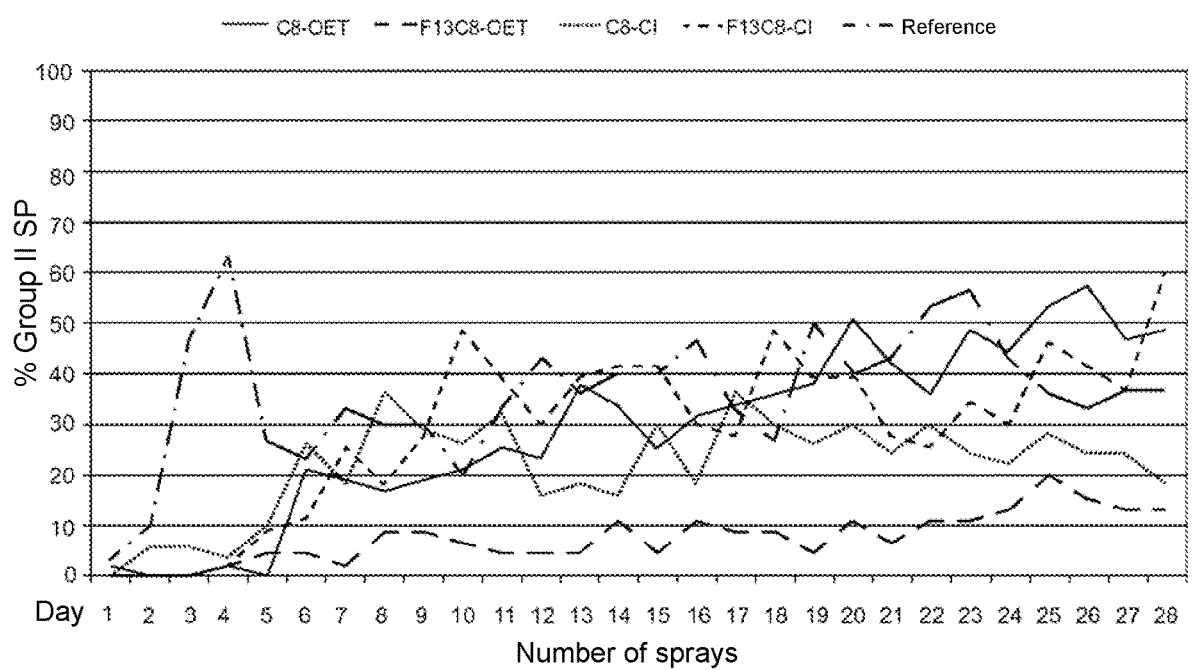
Figure 11:
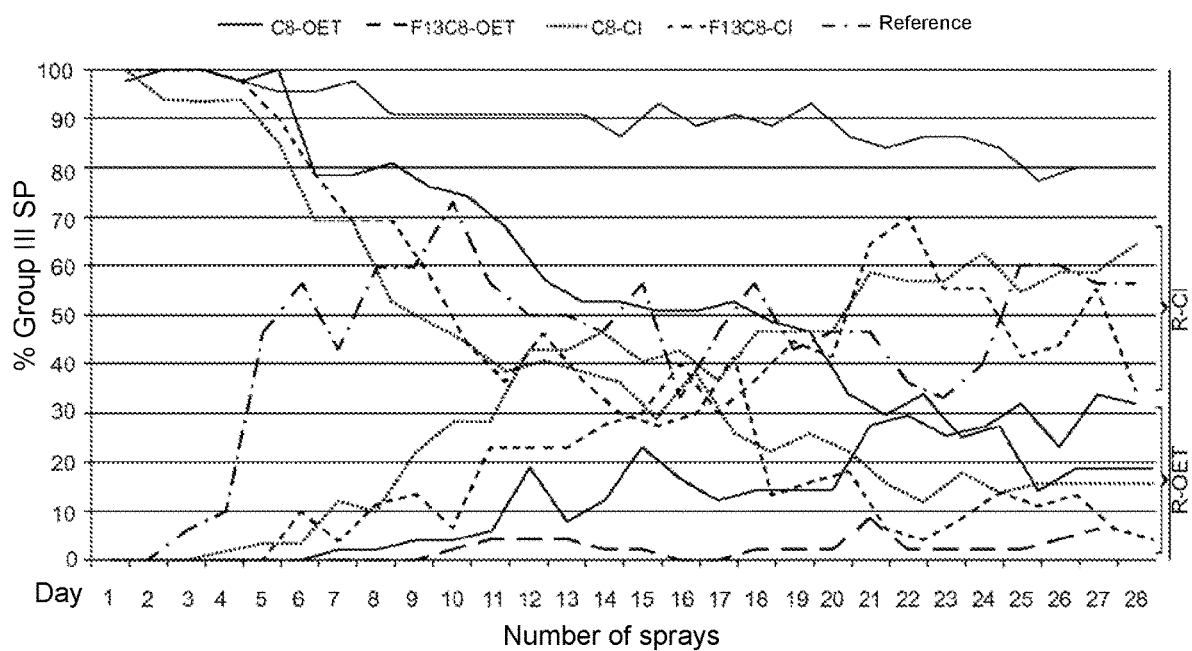
Figure 12:
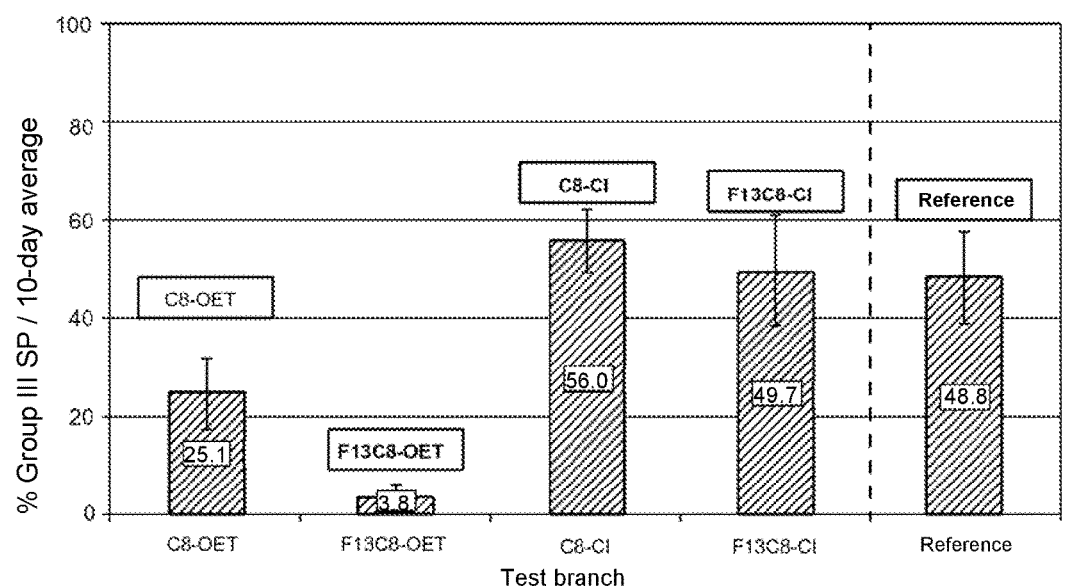
Figure 13:
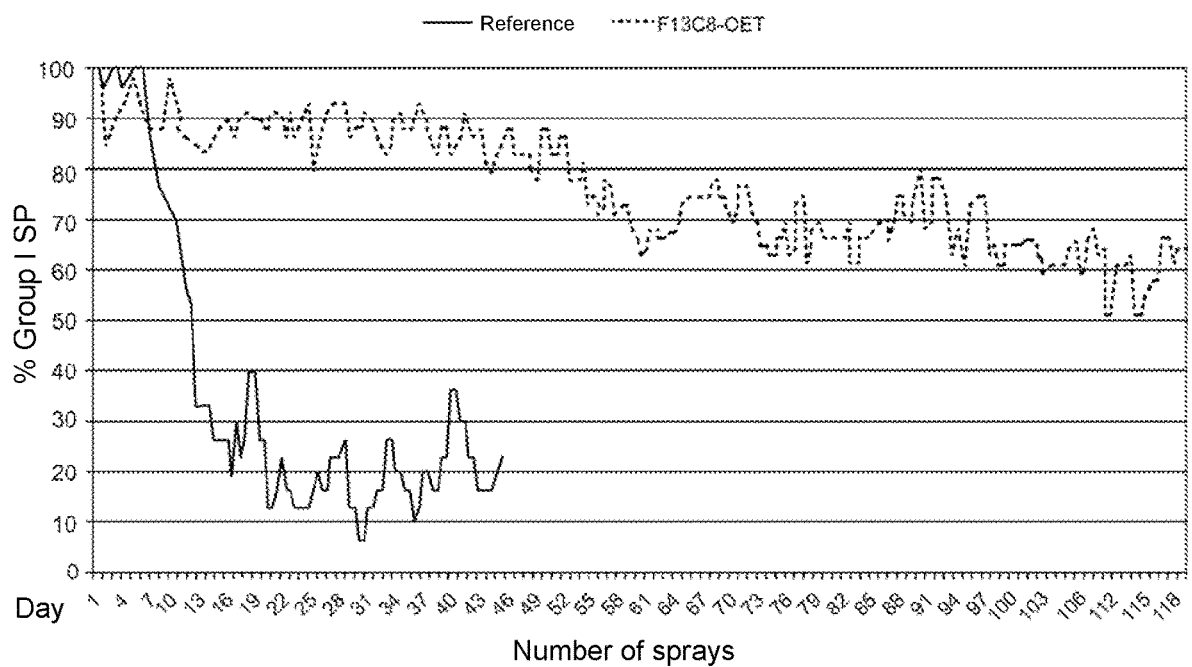
Figure 14:
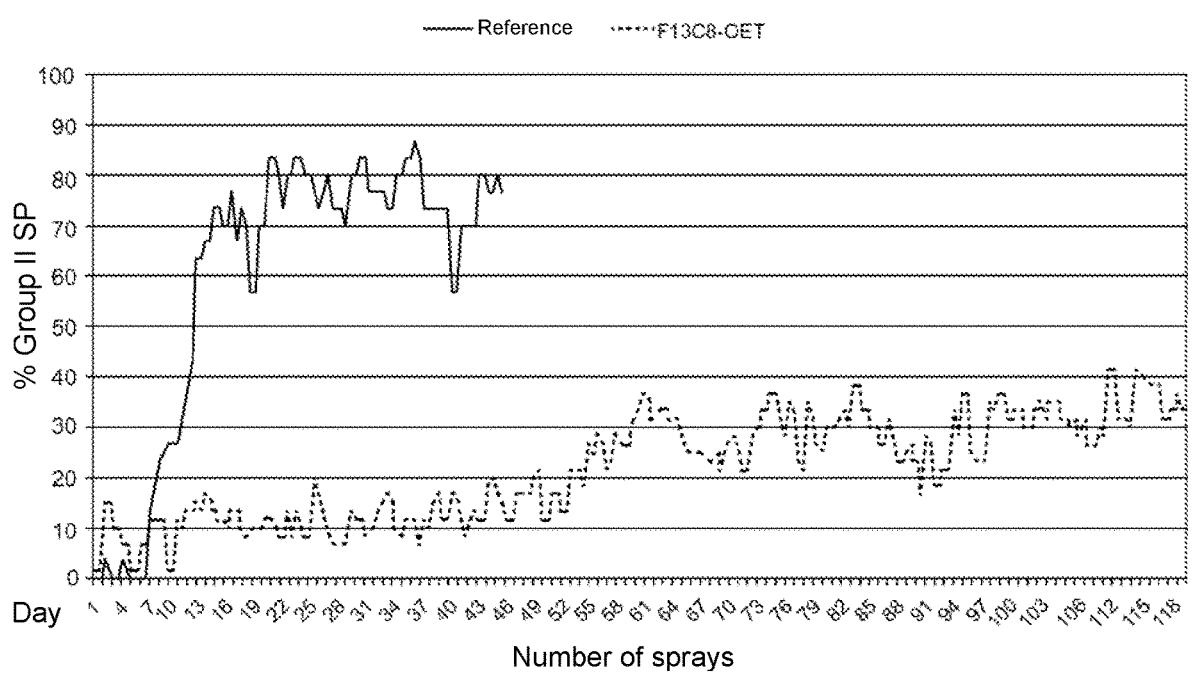
Figure 15:
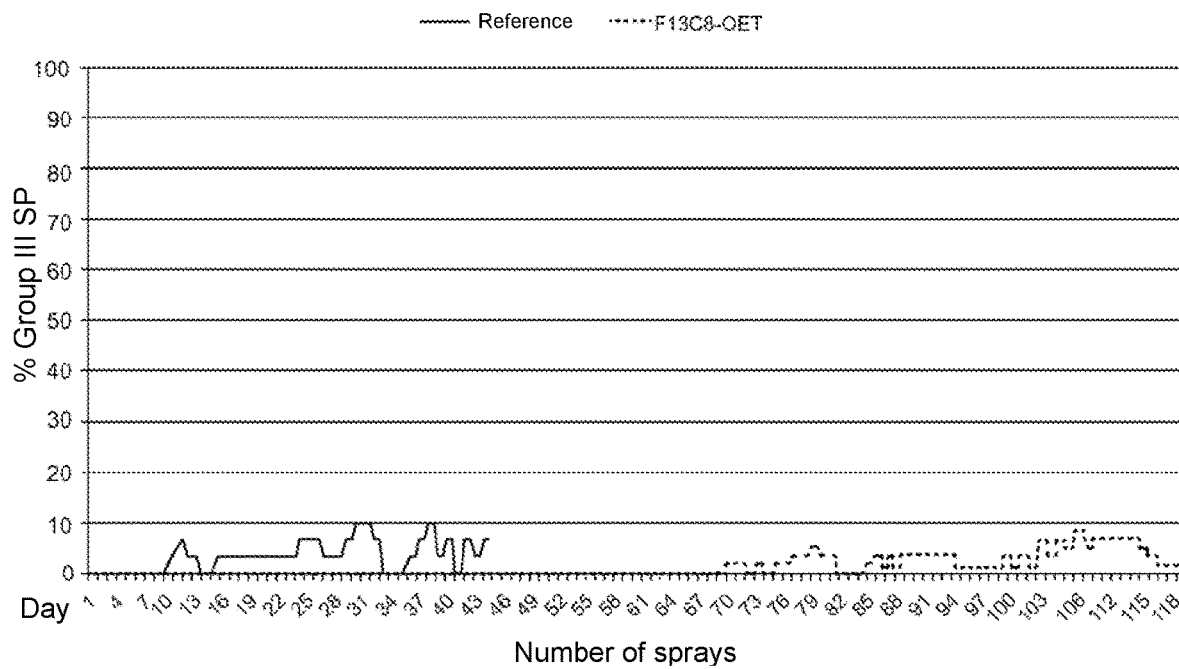
Figure 16:
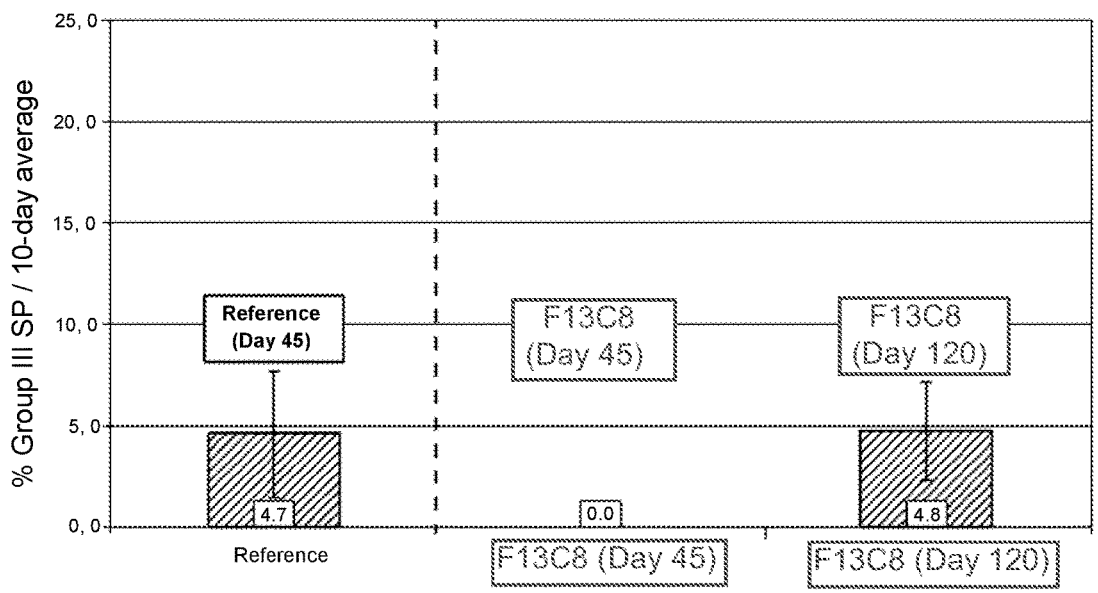
Figure 17:
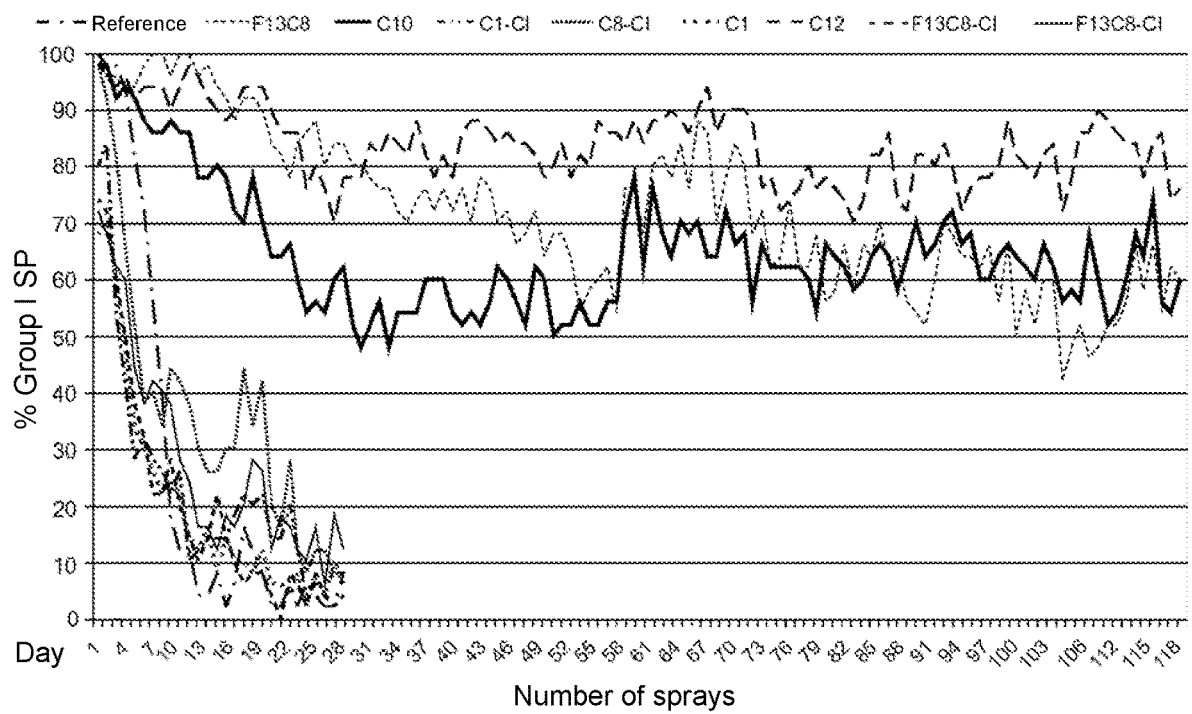
Figure 18:
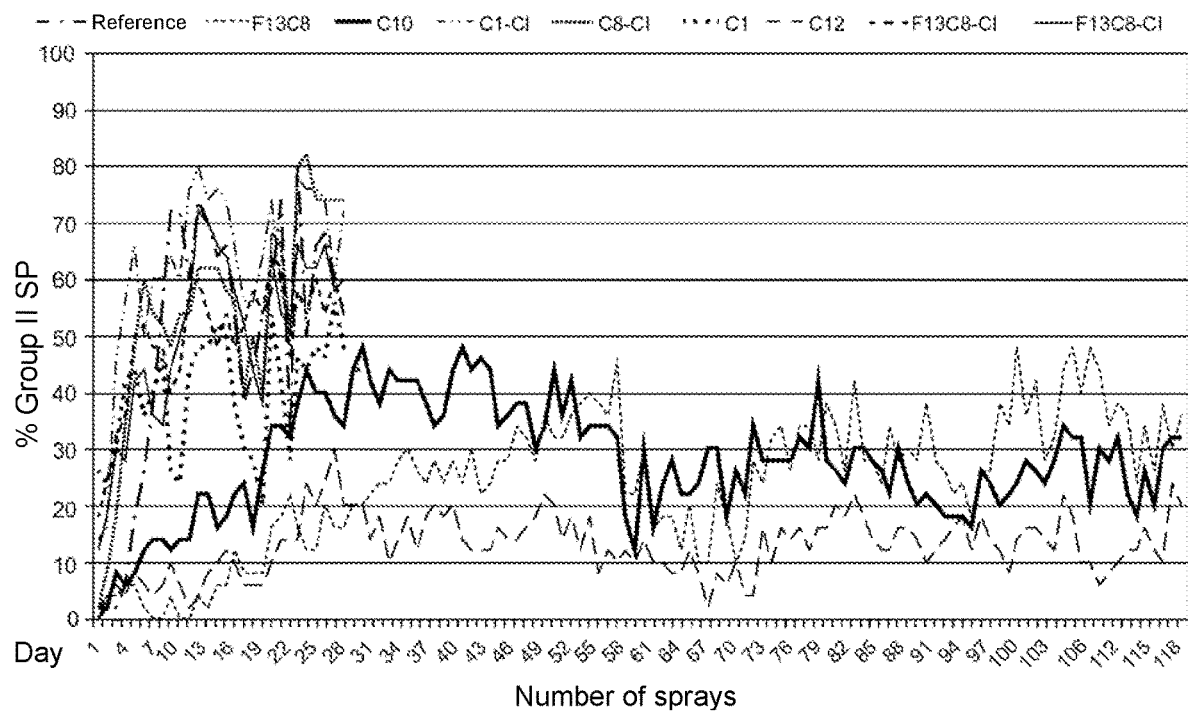
Figure 19:
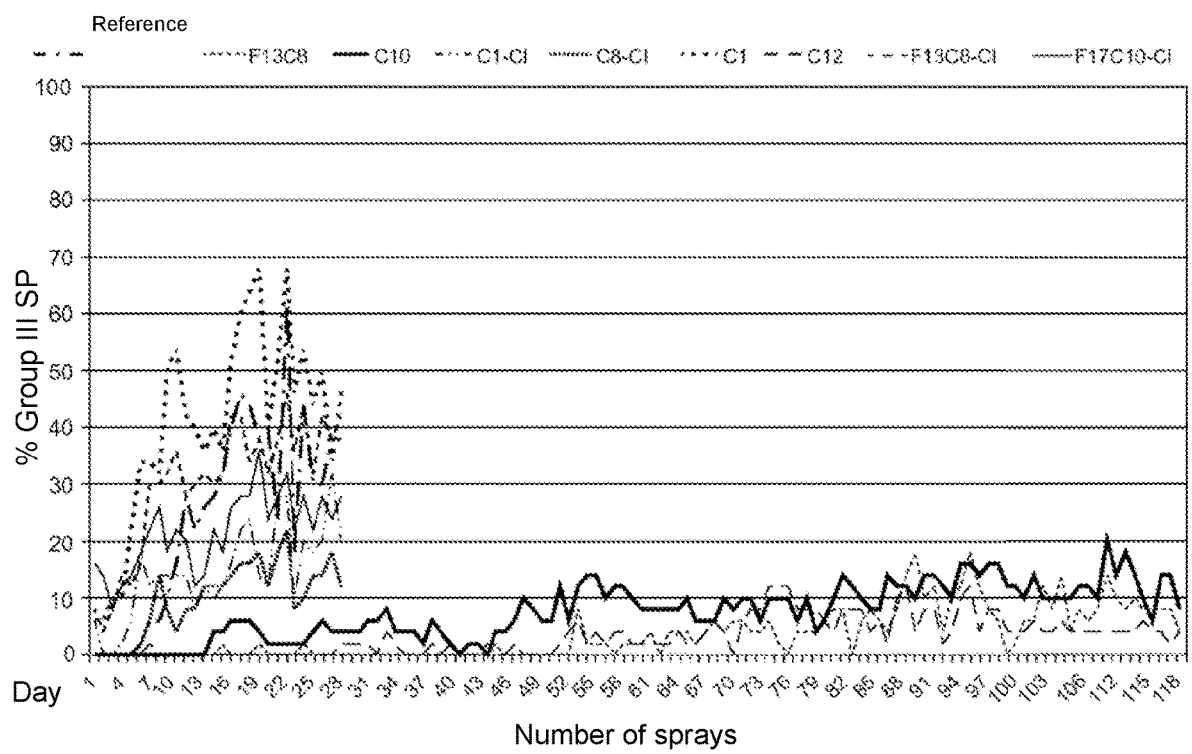
Figure 20:
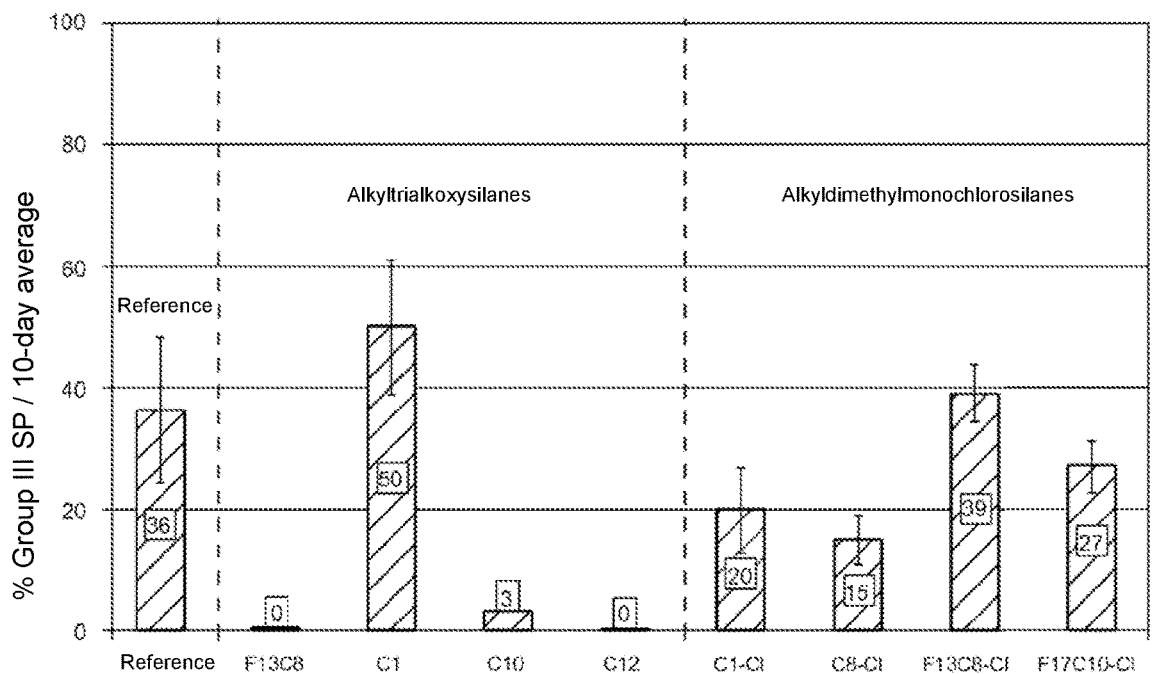
Figure 21:
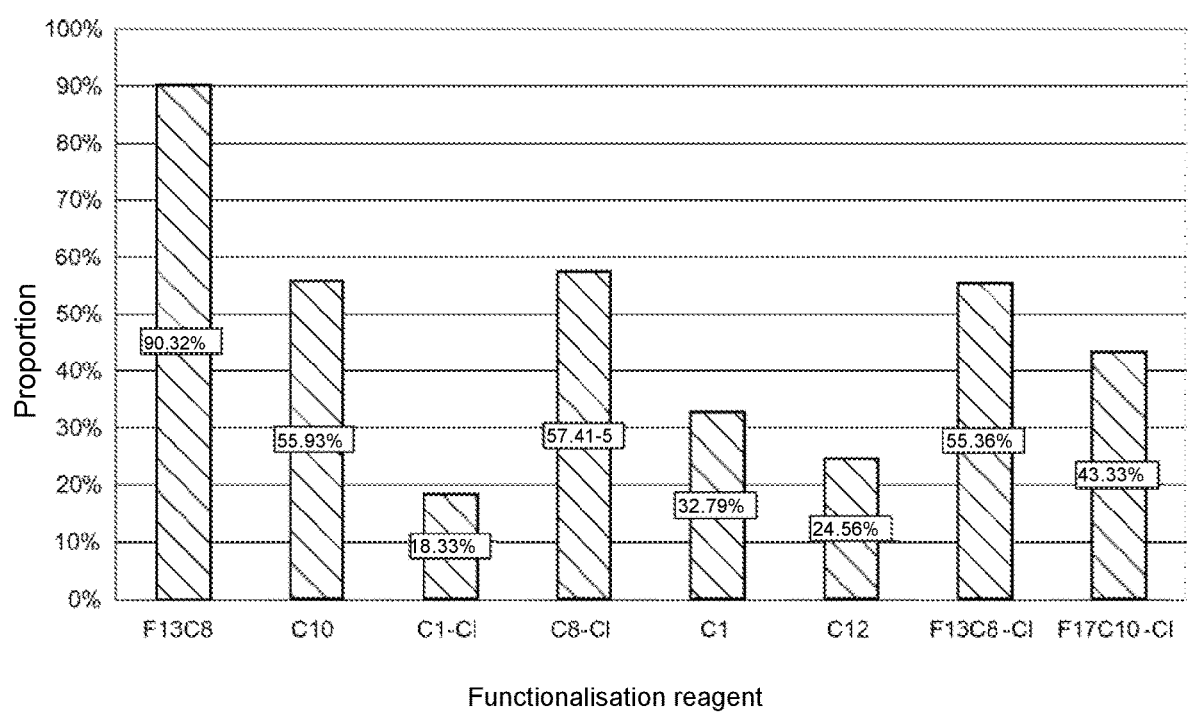

Additional advantages, features, properties and aspects of the present invention are set out in the claims, the embodiments and the following description given on the basis of the drawings, in which:

FIG. 1 is a schematic view of a microstructured component showing an illustration of the microstructure including the outlet openings and the channels leading to the outlet openings, FIG. 2 shows a cut-out of the microstructured component shown in FIG. 1, in which the region of the microstructured component around the outlet openings is shown in detail and the coating is visible, FIG. 3 is a schematic section through a discharge apparatus, in particular an atomiser, in the non-tensioned state, FIG. 4 is a schematic section through the discharge apparatus, in particular the atomiser, from FIG. 1 in the tensioned state, rotated through 90° compared with FIG. 3, FIG. 5 shows an example group I spray pattern (image in two different perspectives) for the tested inhalers comprising a DJI nozzle, FIG. 6 shows an example group II spray pattern (image in two different perspectives) for the tested inhalers comprising a DJI nozzle, FIG. 7 shows the change over time in group III spray patterns for inhalers comprising a DJI nozzle that has uncoated nozzle bodies, according to pH, FIG. 8 shows the 10-day average rate of group III spray patterns for inhalers comprising a DJI nozzle that has uncoated nozzle bodies, according to pH, FIG. 9 shows the change over time in group I spray patterns for inhalers comprising a DJI nozzle that has coated nozzle bodies, according to the modifier, FIG. 10 shows the change over time in group II spray patterns for inhalers comprising a DJI nozzle that has coated nozzle bodies, according to the modifier, FIG. 11 shows the change over time in group III spray patterns for inhalers comprising a DJI nozzle that has coated nozzle bodies, according to the modifier, FIG. 12 shows the 10-day average rate of group III spray patterns for inhalers comprising a DJI nozzle that has coated nozzle bodies, according to the modifier, FIG. 13 shows the change over time during long-duration tests in group I spray patterns for inhalers comprising a DJI nozzle that has nozzle bodies coated with 1H,1H,2H,2H-tridecafluorooctyltriethoxysilane (F1308-OET) compared with inhalers having uncoated nozzle bodies, FIG. 14 shows the change over time during long-duration tests in group II spray patterns for inhalers having a DJI nozzle that has nozzle bodies coated with 1H,1H,2H,2H-tridecafluorooctyltriethoxysilane (F1308-OET) compared with inhalers having uncoated nozzle bodies, FIG. 15 shows the change over time during long-duration tests in group III spray patterns for inhalers having a DJI nozzle that has nozzle bodies coated with 1H,1H,2H,2H-tridecafluorooctyltriethoxysilane (F1308-OET) compared with inhalers having uncoated nozzle bodies, FIG. 16 shows the 10-day average during long-duration tests of group III spray patterns for inhalers having a DJI nozzle that has nozzle bodies coated with 1H,1H,2H,2H-tridecafluorooctyltriethoxysilane (F1308-OET) compared with inhalers having uncoated nozzle bodies, FIG. 17 shows the change over time in group I spray patterns for inhalers having a DJI nozzle that has coated nozzle bodies, for other modifiers, FIG. 18 shows the change over time in group II spray patterns for inhalers having a DJI nozzle that has coated nozzle bodies, for other modifiers, FIG. 19 shows the change over time in group III spray patterns for inhalers having a DJI nozzle that has coated nozzle bodies, for other modifiers, FIG. 20 shows the 10-day average rate of group III spray patterns for inhalers having a DJI nozzle that has coated nozzle bodies, for other modifiers, FIG. 21 shows the yield of category I nozzle bodies depending on the selected modifier.

In the drawings, the same reference numerals are used for like or similar parts, matching or similar properties and advantages being obtained even is the description is not repeated.

FIG. 1 is a schematic view of a microstructured component 1 according to the invention, in particular a nozzle body. The illustration in FIG. 1 shows the microstructure of a nozzle body comprising a DJI-type nozzle, as preferably used in an SMI-type inhaler. The nozzle body is preferably a microfluidic sandwich system and consists of a square microstructured silicon chip that is bonded to a 0.5 mm thick, preferably very smooth glass plate (e.g. a glass produced using the "float" method, preferably based on borosilicate).

The microstructured component 1 consists of two rigidly interconnected plate-like materials, preferably a silicon wafer and a glass wafer. The component 1 has inlet openings 2 and outlet openings 3 for receiving or discharging preferably pressurised fluids, preferably liquids. Channels 4 that are preferably oriented towards one another adjoin the outlet openings. The channels 4 and outlet openings 3 have either a round or non-round shape, in particular preferably an angular cross section of a diameter or depth of from 2 to 10 μm and a width of from 5 to 15 μm, in particular a depth of from 4.5 to 6.5 μm and a width of from 7 to 9 μm.

The microstructures in the silicon chip are preferably produced using etching techniques. The etching depth on the silicon chip can vary depending on the solvent or dispersion medium or method used. Preferably, the depth is 5.6 μm for nozzle bodies intended for atomising aqueous formulations, or 7.0 μm for those intended for atomising ethanolic formulations, as determined by the different physico-chemical properties of the solutions or dispersions. The overall cross-sectional surface area of the outlet openings 3 is usually from 30 to 500 μm, a cross section range of from 30 to 200 μm being preferred. The outlet channels 4 preferably have a length of 40 μm and a width of 8 μm.

In a component 1 having at least two outlet openings 3, the jet directions can be inclined relative to one another at an angle of from 50 to 130°; preferably, an angle of from 70 to 110°, from 85 to 95°, or most preferably of 90°, is obtained. The outlet openings 3 are generally spaced apart by 10 to 200 μm, in particular by 10 to 100 μm, preferably by 30 to 70 μm. Preferably, the spacing between the outlet openings 3 is 50 μm. The jet directions meet one another close to the nozzle openings (preferably at a distance of less than 1 mm, preferably of less than 100 μm, from the surface of the nozzle body) and the fluid is atomised by the liquid jets colliding.

In the following, a preferred embodiment will be described in which the microstructures defined by the inlet openings 2, the outlet openings 3 and the channels 4 are made in the surface of a silicon wafer. The microstructures can be made in the silicon wafer by any suitable method; however, the microstructuring is preferably made by etching methods, as known for example from semiconductor technology. To create surfaces within the microstructured component 1 that are suitable for receiving and subsequently dispensing pressurised fluids, the microstructures are made in one of the materials, preferably the silicon wafer, of the component and connected to the second component, preferably a glass wafer. In this way, cavities in the form of microstructures can be obtained in the microstructured component.

A fine filter 5 consisting of a multiplicity of filter channels can be arranged between the outlet openings 3 or channels 4. The passages or filter channels in the filter structure within the fine filter 5 are selected such that, as far as possible, even the smallest of impurities cannot enter the region of the outlet openings, i.e. the nozzle region, and clog them or change the geometry. The diameter of the filter channels or filter passages is usually from 0.5 to 20 μm, preferably from 2 to 5 μm. The fine filter 5 usually has a zigzag arrangement to increase the surface area. Particles that are larger than the cross sections of the filter channels can be retained in the fine filter 5 to prevent the outlet channels becoming clogged. The filter channels in the filters of the fine filter 5 are formed by protrusions that are preferably arranged in a zigzag shape so as to increase the filter surface area. For example, at least two rows of protrusions form a zigzag configuration. A plurality of rows of protrusions can also be formed, the rows preferably abutting one another at acute angles and forming the zigzag configuration. In embodiments such as this, the inlet and outlet can comprise an inflow region for unfiltered fluid and an outflow region for filtered fluid, respectively, the inflow region and outflow region being substantially exactly as wide as the filter 5 and substantially as high as the protrusions for the inlet and outlet sides of the filter 5. The zigzag configuration formed by at least two rows of protrusions preferably has a tilt angle of from 20 to 250°. Further details on this component design can be found in WO 94/07607 A1.

The microstructured component 1 can comprise an outflow region or a plenary chamber 6. In particular, the plenary chamber 6 is arranged between the outlet openings 3 or channels 4 and the fine filter 5. The plenary chamber can comprise column structures 7 depending on the application. By means of the column structures 7 in the plenary chamber 6, a multiplicity of channels are produced and preferably run into the channels 4 of the outlet openings 3.

The microstructured component 1 or nozzle body forms a rigid system designed to make two liquid jets impact against one another once they exit the outlet openings 3. When the impact is correct, an impact disc forms, at the boundary of which the fine aerosol is produced. The critical parameters for aerosol formation include, inter alia, the flow rate (around 100 m/s) and the angle of impact. Material deposited in the nozzle channels can thus noticeably affect the aerosol formation, for example by deflecting the jet, and cause "spray anomalies", which could even prevent the spray cloud from appearing due to jet divergency.

The surfaces of the microstructured component 1 have a coating 8 which determines the surface properties of the microstructured component. In this regard, both the inner and outer surfaces of the microstructured component 1 can be coated. Preferably, at least the inner surfaces of the microstructured component are coated in order to prevent particles adhering thereto and to thus prevent the nozzle becoming blocked or clogged.

According to a preferred embodiment of the present invention, the outer surface of the component 1 is also modified or coated at least in the region of the outlet openings.

FIGS. 3 and 4 are schematic views of a discharge apparatus according to the invention in the form of a manually operated medical device. The discharge apparatus according to FIGS. 3 and 4 is preferably a propellant-free atomiser 9 that discharges predetermined amounts of a liquid or a liquid medicinal formulation as a preferably respirable or inhalable aerosol 11 per actuation cycle. Aerosol droplets having an aerodynamic diameter of from 0.5 to 5 μm can be inhaled by a user. The average aerodynamic droplet size of the aerosol 11 is preferably within a diameter range of from 0.5 to 10 μm, in particular in the range of from 0.5 to 5 μm.

For the atomisation, a suitable nozzle in the form of the microstructured component 1 according to the invention is used. When operating the atomiser 9, a distinction is drawn between the "non-tensioned state", where the metering volume in the pressure chamber 12 is empty (FIG. 3), and the "tensioned state", where the pressure chamber 12 is full (FIG. 4). When the atomiser 9 is tensioned, the upper housing part 13 is rotated by a fixed angle of rotation, e.g. 180°, relative to the inner housing part 14 and the lower housing part 15. By means of an internal screw thread mechanism, the relative rotation drives a plunger pump such that a predetermined, optionally adjustable amount of liquid 10 is conveyed out of the container 16 into the pressure chamber 12 while the mainspring 17 of the pressure generator 18 is tensioned at the same time (the final state of the tensioning process is shown in FIG. 4). When the atomiser 9 is triggered, i.e. when a locking ring 19 is actuated by means of a button 20, the energy from the pressure generator 18 stored in the mainspring 17 is released. The tubular piston 21 used previously to convey the liquid then pushes into the pressure chamber 12 while the return valve 22 is closed, such that the amount of liquid predetermined by the stroke movement of the tubular piston 21 is discharged from said chamber through the outlet opening 3. The apparatus is now back in the non-tensioned state, as shown in FIG. 3.

In the embodiment shown, by means of the container 16, the tubular piston 21 is rigidly connected, e.g. integrally moulded, glued or snapped on, to a mount 23 belonging to the pressure generator 18. The container 16 is secured, in particular clamped or latched, in the atomiser 9 by means of the mount 23 such that the tubular piston 21 enters the fluid chamber of the container 16 and/or is in fluid communication with the liquid 10 in the container 16 and said liquid can be sucked up via the tubular piston. The container can optionally be replaceable. For this purpose, the device housing can be designed such that it can be opened or partly removed (e.g. in the form of a cap-like lower housing part as disclosed in WO 07/123381 A1).

The container 16 used in the atomiser 9, which is equipped with a dose indicator or meter 24, is designed for removing a plurality of dosage units. For this purpose, the container has to be designed such that the internal pressure remains substantially the same, even during liquid removal, to ensure the same amount of liquid 10 is always removed during suction. For this purpose, it is possible in principle to use both a container 16 that comprise a rigid container wall, the internal pressure of which is kept constant by means of ventilation and which is in turn described for example in WO 06/136426 A1, and a container 16 having a flexible wall that is slid into the container interior at least in part when liquid is removed in such a way that the reduction in the internal volume keeps the internal pressure constant.

Containers 16 in which the flexible wall is formed by a substantially deformable, collapsible and/or contractable pouch are preferred in this case. Various embodiments of containers of this kind are described in documents WO 00/49988 A2, WO 01/076849 A1, WO 99/43571 A1, WO 09/115200 A1 and WO 09/103510 A1. Particularly preferably, the container 16 consists of a flexible multi-layer film pouch that is closed at the bottom and is directly connected in its upper region to a supporting flange, preferably made of plastics material, a container cap welded thereon for connecting to the mount 23 of the atomiser 9, an outer protective sleeve and a top seal (for details see WO 99/43571 A1 and WO 09/115200 A1). The typical filling volume of a container 16 consists of from 3.0 to 3.6 ml of inhalation solution.

A filter system 25 upstream of the microstructured component 1 can be located in the liquid outlet region of the pressure chamber 12. This filter system 25 preferably consists of a plurality of filter components that are arranged one behind the other and differ from one another in particular on account of the filter technology used. The filter thresholds of the individual filter components are of such a level that each filter lets through smaller particles than the one behind it in accordance with the largest exchange principle. By combining different filter techniques and arranging filters to have a gradually increasing degree of separation or gradually decreasing pore sizes, it is possible to achieve a high filter capacity, i.e. the precipitation of relatively large amounts of particles without the filter becoming blocked, and thorough filtering. In addition to collecting solid particles of a particular size, the filter can optionally collect additional material via adsorption. For this purpose, filters of different structures and different materials can be used, such that the adsorption properties are different from filter to filter. Accordingly, combining different filters makes it possible to catch even more particles and in particular particles that can deform under pressure owing to the various adsorption effects. For further details on preferred filter systems, reference is made in particular to WO 2012/007315.

The entire system consisting of the pressure generator 18, having the mainspring 17, and the microstructured component 1 is preferably constructed such that, when the spray mist is produced, not only are respirable droplet sizes formed, but also the spray mist cloud itself remains there for enough time to allow the patient to adapt their inhalation thereto in a simple manner. Preferably, spray times are from 0.5 to 2 s, in particular from 1 to 2 s. The pressure at which the fluid, in particular the liquid drug, leaves the outlet openings is from 50 to 1,000 bar, in particular from 200 to 600 bar.

Depending on the size of the components and the liquid formulation to be atomised, the aerosol 11 contains a distinctively high fine particle fraction (in this case: the fraction of the spray made up by particles having diameters of 5 μm) of for example ≥50%, preferably ≥65%, particularly preferably of 80%, in particular for ethanolic formulations, and the spray cloud produced is preferably slower than in other portable inhalers, e.g. MDI-type inhalers. This leads to significantly higher deposition in the lungs than in other conventional inhalers, such as pMDIs or DPIs. In addition, the atomiser 9 according to the invention is distinguished by a remarkably long duration of spray, which enables good patient coordination in terms of them triggering the atomiser 9 or inhaler.

Depending on the required daily dosage and the intended period of application, the atomiser 9 can be designed to dispense from 10 to 200, in particular from 20 to 150, preferably from 60 to 130 sprays. A slide on the meter 24 indicates how many strokes have been consumed or how many are left. After the specific stroke number is reached, the discharge apparatus preferably locks itself automatically and is blocked from being used further. A "tail-off", as can be noted in metering aerosols that use compressed air, is thus prevented.

To prepare the atomiser 9 for application, a container 16, in particular in the form of a cartridge, must first be inserted. For this purpose, the lower housing part 15 has to be removed. After the container has been inserted, the removed lower housing part 15 is placed back on and the device is primed by being actuated a number of times (=discharging the air from the system). Only after this time is the atomiser 9 ready for operation and can guarantee constant dispensing of a dosage.

The aim of the priming is to completely fill the metering chamber or pressure chamber 12. When the device is actuated while the mouthpiece is oriented vertically upwards, the lower housing part 15 is rotated towards the upper housing part 18 by 180° until the audible clicking and latching. In the process, the mainspring 17 is tensioned, the button 20 springs forwards when latching is complete and indicates that the atomiser 9 is in the tensioned state by sitting flush with the sides. Pressing the button 20 generates the aerosol; the position of the atomiser 9 can be freely selected.

Embodiments

1. Methods Used and Experiment Set-Up

For the following tests, the surfaces of planar substrates made of silicon and glass, and a microstructured nozzle system were modified and their properties studied. Commercially available glass planar substrates produced from borosilicate glass using the "float" method were primarily used as planar substrates for the tests described below. Nozzle bodies having microstructures according to the drawing in FIG. 1 were used as the microstructured nozzle system.

Si/glass planar substrates consist of the same materials as the nozzle bodies and are cut to size from the nozzle body starting materials, i.e. a glass wafer (borosilicate glass having a smooth surface according to the "float" method) and a silicon wafer (111). Their size is that of a conventional microscope slide (26 mm×75 mm) and they are used as a reference material since the nozzle body used is difficult to access for many characterisation tests.

The nozzle body used for the following tests is a microfluidic sandwich system, consisting of a 2.05×2.55 mm$^2$ microstructured silicon chip bonded to a 0.5 mm-thick glass plate (in this case a borosilicate glass produced using the "float" method). The internal microstructure of the nozzle body used consists of an inlet region having an inlet opening, a zigzagged fine filter, a columnar microstructure 7 and the front nozzle region. The etching depth on the silicon chip is 7.0 µm. The distance between the two outlet openings 3 is 50 µm.

During the triggering, a liquid solution or dispersion flows through the inlet region into the microstructure under very high pressure. In the zigzagged fine filter, the fine filter structures having an opening width of 3 µm retain relatively large particles to prevent the outlet channels becoming clogged by such relatively large particles. The outlet channels have a length of 40 µm and a width of 8 µm. The inhalation solution leaves the nozzle body through the two front nozzle outlet channels. The aerosol is generated outside the nozzle body by the two liquid jets produced impacting against one another.

The structure of the nozzle body forms a rigid system that ensures the two liquid jets impact against one another correctly. After having exited the nozzle channels, the two liquid jets collide at an angle of 90° to each other. When the impact is correct, an impact disc forms, at the boundary surface of which the fine aerosol is produced. The critical parameters for aerosol formation include the flow rate (around 100 m/s) and the angle of impact.

As part of the tests described here, when fitted the functioning of the surface-modified nozzle bodies is checked on the basis of SMI atomisers as designed according to FIGS. 3 and 4.

1.1. Preparing Surface-Functionalised Nozzle Bodies and Si/Glass Planar Substrates by Means of Solution Coating The coating process begins by activating the silicon or glass surfaces. The activation cleans the surface of adherent dirt and increases the number of free reactive silanol groups on the surface by means of oxidation. The reactive silanol groups on the surface are capable of reacting with functional silanes. Tests were carried out on modification reagents based on various chloroalkylsilanes and alkylalkoxysilanes, which form a robust siloxane scaffold on the surface following the reaction.

The quality of the surface coating on Si/glass planar substrates is determined by means of contact angle measurement and layer thickness measurement using spectroscopic ellipsometry. For the microstructure or nozzle body, the capillary action test can be carried out.

1.1.1 Preparing the Nozzle Body Sample

The nozzle bodies are functionalised in PEEK trays. PEEK (polyether ether ketone) is a very inert material and is exceptionally suitable for this application. Nozzle bodies have to be functionalised in trays because the very small nozzle bodies would otherwise not be able to be handled in the process tanks. The tray has a reaction chamber that has space for around 50 to 75 nozzle bodies and can be closed by means of a lid. In addition, an agitator that ensures the chamber is thoroughly mixed can be positioned below the reaction chamber. Both the lid and the reaction chamber are provided with small pores, such that solution can flow through the chamber.

Before coating, the nozzle bodies are transported into the reaction chamber by means of a vacuum cup. Since the nozzle bodies have already been cleaned, no special cleaning steps have to be carried out on the component, as is the case for silicon or glass planar substrates.

1.1.2 Preparing the Planar Substrate Samples

The silicon and glass planar substrates do not undergo the cleaning steps like the nozzle bodies, so they have to be thoroughly cleaned again using water and isopropanol prior to being activated. The substrates are cut to the conventional slide dimensions and are also coated in an inert tray having space for around 20 substrates. The Si substrates must have been stripped as close to the functionalisation as possible, i.e. should undergo an HF treatment; this ensures a uniform $SiO_2$ film on the surface. When the silicon substrates are stripped, the natural oxide layer on the surface is removed. After this removal, the oxide film regrows slowly and generates a uniform thin oxide film.

For the stripping, a 6% hydrogen fluoride solution is used, in which the silicon substrates should remain for at least 20 minutes. Following the removal therefrom, the Si substrates are thoroughly rinsed with water and sorted into the substrate trays for coating.

The glass substrates used have a fire-polished side and an extra-smooth side produced in the float method. To improve the reproducibility of the measurement results in the tests described here, the fire-polished side of the glass substrates was marked using a diamond scriber before the start of the process. This is the side on which the ellipsometric measurements will be taken later in the process.

1.1.3 Overview of the Surface Functionalisation Process Steps

The process begins by cleaning the surfaces of adherent dirt. Next, the cleaned surface is oxidatively activated. After a rinsing step in which the activation solution is washed off the nozzle bodies or substrates, the actual coating process can begin. If the coating is carried is carried out using an alkyltrialkoxysilane, the coating reagent has to be transformed into the active silanol component by means of precursor splitting. After coating, the samples are dried and then dried in an oven at 120° C.

1.1.3.1 Cleaning and Activating Nozzle Bodies and Si/Glass Planar Substrates

The coating process usually begins by cleaning and activating the silicon or glass surfaces. The samples are cleaned and activated in one operation. The following cleaning and activation solutions are used for nozzle bodies and Si/glass planar substrates in the following tests.

1.1.3.1.1 NaOH Solution (Highly Alkaline Activation)

The samples are added to 25% caustic soda and stirred. Next, they are thoroughly rinsed with lots of water. In most cases, the method works very well, but relatively often leads to clouding on the glass or silicon surface since the surface has already been etched (glass corrosion). In the following, therefore, this method is only used for preliminary tests since clouding on the nozzle body is unacceptable due to the visual quality control.

1.1.3.1.2 RCA Solution (RCA=Radio Corporation of America)

The next activation solution, referred to as RCA solution, is Standard Clean 1 solution (SC-1 solution), which was developed for the RCA method in order to clean silicon wafers. The samples are added to a solution of $H_2O$:$NH_3$ (aq. 25%):$H_2O_2$ (aq. 30%) in a volume-to-volume ratio of 5:1:1 at 70° C. and stirred. The Si/glass substrates are stirred constantly for 20 minutes, whereas nozzle bodies are treated for one hour alternating between treatment with ultrasound (20 minutes each time) and stirring (10 minutes each time). Next, the substrates or nozzle bodies are thoroughly rinsed with water. The substrates or nozzle bodies are stored in water until the start of the process.

1.1.3.1.3 Piranha Solution (Acidic Oxidative Activation)

The samples are added to a solution of $H_2SO_4$ (conc.): $H_2O_2$ (aq. 30%) in a volume-to-volume ratio of 7:3 at 70° C. and stirred. The Si/glass substrates are stirred constantly for 20 minutes, whereas nozzle bodies are treated for one hour alternating between treatment with ultrasonic waves (20 minutes each time) and stirring (10 minutes each time). Next, the samples are thoroughly rinsed with water and can be stored in water until coating.

1.1.3.2 Surface Functionalisation of Silicon and Glass Surfaces Using Alkyltrialkoxysilanes The trialkoxysilanes are added to an alcoholic solution and, since they are a precursor compound, have to first be proteolytically split into the active silanol components. By way of example, this reaction can be taken from equation 1 below. The silanol compound is usually produced within five hours, as indicated in equation 1 for the example 1H,1H,2H,2H-tridecafluorooctyltriethoxysilane (example substance used: Dynasylan® F8261 from Evonik) from the starting compound.

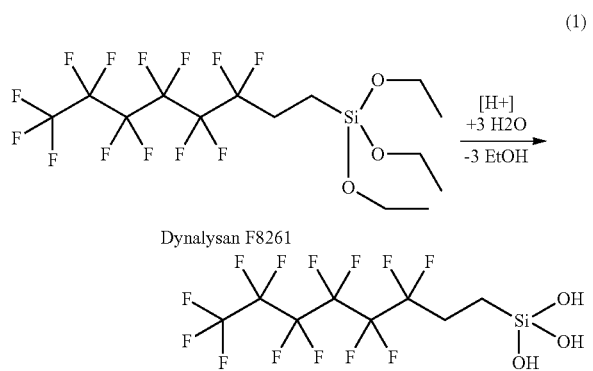

(1)

The active silanol components now associate with the activated surface and bond covalently following tempering.

During the functionalisation, the solution is stirred constantly. Unlike the substrates, nozzle bodies are treated with ultrasound at fixed intervals during the functionalisation. Following functionalisation, the samples are removed from the solution and dried for one hour in air. After drying, the samples are tempered in an oven for 1 hour at 120° C. Following tempering, the substrates are carefully rinsed using a small amount of isopropanol. Nozzle bodies can also be used without any additional cleaning step.

1.1.3.2.1 Surface Coating Process Using Alkyltrialkoxysilanes in an Isopropanol-Water Mixture 1.1.3.2.1.1 Hydrolysis of Starting Compound A 0.1-1.0 vol. % solution of the silane is added to an acidic alcohol-water mixture (2-propanol/$H_2O$/$HCl_{conc}$ 89.8:10:0.2) and stirred at room temperature for at least five hours.

The compound can be used after five hours and must be used up within 24 hours.

1.1.3.2.1.1 Surface Functionalisation

The samples are added to the functionalisation solution and constantly stirred during coating. Nozzle bodies are repeatedly treated with ultrasound at fixed intervals during the coating. After functionalisation, the samples are removed from the liquid, and the tray for the substrates and the tray for the nozzle bodies are passed to a cellulose cloth for drying. The samples are dried for one hour in air.

1.1.3.2.1.2 Condensation

The samples are tempered in an oven at 120° C. Next, the substrates are carefully washed using isopropanol. Nozzle bodies can also be used after tempering without any additional cleaning step. The finished nozzle bodies and substrates can be stored under laboratory conditions.

1.1.3.3 Surface Functionalisation of Silicon and Glass Surfaces Using

Chloroalkylsilanes Surface functionalisation by means of chloroalkylsilanes is based on the condensation reaction between the free silanol group on the surface and the chlorine function of the functional alkylsilane.

Chlorosilanes are very sensitive to moisture and their reactions must be carried out in dry, non-polar solvents such as toluene, tetrachloromethane or alkanes such as hexane.

1.1.3.3.1 Schematic Surface Coating Process Using Alkylchlorosilanes in Toluene

The surface of substrates and nozzle bodies are activated as described above.

1.1.3.3.1.1 Drying the Solvent

The toluene is dried for at least 12 hours using a molecular sieve (type 4 A). The ratio is 10 g molecular sieve to 1 litre solvent.

1.1.3.3.1.2 Surface Functionalisation

The samples are coated in 0.07 to 0.7 mol solutions of the chlorosilane while being stirred constantly. Nozzle bodies are repeatedly treated with ultrasound at fixed intervals during the coating. After functionalisation, the samples are removed from the liquid, and the tray for the substrates and the tray for the nozzle bodies are passed to a cellulose cloth for drying. The samples are dried for one hour in air.

1.1.3.3.1.3 Condensation

After drying, the samples are tempered in an oven at 120° C. Next, the substrates are carefully washed using isopropanol. Nozzle bodies can also be used after tempering without any additional cleaning step. The finished nozzle bodies and substrates can be stored under laboratory conditions.

1.2 Categorising Nozzle Bodies after Coating

The coated nozzle bodies are divided into the following nozzle categories I to IV.

Category I

The nozzle region, the zigzagged filter and the support structure of the nozzle body are as free of residues as possible.

Category II

The nozzle region is free of residues, yet there are some in the zigzagged filter and column structure.

Category III

One nozzle channel contains residues or is completely clogged.

Category IV

Two nozzle channels contain residues or are completely blocked.

1.3. Provocation of Nozzle Blockages in the Nozzle Body 1.3.1 Provocation Solutions Provocation solutions are intended to cause the phenomenon of nozzle blockage or the jet divergency effect as often as possible. Therefore, in terms of their parameters, they are selected such that they will cause a very high number of clogged nozzles during a test. This is necessary in order to cause a sufficient number of clogged nozzle using as few samples as possible to allow meaningful assessments to be made as to whether a modification influences the occurrence of clogged nozzles.

1.3.2 Provocation of Nozzle Blockages During in-Use Operation of an Atomiser Having a DJI Nozzle (=Provocation Tests)

1.3.2.1 the Phenomenon of Nozzle Blockages

In an SMI inhaler having a DJI nozzle, the aerosol production is based on two microfluidic jets impacting against one another. These jets are generated in the nozzle body by two rectangular nozzle outlet channels that are oriented at a 90° angle to one another. For the spray performance, it is critical that the two liquid jets impact against each other correctly. Provoked particle deposits in one or both nozzle channels can disrupt the proper impact by deflecting the jets and can lead to changes in the spray pattern and deviations in the fine particle fraction. In this document, the term "jet divergency" should be understood to mean group III spray patterns, which have an altered fine particle fraction or in which at best only a small portion of the amount of liquid to be discharged by atomiser actuation is actually discharged as an aerosol. A more comprehensive definition of the term is as follows: The phenomenon of jet divergency (jet deflection due to nozzle blockage) is a reversible or permanent, partial or total blockage/clogging of one or both nozzle channels of the nozzle body that has been caused by particles in the inhalation solution and leads to sprays having a different fine particle fraction.

1.3.2.2 Allocating Spray Patterns in Provocation Tests

Provocation tests allow various factors influencing the phenomenon of nozzle blockage to be assessed. The test is designed such as to block as many inhaler nozzles as possible over the duration of the test. For this purpose, the atomisers are triggered once a day and the spray pattern is determined visually. This type of test scenario is referred below as an "in-use test" since it reproduces the daily use of an atomiser by a user, at least in relation to frequency of use.

The spray pattern (SP) of the atomiser is recorded over the entire duration of the test in accordance with the categorisation set out above and is then evaluated. For this, the individual spray patterns are summarised in the three following superordinate groups: Normal ("good") sprays (group I), spray pattern anomalies (group II) and sprays having an altered fine particle fraction (group III=jet divergency). The effect of a test parameter on the incidence can be deduced from comparing it with a reference.

FIG. 5 shows example group I spray patterns. Sprays of this kind have a dominant, undivided spray cloud (with at most just a small amount of side spray). Normally, the spray cloud is symmetrical.

FIG. 6 shows example group II spray patterns. The spray patterns in this group show split spray clouds. FIG. 6 shows a spray cloud split symmetrically, although asymmetrically split spray clouds or sprays split multiple times also belong to this spray pattern group. It should be noted here that detecting the division of the spray cloud may depend on the perspective of the observer. In (automatic) spray cloud image detection, therefore, use is preferably made of two cameras that are arranged at a 90° angle to the aerosol cloud axis and take the images of the aerosol cloud from two different perspectives at the same time as the device is triggered.

Group III spray images, for which the fine particle fraction is considerably different from or less than the group I and II sprays (due to the impaired aerosol formation), cannot be detected using simple image recording systems. However, when special illumination is provided, the liquid exiting the nozzle, e.g. in one or two very thin jets, can be detected visually. In the spray patterns for this group, the liquid jets do not impact against each other due to them being deflected (and so the spray cloud typical of DJI nozzles is not formed). Therefore, jet divergency has occurred.

1.3.2.3 Spray Pattern Assessment

The spray patterns are assessed visually (in a series of tests carried out manually) or by means of camera technology (in series of tests carried out using a stroke robot) and are assessed upon each stroke of the device. The spray pattern detected on the test day is recorded together with the stroke number. In the evaluation, the recorded spray patterns are assigned to the individual groups and the progression of the spray pattern over time is observed.

During a provocation test, the atomiser is mounted in the laboratory at constant temperature and atmospheric humidity. The spray patterns are assessed for all the devices within a test on the same day.

Devices put into operation for the first time have to be primed before the start of the test.

To subsequently assess the spray patterns, the primed device is lifted into a suction apparatus at an angle of 45°. The distance from the suction machine is around 20-30 cm to allow the aerosol cloud to be clearly visible. The contrast can be increased by using black cardboard as a base and a cold light source. The spray patterns are classified according to the aforementioned groups.

The spray patterns can also be assessed in an automated manner using a stroke robot. For this purpose, the robot is fitted with the pre-primed atomiser and a robot arm then coordinates the tensioning and release of the inhaler. Two CCD cameras are oriented at a 90° angle to the aerosol cloud axis and take images of the aerosol cloud at the same time as when the apparatus is triggered. The spray patterns are assessed manually by an employee on the basis of the images recorded.

1.3.3 Test Set-Up for a Standard Provocation Test

The standard test set-up for a provocation test is as follows:

Number of inhalers: 30-150 (depending on the influencing parameters being tested)

In-use mode: 1×1 (1 stroke/day) or 1×2 (2 strokes/day)

Test point: Spray pattern (specification according to spray pattern catalogue)

Duration of test: 28-120 days; similar to 1-month/4-month patient usage

Formulation: Ethanol/water 90/10 (v/v), pH 2.0

Number of references: 30-75

1.3.3.1 10-Day Average and Provocation Reference

The individual spray pattern curves in a provocation test can be subject to large fluctuations over the duration of the test. The number of devices having clogged nozzles is time-dependent and increases linearly after some time, often then reaching a steady state around which the system spreads. Therefore, it is not always possible to determine a precise, final rate. For this reason, in addition to the spray pattern curves, the average rate of group III sprays is determined for each test branch over the last ten days of the test (i.e. the 10-day average rate is determined). The actual scale of the influence of one test parameter on the incidence in group III sprays can only be discovered by comparing it with an internal provocation reference. In this respect, a provocation reference is a group of inhalers that are missing the feature being studied, e.g. nozzle coating. They represent the original state of the device and thus make it possible to draw meaningful conclusions on any modification.

1.4. Instrumental Analytics
1.4.1 Contact Angle Measurement

The quality of the coating on Si/glass planar substrates can be described on the basis of static contact angle measurement. The results give information on the presence and homogeneity of the coating. The contact angle measurements were taken using a commercially available measuring instrument (in this case a DSA 10 MKR from Krûss GmbH) having associated control technology and control software (evaluation according to the Young-Laplace model).

1.4.1.1 Bases

To assess the extent to which a liquid can wet a surface, the contact angle can be used. The contact angle is formed and measured on the solid/liquid/gas phase contact line between the solid and liquid. In this regard, the extent to which a liquid can wet a surface depends on the surface tension ratios between the solid and liquid ($\gamma_{f/fl}$), solid and air ($\sigma_{f/g}$), and liquid and air ($\sigma_{fl/g}$). The boundary surface tensions at the droplet are in an equilibrium that can be expressed by Young equation 2.

$$\sigma_{f/g} = \gamma_{f/fl} + \sigma_{fl/g} \times \cos\theta \qquad (2)$$

The smaller the contact angle, the better the wetting. A contact angle of 0° is referred to as total wetting; in turn, a contact angle of 180° denotes no wetting. The equilibrium described by the Young equation is adjusted according to time and temperature.

1.4.1.2 Static Vs. Dynamic Contact Angle Measurement

Unlike dynamic contact angle measurement, in static contact angle measurement the contact surface between the solid and liquid is not changed during the measurement. On an ideal, chemically and topologically homogeneous solid surface, a pure liquid in a saturated vapour phase would have an identical dynamic and static contact angle. This state is described in the Young equation. However, the contact angle can vary according to time and location. This phenomenon is counteracted by always measuring the contact angle immediately after the placement of the droplet.

1.4.1.3 Description of Contact Angle Measurement

Before each measurement, the coated silicon or glass substrates are freed of adherent dust by means of oil-free air and placed on the sample stage for the measurement. For this purpose, the silicon substrates are positioned with the matte side downwards. By means of an automated microlitre syringe, a droplet having a volume of 8 µl is placed on the substrate and measured immediately using the control software or control program. For all contact angle measurements, double deionised water and/or n-dodecane is used. All contact angle values stated in the document are average values produced generally from the measurement of five droplets. In the process, each droplet is fitted and measured ten times by the control program similarly to the Young-Laplace model. Generally, each coating is carried out using 3-5 substrates, each substrate also being used for contact angle measurement.

1.4.2 Testing Metering Behaviour Using Delivered Mass (DM) and Metered Mass (MM)

The metered dispensing of formulation by an atomiser, i.e. the measured mass of formulation (hereinafter "metered mass" (MM)), is determined by the structural dimensions of the inhaler and the density of the formulation solution. This is the mass of the formulation solution released through the atomiser when it is actuated. The MM is determined gravimetrically.

Generally, a small portion of the measured mass remains on the nozzle as a residue following triggering. This cannot be completely prevented since there is always a backscattering region in the atomisation principle used based on an impact disc formed by two liquid jets. Therefore, the mass actually emitted from the device as a spray cloud (hereinafter "delivered mass" (DM)) is usually smaller than the metered mass (MM). The DM is also determined gravimetrically.

1.4.3 Ellipsometry
1.4.3.1 Apparatus Set-Up

Ellipsometry is a measurement method that was used as early as in the 19th century. Some of the essential components of an ellipsometer have been available for a very long time, whilst other components of modern ellipsometers have only been developed recently.

In spectroscopic ellipsometry (SE), a white light source having a monochromator enables the ellipsometric measurements at different wavelengths. In the process, the monochromator can be positioned upstream of the polariser or downstream of the analyser. There are also spectroscopic ellipsometers having a rotating compensator (cf. Irene, E. A. and H. G. Tompkins, *Handbook of Ellipsometry*, 2005: William Andrew Pub).

The ellipsometric measurements in this document were taken using a spectroscopic ellipsometer having a rotating compensator. More information on the devices used can be found in Table 1.

TABLE 1

| Device used in the ellipsometry. | |
| --- | --- |
| Ellipsometer | Alpha-SE ® having a rotating compensator from J. A. Woollam Co., Inc. (USA) |
| Spectral range | 390-900 nm |
| Angle of incidence | 65°, 70° and 75°, and transmission at 90° |
| Control software | Complete EASE from J. A. Woollam Co., Inc. (USA) |

1.4.3.2 Description of the Ellipsometric Measurements

Before each measurement, the silicon or glass substrates are first freed of adherent dust using oil-free air. Next, the substrates are carefully placed on the sample stage of the ellipsometer using wafer tweezers. Care should be taken to ensure the silicon substrates are positioned with their matte side downwards. In transparent glass substrates (Borofloat® 33, Nexterion), Scotch tape is stuck to the "tin side" before the substrates are positioned on the sample stage. The aforementioned marking scratched into the glass before the coating process using a diamond scriber should be identified.

The "tin side" is stuck down for two reasons. Firstly, rear-side reflections on the transparent glass substrate should be prevented, and secondly, the layer thickness should not be measured on the "float side" of the glass due to the tin residues and because it makes analysis more complicated. The glass used is a float glass, which is poured onto a tin bath during its production, resulting in high levels of tin contamination for a glass side.

After positioning the planar substrates on the sample stage, the stage vacuum can be switched on (better orientation parallel to the plane) and the measurement carried out. Measurements are taken at the angles 65°, 70° and 75°. After the measurement, the raw data is analysed using the corresponding method for silicon or glass by means of the analysis function in the Complete EASE software.

1.4.3.3 Development of an Analysis Method for Layer Thickness Measurement on Silicon and Glass Planar Substrates

1.4.3.3.1 Analysis Model for Silicon Substrates

For the elliptometric measurement of the layer thickness on silicon substrates, the following layer model is assumed: Silicon substrate/native oxide/self-assembled monolayer.

On its surface, silicon forms a native oxide layer; this forms relatively quickly, even after the HF stripping. During the coating, the self-assembled monolayer of the reactive silane compound orients itself on this oxide layer.

This layer model can be modelled using the software (Complete EASE) on the measurement instrument used, provided that the necessary optical constants and layer thicknesses are present. The optical constants for pure silicon and for the native oxide layer are known and are stored in the analysis software database. The optical constants for the SAMs to be generated (when present) are found in the literature or have to be determined by the laboratory itself. To determine the layer thickness of the self-assembled monolayer, the Cauchy dispersion equation in the analysis software is used. This equation describes the refractive index n as a function of wavelength A and is suitable for analysing ultra-thin, transparent, non-absorbent films. The layer thickness of the native oxide layer after RCA treatment was determined by experiment, the aim being a maximum of 1.5 nm.

The test is set-up as follows:
Substrate: two silicon planar substrates per test condition
HF treatment: 20 minutes prior to RCA treatment
RCA treatment [min]: 0, 5, 10, 20, 60, 90

In the standard coating method, the RCA cleaning runs for 60-90 minutes. To measure the layer thickness of the SAMs on Si substrates, therefore, a silicon oxide layer of 1.5 nm has to be used.

It is important to characterise the layer thickness of the native oxide layer in order to later determine the layer thickness of the self-assembled monolayer on Si substrates.

1.4.3.3.2 Analysis Model for Glass Substrates

To measure the layer thickness on glass substrates, the following layer model is assumed: Glass substrate/self-assembled monolayer.

The model does not have an oxide layer, as is the case for silicon substrates. It is assumed that the self-assembled monolayer bonds directly to the glass substrate. In addition to the specific optical constants for the glass used in this case, consideration was also given to how the glass behaves after RCA treatment and the material constants were adjusted accordingly. The glass was input into the software as a material along with its constants such that, when the SAM refraction index is known, the layer thickness can also be determined in this case in accordance with the Cauchy dispersion equation.

1.4.4 Capillary Action Test on Nozzle Bodies

Since the interior of the microstructure is difficult to access for analytical methods, the evidence of whether a nozzle body is coated is gathered from a capillary action test. The test is based on a capillary being spontaneously filled with solvents of different polarities (generally water). The capillary action test makes it possible to check whether a coating is present in just a few seconds. As a polar liquid, water wets the nozzle body surface of an uncoated nozzle body and immediately penetrates the microstructure upon contact with the nozzle body as a result of positive capillary forces (capillary ascension effect). This effect can be tracked under a microscope and does not occur, for example, if a nozzle body is coated to be hydrophobic.

If the hydrophobic coating is successful, the capillary ascension effect does not take place and "capillary depression" is noted. In the case of capillary depression, the cohesion forces between the molecules are greater than the forces of adhesion to the surface. The liquid becomes globular and the surface is not wetted. A liquid that does not wet the capillary surface is expelled from the capillaries when it enters them.

1.4.4.1 Carrying Out the Capillary Action Test

Using PTFE tweezers, a coated nozzle body is oriented under the microscope such that the internal microstructure is clearly visible. Next, a cotton bud (Q-tip) soaked in test liquid is carefully moved close to the intake region of the nozzle body. When the Q-tip comes into contact with the intake structure, the microstructure is not filled with a polar liquid, e.g. water, if the nozzle body is hydrophobed. As a positive check in this case, the test can be repeated using a non-polar substance, e.g. n-dodecane. Here, the filling is successful due to good wetting. In this case, a nozzle body coated with a perfluorinated alkylsilane should in turn be filled with a perfluorinated test liquid, e.g. perfluorooctane.

2. Results

2.1 Parameters Influencing the Spray Performance of Uncoated Nozzle Bodies

When determining a suitable provocation solution, the extent to which different external influences, in particular pH, affect the spray performance of the atomisers under consideration was investigated beforehand. In this respect, for example ethanolic formulations (90/10) of various acidity levels (pH 2.0, 2.4, 2.8, 3.2, 3.5, 5.0) were tested for their likelihood to cause nozzle blockages.

As an example from these preliminary tests, FIG. 7 shows how the jet divergency rate is dependent on the pH of the provocation solution. As can be seen in FIG. 7, pHs 2.0 and 2.4 saw an early, sharp increase in group III sprays. At the end of the test, a value of almost 70% was achieved for pH 2.0 and a value of around 50% for pH 2.4. The two curves show the first group III sprays very early on from day 2. This is contrary to the spray pattern curves for pHs 3.5 and 5.0, in which the proportion is almost 0% at the end of the test. It is not until day 21 that a small number of individual group III sprays occur.

It is very clear from the spray pattern curves that the frequency of a group III spray increases sharply as the pH decreases (from 5.0 to 2.0).

FIG. 8 shows the 10-day average rate (in tests over 28 days) of group III sprays (jet divergency) at the end of the test. As the pH increases, the number of group III sprays decreases. Therefore, the pH of the inhalation solution has a significant proportion of blocked/clogged nozzles. The lower the pH of the inhalation solution in the range tested here, the more frequent the deviations from a group I spray ("good spray").

Overall, a suitable provocation solution was determined from the preliminary investigations: Ethanol/water solution in a volume-to-volume ratio of 90:10, made acidic using HCl at pH of ≤2.0 (no active ingredient added).

2.2 Functionalisation of Planar Substrates and Nozzle Bodies

2.2.1 Functionalisation of Silicon and Glass Substrates

2.2.1.1 Impact of Activation

To determine a suitable coating process for simultaneously coating silicon and glass, various influencing factors have to be investigated. The actual activation of the silicon and glass surfaces plays a key role in this respect since it specifically ensures sufficient stability of the coating.

In one test, the effect of different activations on the properties of the resultant coating was investigated. Silicon and glass planar substrates were coated simultaneously under the same conditions using the four different activation methods (piranha solution, RCA solution and NaOH solution). They were then functionalised using 1H,1H,2H,2H-tridecafluorooctyltriethoxysilane (c=0.003 mol/l). Suitable 1H,1H,2H,2H-tridecafluorooctyltriethoxysilane is sold, for example, by Evonik under the name Dynasylan® F8216. After coating, the substrates were washed using 2-propanol and the static water contact angle was then measured. The aim was to obtain a set of parameters for each activation that can be used to obtain water contact angles for each activation solution of more than 100° after coating. A water contact angle of more than 100° indicates a homogeneous, all-over coating and good hydrophobicity.

It was found that all the activations tested could be used to successfully coat silicon/glass planar substrates and to obtain contact angles of more than 100°.

However, it was also found that the NaOH activation method was only suitable for the coating process to a limited extent since it frequently causes clouding on the glass. This phenomenon is also known as glass corrosion. For this reason, the NaOH activation was intended for preliminary tests only, not for the subsequent tests on the nozzle body. For the quality check on the DJI nozzles produced, it is desirable to always be able to view the nozzles under a microscope. If the glass component of the nozzle body were cloudy, this would no longer be possible.

2.2.1.1 Effect of Coating Reagent Concentration

The impact of the coating concentration on the water contact angle on silicon/glass planar substrates was analysed. For this purpose, the silicon/glass planar substrates were coated with a short-chain alkylalkoxysilane (methyltrimethoxysilane=MTMS). To analyse the effect of the coating concentration, the concentration was gradually increased. Then, the substrates were characterised using static water contact angle measurement.

The silicon and glass planar substrates were coated in a similar manner to the description according to section 1.1. They were activated using an RCA activation for 20 minutes at 75° C. The substrates were coated for two hours without ultrasound at room temperature using the functionalisation reagent methyltrimethoxysilane (abcr GmbH, Karlsruhe, Germany) at various substance concentrations from 0.7 mmol/l to 70 mmol/l. Next, the substrates were dried for one hour at room temperature and lastly tempered in an oven for one hour at 120° C. The test results are shown in Tables 2 and 3 below.

TABLE 2

Water contact angle (with standard deviation d) of glass planar substrates coated with MTMS according to MTMS concentration

| MTMS concentration [mmol/l] | Contact angle [°] | d [°] |
|---|---|---|
| 0.7 | 67.11 | 12.45 |
| 3.5 | 87.45 | 6.03 |
| 7 | 78.32 | 4.47 |
| 14 | 83.60 | 8.13 |
| 35 | 97.39 | 8.46 |
| 70 | 103.22 | 2.68 |

TABLE 3

Water contact angle (with standard deviation d) of silicon planar substrates coated with MTMS according to MTMS concentration

| MTMS concentration [mmol/l] | Contact angle [°] | d [°] |
|---|---|---|
| 0.7 | 51.79 | 7.18 |
| 3.5 | 79.82 | 12.61 |
| 7 | 79.00 | 3.66 |
| 14 | 79.50 | 4.45 |
| 35 | 105.13 | 9.13 |
| 70 | 112.26 | 7.23 |

It was found that the water contact angle increases on both glass and silicon as the MTMS concentration increases. At the same time, increasing the concentration at low concentrations has a somewhat greater effect than at higher concentrations. The system approaches a maximum in the range of from 110-120°. Therefore, the contact angle is affected less and less by further increasing the coating concentration. Overall, it can also be seen that, from a concentration of around 7 mmol/l, values showing a moderate spread can be detected. In general, this points to a more homogeneous surface covering with coating molecules.

The data shows that it is possible to successfully coat both substrate materials in one coating process.

As is clear, the contact angle increases as the concentration of the coating reagent increases, asymptotically approaching an apparent maximum at higher concentrations. This seems plausible since the surface is saturated after a certain point, i.e. the layer has formed all over the surface. This effect can be easily derived from the results for silicon and glass. In the low coating concentration ranges, a greater effect in terms of the contact angle is achieved when the concentration is increased slightly, whereas this effect becomes weaker and weaker in the higher concentration ranges. In this respect, doubling the concentration from 35 mmol/l to 70 mmol/l only increases the water contact angle by another 10°. There are no discernible general differences for silicon or glass (the related requirement for coating glass and silicon at the same time is thus met).

On the basis of the results, an optimum minimum coating concentration for the process can also be derived. An optimum minimum coating concentration should be more than 30 mmol/l since it has been found that reliable and reproducible coatings are obtained above this concentration.

2.2.2 Functionalisation of Nozzle Bodies

Nozzle bodies are generally functionalised according to the procedure under section 1.1. The external appearance of nozzle bodies after coating was tested.

2.2.2.1 Impact of Activation Solution

In one test, nozzle bodies were activated using the various activation solutions and then coated with 1H,1H,2H,2H-tridecafluorooctyltriethoxysilane. Next, the bodies were visually checked for noticeable problems under a light microscope. In general, RCA-activated and piranha-activated nozzle bodies have a similar appearance.

Generally, coated nozzle bodies have a similar surface to uncoated nozzle bodies, even under the scanning electron microscope, and are thus considered optically identical. A monomolecular layer of an alkylsilane cannot be directly detected by scanning electron microscopes, so coated and uncoated nozzle bodies cannot be directly distinguished either. All coated nozzle bodies showed positive results in the capillary action test and were thus successfully coated. Morphological artefacts only occurred during the surface functionalisation in very few cases. These artefacts only occur in a very small number of cases, so the coating does not usually alter the surface morphology of the nozzles.

2.2.2.2 Capillary Action Test on Coated Nozzle Bodies

Table 4 illustrates the results of the capillary action test on ten hydrophobed, perfluorinated nozzle bodies coated with 0.03 mol/l 1H,1H,2H,2H-tridecafluorooctyltriethoxysilane. The method followed the description in section 1.1 and was carried out after each coating using randomly selected nozzle body samples.

TABLE 4

Capillary action test on coated, perfluorinated nozzle bodies (N = 10)

| Solution/formula (property) | Uncoated nozzle body spontaneously filled | Coated (perfluorinated) nozzle body spontaneously filled |
|---|---|---|
| Water/$H_2O$ (hydrophilic) | Yes | No |
| Perfluorooctane/$C8F18$ (hydrophobic, oleophobic) | No | Yes |

Direct evidence of the coating in the coated nozzle bodies is difficult to obtain since it can only be deduced by means of complicated, time-consuming measurement methods such as TOF-SIMS and ESCA after splitting the sandwich system. This is due to the low sample volumes resulting from the thin layer thickness of just a few nanometres.

The simplest way, therefore, is to use indirect evidence of the coating by making use of the altered capillary effect of the microstructure. The method is an identity test for the presence of the coating. This test is also suitable for large-scale quality control.

2.2.2.3 Impact on Spray Performance from Functionalisation Solution Residues in Nozzle Bodies In the laboratory situations used here, not all the samples emerged clean from the coating process. To be able to analyse the effect of coating residues on the spray pattern performance, a catalogue of fault images having images of characteristic nozzle faults was compiled. In the process, the nozzles were allocated to a relevant nozzle category depending on the location of the residue.

2.2.2.4 Effect of the Nozzle Body Category on Spray Performance

To investigate the effect of the nozzle body category on the spray performance of the atomisers, nozzles coated for the long-duration provocation test (cf. 0) were analysed under a microscope and assigned to the appropriate nozzle body category. Table 5 shows the results of the microscopic analysis of three batches (A to C), which were produced for the long-duration provocation test sampling. Overall, 151 nozzle bodies were coated with 0.03 mol/l 1H,1H,2H,2H-tridecafluorooctyltriethoxysilane in three different batches and then analysed under the microscope.

TABLE 5

Results of the nozzle body categorising based on samples for long-duration provocation test from 0

| Batch | Category I | Category II | Category III | Category IV | Total |
|---|---|---|---|---|---|
| A | 26 (53%) | 3 (6%) | 14 (29%) | 6 (12%) | 49 |
| B | 28 (54%) | 0 | 13 (25%) | 11 (21%) | 52 |
| C | 21 (42%) | 1 (2%) | 13 (26%) | 15 (30%) | 50 |
| Average | 49.64% | 2.71% | 26.52% | 21.13% | 151 |
| SD | 6.62% | 3.12% | 1.84% | 8.88% | |

For the long-duration provocation test, 60 atomisers having coated nozzles were provided. The original nozzles were removed from these devices and coated nozzles were fitted. The distribution of the coated nozzles used here in relation to the nozzle body categories can be seen in Table 6.

TABLE 6

Distribution of sample nozzle body categorisation for long-duration provocation test

| Category I | Category II | Category III | Category IV | Total |
|---|---|---|---|---|
| 30 | 0 | 15 | 15 | 60 |

All the coated nozzles were fitted in provided atomisers in a traceable manner so that it was always known which nozzle category was fitted in which device. They were fitted in particle-free conditions, as can be produced under laboratory conditions. After the provocation test, the progression of the spray patterns of the samples was analysed in a large histogram analysis.

After 120 test days in 1×2 in-use mode, i.e. two successive strokes per day, all the 14400 sprays dispensed in the test from the 60 coated nozzles were analysed in a comprehensive histogram analysis. It was found that initially individual group II spray patterns were formed. As the test continued, clear rows or bands emerged, which indicated that blocked devices preferably again displayed a group II spray in the following strokes. As the test time progressed, group III sprays developed from the group II sprays, and these would become permanent later in the test. In this test, the absolute number of group III sprays was relatively low, so the group II sprays were used for the bar chart analysis. Group II sprays are a precursor for group III sprays, meaning that they can be legitimately used for the further analysis.

It was shown that category III and category IV nozzle bodies cause group II sprays more often than nozzle body categories I and II—15% for nozzle body categories I and II and between 25 and 30% for nozzle body categories III and IV.

It was found that clean category I and II nozzle bodies have a lower number of spray pattern anomalies over the entire duration of the test than category III and IV nozzles. Residues in the nozzle region thus generally lead to more spray pattern anomalies. The number is even greater when both nozzle channels (category IV) are affected by deposits. The majority of the spray pattern anomalies in this test occur later on in the test. Category I and II nozzles always have better spray performance, even when broken down according to time interval. Both the short-term and long-term spray performance of clean category I and II nozzle bodies are considerably better than that of category III and IV nozzle bodies.

Therefore, it can be concluded that the residues impair the coating or the formation of the coating on the surface and spray performance deteriorates.

A RAMAN spectroscopic analysis revealed that the residues are polymer residues of the coating solution. During the drying phase after functionalisation, the coating solution presumably coalesced at the small cavities of the microstructure and polymerised out at these points during the tempering.

The results reveal that the yield of category I nozzles should be as high as possible for large-scale processes. For this purpose, it is appropriate to use systems that expel the excess coating solution, in particular systems based on the use of rotary forces, e.g. SRD systems (spin rinse dryers).

2.2.3 Performance of Functional Alkylsilane Coatings in in-Use Methods (Provocation Tests)

In the following, using a standard test method, the surface functionalisation of the nozzle bodies a coating method will be sufficiently analysed and evaluated as a measure for preventing the risk of nozzle blockage.

2.2.3.2 Provocation Test Using Functionalised Nozzles: Performance of the Surface Functionalisation in Relation to Plaque Deposits Using a provocation test (use of the predetermined provocation solution in atomisers), the behaviour of different layer functionalities when provoked plaque deposits occur was tested. In the process, nozzle bodies were coated with different coating reagents according to the method described in section 1.1 (with RCA activation).

The provocation test is set up as follows:
Coating Reagents:

Dynasylan® F8261 (=1H,1H,2H,2H-tridecafluorooctyltriethoxysilane) (F1308-OET)

n-octyltriethoxysilane (C8-OET)

1H,1H,2H,2H-perfluorooctyldimethylchlorosilane (F13C8-Cl)

n-octyldimethylchlorosilane (C8-Cl)

Concentration: 0.03 mol/l in each case

Formulation: as in 1.3.3

Number of inhalers: 50 for each coating, 30 for reference

In-use mode: 1×1 stroke/day

Duration of test: 28 days

Test parameters: Spray pattern according to spray pattern catalogue

The basic test set-up makes it possible to compare a large number of aspects within the experiment. Firstly, both fluorinated and non-fluorinated alkylsilanes are used here, and secondly, these are alkyltrialkoxysilane and alkyldimethylmonochlorosilane. This means that the basic coating chemistry in terms of the surface bonding can be tested, while so too can the actual layer performance determined by the alkyl side chains (fluorinated vs. non-fluorinated).

In the following, the spray pattern curves for group I sprays (cf. FIG. 9), group II sprays (cf. FIG. 10) and group III sprays (cf. FIG. 11) are shown in graphs.

2.2.3.1.1 Group I Spray Pattern Curve

FIG. 9 shows the group I ("good sprays") spray curves for the coated nozzles and the uncoated reference. The number of group I sprays decreases for all test branches to a greater or lesser extent over time, although all the test branches in which coated nozzles are used display a better spray pattern curve than the uncoated reference. It is not until around the end of the test that the spray pattern curves for test branches C8-OET, C8-Cl and F12C8-Cl approach the reference. In this regard, the number of group I sprays drops below 20% for these test branches.

This does not occur with coating reagent F13C8-OET, which shows excellent performance over the spray pattern curve. Up to the end of the test, a proportion of almost 80% remained in group I sprays ("good sprays"). This is an advantage of more than 60% over the other coating reagents. If this correlated with the coating reagent C8-OET, the advantage of the perfluorinated side chain of F1308-OET is clear.

The coating reagent C8-OET obtains a similarly poor result towards the end of the test as the two chlorosilanes F1308-Cl and C8-Cl. It is clear, however, that it has a significant advantage over these two compounds in the preceding test days, taking an intermediate position between F1308-OET and the two chlorosilanes.

Overall, the relatively poor spray performance of the two chlorosilanes is surprising. It is also surprising that, in relation to F1308-Cl, the benefit of a perfluorinated side chain is not detectable either compared with C8-Cl. The fact that C8-Cl provides similar results leads to the assumption that the surface bonding is not stable enough in the chlorosilanes. While they do have an advantage over the uncoated reference in the first few test days, this lasts only until day 17.

2.2.3.1.2 Group II Spray Pattern Curve

FIG. 10 shows the group II spray curves for the coated nozzles and the uncoated reference. The proportion of group II sprays ("spray pattern anomalies") increases over time to a greater or lesser extent for all test branches. The reference reaches its maximum as early as test day 4 at over 60%, whilst no specific maximum can be identified for the other test branches. There is a continuous increase of group II sprays over the test duration. What is also striking is the large advantage of the coating reagent F1308-OET. At the end of the test, the proportion of spray pattern anomalies is just 15%, and from day 5 onwards is always below the other test branches over the entire test period.

2.2.3.1.3 Group III Spray Pattern Curve

FIG. 11 shows the group III ("jet divergency") spray curves for the coated nozzles and the uncoated reference. The figure shows that the proportion of group III sprays also increases to a greater or lesser extent over the time period for all test branches. Towards the end of the test, the two chlorosilanes reach a similar rate of group III sprays (almost 60%) as the uncoated reference. Compared with the reference, therefore, the chlorosilanes show only a temporary benefit lasting a few test days since the chlorosilanes and the reference already have a similar number of group III sprays (around 40%) after day 16. In this view, the coating reagent C8-OET again assumes a position in the middle having a group III spray rate of almost 30% at the end of the test. The coating reagent F13C8-OET has by far the best spray performance: Less than 10% of the atomisers showed a group III spray over all test days.

2.2.3.1.4 Group III Spray Pattern Curve: 10-Day Average Rate Towards the End of the Test The advantage of the coating reagent F1308-OET is particularly clear from the 10-day average rate shown in FIG. 15. In the 10-day average, the reference reaches a rate of almost 50% group III sprays. This is similar to the two chlorosilane test branches, which exhibit a similarly high 10-day average rate of around 50%. The lowest rate of group III sprays is achieved by the test branch containing the coating reagent F1308-OET, which achieves a 10-day average rate of less than 5% towards the end of the test; this is remarkably better than all the other test branches. The coating reagent C8-OET also has a significantly better 10-day average rate of just around 25%. This coating reagent thus provides significantly better protection against plaque deposits than the alkylchlorosilanes.

Overall, the advantage of alkyltrialkoxysilanes over alkylchlorosilanes is very unmistakeable.

The result of the provocation test using functionalised nozzles shows that the likelihood of a clogged nozzle can be dramatically reduced when the correct coating reagent is used.

For incomprehensible reasons, the alkyldimethylmonochlorosilanes performed relatively badly and barely brought any benefit to spray performance compared with the reference. This was unexpected since the alkyldimethylmonochlorosilanes also exhibit good binding properties in the literature (cf. Fadeev, A. Y. and T. J. McCarthy, *Trialkylsilane monolayers covalently attached to silicon surfaces: wettability studies indicating that molecular topography contributes to contact angle hysteresis*. Langmuir, 1999. 15(11): pp. 3759-3766). The spray pattern curve over the testing period is no better than the uncoated reference.

Reasons why the alkyldimethylmonochlorosilanes bonded poorly to the surface can only be hypothesised. One possible critical disadvantage of alkyldimethylmonochlorosilanes is that this substance class only has one site for binding to the surface. By comparison, alkyltrialkoxysilanes have two more coordination sites, which appears to lead to increased bonding stability. If consideration is also given to the force conditions in the atomisers used, which can reach a pressure of more than 200 bar and flow rate of over 130 m/s in the nozzle channel, it may be that these forces are simply too great for just one coordination site, resulting in layer erosion or layer detachment.

2.2.4 Long-Term Performance of 1H,1H,2H,2H-Tridecafluorooctyltriethoxysilane in in-Use Tests In a provocation test, it was investigated how long nozzle blockages could be avoided by using coated nozzles. To do so, nozzles were coated with 1H,1H,2H,2H-tridecafluorooctyltriethoxysilane and tested in a provocation test in in-use mode 1×2 over a period of 120 days. Overall, 60 coated nozzles of nozzle body categories I+II, III and IV were used.

The provocation test is set up as follows:

Coating Reagent:

Dynasylan® F8261 (=1H,1H,2H,2H-tridecafluorooctyltriethoxysilane) (F1308-OET)

Reference (uncoated)

Concentration: 0.03 mol/l

Formulation: as in 1.3.3

Duration of test: Ref.=45 days, F13C8=120 days

Number of inhalers:

60 coated with F13C8-OET, 30 reference (uncoated)

In-use mode: 1×2 strokes/day

Test parameters: Spray pattern according to spray pattern catalogue 2.2.4.1 Group I Spray Pattern Curve FIG. 13 shows the group I ("good sprays") spray curves for the long-duration provocation test. FIG. 13 illustrates the great advantage the coating has over the uncoated reference. Whereas the reference had only around 20% group I sprays ("good sprays") on test day 45, the coated nozzles had more than 80%. Even at the end of the test on test day 120, F13C8-OET still had more than 60% of the atomisers producing a group I spray ("good spray"). As can be seen in the graph, the reference was stopped on day 45 since the good-spray rate had reached a balanced state at around 20%.

Within the first few test days, some of the coated atomisers actually began to deviate from a group I spray. This can be traced back to the presence of coating residues. Over the first few days, therefore, the reference tended to perform slightly better than the devices having coated nozzles. This effect lasted until around day 10, after which the number of good sprays in the reference began to drop considerably. In this case, the reason for this phenomenon at the beginning is the use of "good" and "bad" nozzle categories. In terms of coating residues, category I and II nozzles as well as category III and IV nozzles were used in this test.

It is very clear from this test that coating solution residues can also cause group II and group III sprays.

2.2.4.2 Group II Spray Pattern Curve

FIG. 14 shows the group II ("spray anomalies") spray curves for the long-duration provocation test. For the reference in particular, the number of group II sprays increases very sharply over time. In this regard, more than 70% group II sprays were already observed on day 20. Looking at the spray pattern curve for the coated nozzles (F1308-OET), it can be seen that a moderate increase in group II sprays was also apparent in this case. However, the coated nozzles only had around 30-40% group II sprays even at the end of the test on day 120; this is considerably lower than the reference.

It is also apparent that spray pattern anomalies (group II sprays) occurred in the devices having coated nozzles as early as on the first test day. This is down to the coating residues as mentioned above. Despite the coating, the F1308 devices also showed an increase in group II sprays after a certain time, which indicates the process of plaque deposit formation in this case too. Over the spray pattern curve, a larger increase can be seen from around day 40.

In terms of the coating residues, the coated nozzle bodies having coating residues can be discarded before being fitted as part of a visual check on the coated nozzle bodies. Discarding these significantly reduces the spray pattern anomalies for devices having coated nozzles.

2.2.4.3 Group III Spray Pattern Curve

FIG. 15 shows the group III ("jet divergency") spray curves for the long-duration provocation test. As can be seen in the figure, very few group III sprays occur overall (batch effects also play a role in this respect). When comparing the coated nozzles with the reference, it can be seen that the reference already showed some group III sprays after test day 10, whereas with the coating this occurred for the first time as of day 70. This means that the coating was able to delay the occurrence of the first group III sprays for around 60 days.

Under stress conditions, the atomiser batch tested here had a very low number of group III sprays from the outset, although a large number of group II sprays were formed very quickly in the reference. Generally, these group II sprays quickly react further to become group III sprays and can thus also be an indicator of nozzle blockages.

2.2.4.4 Group III Sprays: 10-Day Average Rate Towards the End of the Test

FIG. 16 shows the 10-day average rate at the end of the test for the long-duration provocation test. FIG. 16 again shows a summary of the results of the spray pattern progression for group Ill sprays. On day 45, the reference had a rate of around 5% group III sprays. By comparison, the atomisers having coated nozzles had still not shown any group III sprays. These occurred sporadically from around day 70. Even at the end of the test on day 120, the atomiser devices having coated nozzles had a similar 10-day average rate of around 5%.

2.2.4.5 Results for Performance of 1H,1H,2H,2H-Tridecafluorooctyltriethoxysilane Nozzle Coatings The result of the long-duration provocation test using functionalised nozzles shows that the likelihood of a clogged nozzle can be dramatically reduced even over a very long test period. The duration of this test was 120 days altogether. The 120 days were derived from a potential 4-month use of the inhaler. For the nozzles coated in this case with 1H,1H, 2H,2H-tridecafluorooctyltriethoxysilane, a group III spray first occurred on test day 70. The reference, on the other hand, already showed the first group III sprays after day 10. This is an advantage for the coating of 60 days. The coating delayed the appearance of group III sprays for this long period of time, which is an excellent result.

What is also striking in this test is that very few group III sprays occurred over the entire test duration. This is surprising even for the uncoated reference. The reason for this is the atomiser batch itself, which has also demonstrated very few group III sprays in other tests. The incidence of group II and III sprays is dependent on the device batch used. However, it is notable in this test that the number of group II sprays remained very high for a very long time. Generally, the number of group III sprays increases significantly when the maximum in the group II sprays is reached very quickly (i.e. devices having group II sprays become devices having group III sprays).

The reference was stopped at day 45 since the advantage of the coating was already clear and the reference had reached a balanced state. At day 70, the inhalers having the coated nozzles also showed the first group III sprays. However, the rate of the increase did not match that of the uncoated reference; instead, it rose much more slowly.

2.3. Long-Term Stability of the Coating: Stability Study on Coated Si/Glass Planar Substrates A stability study is designed to investigate the effect of different stress parameters (pH, temperature, storage time) on the layer performance of 1H,1H,2H,2H-tridecafluorooctyltriethoxysilane. For this purpose, silicon and glass substrates were coated to three concentrations in a plurality of coating approaches and stored over time in ethanolic placebo solution. The samples were each coated to identical coating parameters and differed only on account of the concentration of the coating solution. The stability of the samples was then assessed using layer thickness measurements and contact angle measurements.

2.3.1 Stability Study Set-Up

Si/glass planar substrates were coated at the three following concentrations: 0.003 mol/l, 0.015 mol/l and 0.03 mol/l. The samples were stored in a sealed manner protected from light in polyethylene bottles in an ethanolic placebo solution at pHs of 2.0 and 4.5, and at room temperature in the laboratory (20° C.±3° C.) and 40° C. in the climatic test cabinet. For the high coating concentration, the storage time was 14, 30, 90 and 180 days. The two lower coating concentrations were stored for just 30 and 180 days. The study parameters are summarised in Table 7.

TABLE 7

Set-up for Si/glass planar substrate stability study

| Sample concentration | | Time [days] | | | | Temperature | | pH | |
|---|---|---|---|---|---|---|---|---|---|
| [mol/l] | Substrate | 14 | 30 | 90 | 180 | RT | 40° C. | 2.0 | 4.5 |
| 0.03 | Si + glass | x | x | x | x | x | x | x | x |
| 0.015 | Si + glass | | x | x | x | x | x | x | x |
| 0.003 | Si + glass | | x | | x | x | x | x | x |
| | Reference | x | x | x | x | x | x | x | x |

Reference: x = carried out without silicon/glass substrates 2.3.2 Coating the Si/Glass Planar Substrates For the stability study, the Si/glass planar substrates were coated in several batches in accordance with section.

2.3.3 Storing the Substrates

For the stability study, two ethanolic placebo solutions at pH 2.0 and 4.5 were used. On the day the samples were placed into storage, 170 g ethanolic placebo solution was placed in each polyethylene bottle. Next, two silicon and glass substrates were added to each bottle using wafer tweezers. In doing so, care should be taken to ensure the substrates are positioned in the bottle such that they do not adhere to one another. Once the bottles are closed, the weight of the entire PE bottle was determined and recorded in order to be able to determine the weight loss due to the storage when the substrates are removed from storage. In addition, reference samples without substrates were also put into storage for each storage duration, pH and temperature.

2.3.4 Checking the pH and Weight Upon Removal from Storage

On the day the substrates are removed from storage, the weight of the PE bottle was determined again and the weight lost over the storage time thus ascertained. In addition to the weight loss, the pH of the solution was also checked. This makes it possible to check whether the PE bottle was sufficiently tight over the duration of the test and whether the pH has changed during storage.

2.3.5 Analysing the Stability Study

The stability study was analysed using static contact angle measurement and layer thickness measurements by means of spectroscopic ellipsometry. The values of a sample upon removal from storage were related to starting values determined beforehand for the contact angle and layer thickness. The starting values were collected using a representative sample that had not been stored and contained samples from each coating process carried out beforehand.

2.3.5.1 Change in the Contact Angle Over the Storage Time

Below, the results in term of the contact angle measurements on silicon and glass are presented.

The tests show a clear concentration effect for the starting values on silicon. As the coating concentration was increased, a higher contact angle for water and n-dodecane was obtained and a smaller standard deviation was produced. In each case, 5 droplets of water and 5 droplets of n-dodecane were measured per substrate. With 10 measurements per droplet, this resulted in 50 angles.

2.3.5.1.1 Changes to the Contact Angle on Silicon when Stored at Room

Temperature (25° C.) The change in the water contact angle and n-dodecane contact angle on silicon when stored at room temperature was tested. The test results are summarised in Tables 8 and 9.

TABLE 8

Changes to the water contact angle on silicon when stored at room temperature (25° C.)

| MTMS concentration | | Contact angle [°] | | | | |
|---|---|---|---|---|---|---|
| | | Starting | Change | | | |
| [mmol/l] | pH | value | 14 days | 30 days | 90 days | 180 days |
| 0.03 | 2.0 | 112.72 | 1.39 | 2.07 | 3.44 | 7.34 |
| 0.03 | 4.5 | 112.72 | 3.05 | 4.18 | 5.66 | 6.97 |
| 0.015 | 2.0 | 108.78 | n.d.[1] | 4.73 | 3.25 | 3.96 |

TABLE 8-continued

Changes to the water contact angle on silicon when stored at room temperature (25° C.)

| MTMS concentration [mmol/l] | pH | Starting value | Contact angle [°] Change | | |
|---|---|---|---|---|---|
| | | | 14 days | 30 days | 90 days | 180 days |
| 0.015 | 4.5 | 108.78 | n.d.[1] | 6.55 | 3.27 | 3.19 |
| 0.003 | 2.0 | 101.61 | n.d.[1] | 1.76 | n.d.[1] | 7.52 |
| 0.003 | 4.5 | 101.61 | n.d.[1] | 0.01 | n.d.[1] | −1.41 |

[1]n.d. = not determined

TABLE 9

Changes to the n-dodecane contact angle on silicon when stored at room temperature (25° C.)

| MTMS concentration [mmol/l] | pH | Starting value | Contact angle [°] Change | | | |
|---|---|---|---|---|---|---|
| | | | 14 days | 30 days | 90 days | 180 days |
| 0.03 | 2.0 | 68.82 | 0.51 | 3.11 | 4.40 | 4.82 |
| 0.03 | 4.5 | 68.82 | 0.33 | 3.20 | 3.51 | 5.42 |
| 0.015 | 2.0 | 66.40 | n.d.[1] | −1.71 | 0.82 | 1.55 |
| 0.015 | 4.5 | 66.40 | n.d.[1] | 0.26 | 1.59 | 1.48 |
| 0.003 | 2.0 | 61.42 | n.d.[1] | 6.68 | n.d.[1] | 5.03 |
| 0.003 | 4.5 | 61.42 | n.d.[1] | 2.20 | n.d.[1] | −1.72 |

[1]n.d. = not determined

The tests show that the water contact angle and the n-dodecane contact angle only vary to a minor extent (x≤10°) over the storage period considered. However, a gradual fall in the contact angle over the storage period can be seen for the coating concentration 0.003 mol/l. This effect can be detected in both water and dodecane.

It can be stated that the spread in the contact angle at a coating concentration of 0.003 mol/l is very high overall. In some cases, it is over 20° and thus conceals potential effects. By comparison, at the coating concentrations 0.015 mol/l and 0.03 mol/l, very precise values are achieved with very low spread. This indicates that a homogeneous coating is not always achieved at a concentration of 0.003 mol/l.

Since all the average changes for the water and the dodecane contact angle remain below 10°, it can be concluded that, in this case, at most there has merely been a change to the layer alteration but no layer detachment. The water contact angle for an uncoated silicon or glass substrate would be at around 30-40°. An activated substrate would be even more hydrophilic. The water contact angles considered here are above 100° even after storage.

Detachment of the layer would lead to changes in the water contact angle of well over 50°. This is clearly not the case here.

There was also no general discernible difference between storage at pH 2.0 and pH 4.5 (i.e. the coating is acid-resistant in the tested pH region).

2.3.5.1.2 Changes to the Contact Angle on Silicon when Stored at 40° C.

The change in the water contact angle and n-dodecane contact angle on silicon when stored in the climatic test cabinet at 40° C. was tested. The test results are summarised in Tables 10 and 11.

TABLE 10

Changes to the water contact angle on silicon when stored at 40° C.

| MTMS concentration [mmol/l] | pH | Starting value | Contact angle [°] Change | | | |
|---|---|---|---|---|---|---|
| | | | 14 days | 30 days | 90 days | 180 days |
| 0.03 | 2.0 | 112.72 | 0.01 | 5.20 | 4.17 | 8.13 |
| 0.03 | 4.5 | 112.72 | 3.49 | 3.41 | 6.74 | 9.08 |
| 0.015 | 2.0 | 108.78 | n.d.[1] | −6.50 | 0.13 | 4.39 |
| 0.015 | 4.5 | 108.78 | n.d.[1] | −3.53 | 3.42 | 6.34 |
| 0.003 | 2.0 | 101.61 | n.d.[1] | 0.90 | n.d.[1] | 16.73 |
| 0.003 | 4.5 | 101.61 | n.d.[1] | 3.83 | n.d.[1] | 6.08 |

[1]n.d. = not determined

TABLE 11

Changes to the dodecane contact angle on silicon when stored at 40° C.

| MTMS concentration [mmol/l] | pH | Starting value | Contact angle [°] Change | | | |
|---|---|---|---|---|---|---|
| | | | 14 days | 30 days | 90 days | 180 days |
| 0.03 | 2.0 | 68.82 | 0.88 | 2.17 | 1.73 | 7.19 |
| 0.03 | 4.5 | 68.82 | 2.29 | 2.42 | 5.36 | 5.93 |
| 0.015 | 2.0 | 66.40 | n.d.[1] | −1.71 | −0.19 | 1.19 |
| 0.015 | 4.5 | 66.40 | n.d.[1] | 0.26 | 2.11 | 3.21 |
| 0.003 | 2.0 | 61.42 | n.d.[1] | −4.68 | n.d.[1] | 11.67 |
| 0.003 | 4.5 | 61.42 | n.d.[1] | 1.67 | n.d.[1] | 2.21 |

[1]n.d. = not determined

The tests show that the contact angle only varies slightly in terms of the stress variables shown, as set out in Table 7 in section 2.3.1. The average change in the water contact angle remains below 10°, even when the temperature is increased. A gradual fall in the contact angle over time was also recorded here at the concentrations 0.015 mol/l and 0.03 mol/l, similarly to the values determined at room temperature.

Overall, it can be stated that increasing the temperature does not reduce or alter the hydrophobicity of the substrates either. The data is absolutely comparable with the values at room temperature. Therefore, no temperature effects can be detected on the silicon substrates.

2.3.5.1.3 Changes to the Contact Angle on Glass when Stored at Room Temperature (25° C.)

The change in the water contact angle and n-dodecane contact angle on glass when stored at room temperature was tested. The test results are summarised in Tables 12 and 13.

TABLE 12

Changes to the water contact angle on glass when stored at room temperature (25° C.)

| MTMS concentration [mmol/l] | pH | Starting value | Contact angle [°] Change | | | |
|---|---|---|---|---|---|---|
| | | | 14 days | 30 days | 90 days | 180 days |
| 0.03 | 2.0 | 112.06 | 2.13 | −2.26 | −1.00 | 3.92 |
| 0.03 | 4.5 | 112.06 | −4.31 | 0.75 | −6.21 | 0.61 |
| 0.015 | 2.0 | 87.41 | n.d.[1] | −9.10 | −14.92 | −13.81 |
| 0.015 | 4.5 | 87.41 | n.d.[1] | −12.65 | −12.05 | −19.27 |
| 0.003 | 2.0 | 91.40 | n.d.[1] | −5.48 | n.d.[1] | 22.08 |
| 0.003 | 4.5 | 91.40 | n.d.[1] | −3.65 | n.d.[1] | 2.03 |

[1]n.d. = not determined

TABLE 13

Changes to the dodecane contact angle on glass when stored at room temperature (25° C.)

| MTMS concentration [mmol/l] | pH | Contact angle [°] | | | | |
|---|---|---|---|---|---|---|
| | | Starting value | 14 days | 30 days | 90 days | 180 days |
| | | | Change | | | |
| 0.03 | 2.0 | 68.91 | 3.74 | 1.27 | 2.61 | 2.79 |
| 0.03 | 4.5 | 68.91 | 2.64 | 5.84 | -2.66 | 1.59 |
| 0.015 | 2.0 | 47.52 | n.d.[1] | -11.50 | -12.20 | -2.78 |
| 0.015 | 4.5 | 47.52 | n.d.[1] | -14.49 | -9.92 | -15.51 |
| 0.003 | 2.0 | 60.57 | n.d.[1] | 16.11 | n.d.[1] | 2.85 |
| 0.003 | 4.5 | 60.57 | n.d.[1] | 9.65 | n.d.[1] | 6.89 |

[1]n.d. = not determined

It can be seen that the layer does not detach on glass either. In the substrates, the average change in the contact angle also remains below 10° at a coating concentration of 0.03 mol/l, as already seen with the silicon substrates. Looking at the data for the coating concentrations 0.003 mol/l and 0.015 mol/l, a very high spread in the values can be seen here too, in particular for the coating concentration 0.003 mol/l. This is similar to the spread on silicon for the same coating concentration and also conceals potential effects here.

The results for the coating concentration 0.015 mol/l also display a noticeable feature. Here, the contact angle for water and n-dodecane is greater than the determined starting value. This trend was measured for all samples, though it is insignificant once standard deviation is taken into account.

Overall, it can be concluded that no storage effects can be noted for glass substrates either. This also includes the two pHs tested.

2.3.5.1.4 Changes to the Contact Angle on Glass when Stored at 40° C.

The change in the water contact angle and n-dodecane contact angle on glass when stored at 40° C. was tested. The test results are summarised in Tables 14 and 15.

TABLE 14

Changes to the water contact angle on glass when stored at 40° C.

| MTMS concentration [mmol/l] | pH | Contact angle [°] | | | | |
|---|---|---|---|---|---|---|
| | | Starting value | 14 days | 30 days | 90 days | 180 days |
| | | | Change | | | |
| 0.03 | 2.0 | 112.06 | 0.79 | -2.19 | 17.55 | -1.56 |
| 0.03 | 4.5 | 112.06 | -1.89 | 2.74 | -1.67 | -1.08 |
| 0.015 | 2.0 | 87.41 | n.d.[1] | -17.06 | -13.58 | -14.47 |
| 0.015 | 4.5 | 87.41 | n.d.[1] | -17.54 | -18.90 | -23.69 |
| 0.003 | 2.0 | 91.40 | n.d.[1] | -16.71 | n.d.[1] | 14.21 |
| 0.003 | 4.5 | 91.40 | n.d.[1] | -13.74 | n.d.[1] | -16.11 |

[1]n.d. = not determined

TABLE 15

Changes to the dodecane contact angle on glass when stored at 40° C.

| MTMS concentration [mmol/l] | pH | Contact angle [°] | | | | |
|---|---|---|---|---|---|---|
| | | Starting value | 14 days | 30 days | 90 days | 180 days |
| | | | Change | | | |
| 0.03 | 2.0 | 68.91 | 2.03 | -0.67 | 13.38 | -0.03 |
| 0.03 | 4.5 | 68.91 | 7.04 | 2.51 | 3.96 | -1.25 |
| 0.015 | 2.0 | 47.52 | n.d.[1] | -17.96 | -13.12 | -13.24 |
| 0.015 | 4.5 | 47.52 | n.d.[1] | -17.34 | -19.10 | -21.52 |
| 0.003 | 2.0 | 60.57 | n.d.[1] | 12.30 | n.d.[1] | 0.80 |
| 0.003 | 4.5 | 60.57 | n.d.[1] | 4.83 | n.d.[1] | -3.87 |

[1]n.d. = not determined

In principle, the values determined for 40° C. are comparable with those at room temperature.

Overall, it can be concluded here too that no specific storage effect can be detected for glass at a temperature of 40° C. This also includes the two pHs tested 2.0 and 4.5.

2.3.5.2 Effect of Storage on Layer Thickness

Below, the results in term of the layer thickness measurements carried out on silicon and glass using ellipsometry are presented.

Each substrate was measured three times at the angles 65°, 70° and 75° using spectroscopic ellipsometry.

The sample having the coating concentration 0.003 mol/l stood out in terms of their standard deviation in the ellipsometric measurements too. In addition, it can also be seen that as the concentration was increased further, the layer thickness on the silicon substrates did not increase by a measurable amount. However, this effect can be noted as a trend on glass substrates.

The model assumed for the analysis corresponds to the explanations under section 1.4.4. The refractive index required for the SAM layer thickness measurement was taken from the literature and is 1.256 (cf. Jung, J.-I., J. Y. Bae, and B.-S. Bae, *Characterization and mesostructure control of mesoporous fluorinated organosilicate films*. Journal of Materials Chemistry, 2004. 14(13): pp. 1988-1994).

2.3.5.2.1 Changes to the Layer Thickness on Silicon when Stored at Room Temperature and at 40° C.

The change in the layer thickness on silicon when stored at room temperature (25° C.) and at 40° C. was tested. The test results are summarised in Tables 16 and 17.

TABLE 16

Changes to the layer thickness of the MTMS coating on silicon when stored at room temperature (25° C.)

| MTMS concentration [mmol/l] | pH | Layer thickness [nm] | | | |
|---|---|---|---|---|---|
| | | Starting value | 30 days | 90 days | 180 days |
| | | | Change | | |
| 0.03 | 2.0 | 0.93 | -0.10 | -0.02 | -0.06 |
| 0.03 | 4.5 | 0.93 | -0.10 | -0.14 | -0.11 |
| 0.015 | 2.0 | 1.06 | -0.05 | 0.11 | 0.16 |
| 0.015 | 4.5 | 1.06 | -0.02 | 0.03 | -0.01 |
| 0.003 | 2.0 | 1.05 | 0.23 | n.d.[1] | 0.17 |
| 0.003 | 4.5 | 1.05 | 0.15 | n.d.[1] | -0.02 |

[1]n.d. = not determined

TABLE 17

Changes to the layer thickness of the MTMS coating on silicon when stored at 40° C.

| MTMS concentration [mmol/l] | pH | Layer thickness [nm] Starting value | 30 days | Change 90 days | 180 days |
|---|---|---|---|---|---|
| 0.03 | 2.0 | 0.93 | 0.04 | −0.11 | −0.08 |
| 0.03 | 4.5 | 0.93 | 0.01 | −0.17 | −0.14 |
| 0.015 | 2.0 | 1.06 | 0.00 | 0.04 | 0.07 |
| 0.015 | 4.5 | 1.06 | −0.08 | −0.04 | −0.03 |
| 0.003 | 2.0 | 1.05 | 0.04 | n.d.[1] | 0.16 |
| 0.003 | 4.5 | 1.05 | 0.01 | n.d.[1] | −0.07 |

[1]n.d. = not determined

It can be seen that the coating produced on the silicon is very thin. For the starting values, the layer thickness is around 0.7 to 0.9 nm and thus corresponds to the values in the literature (cf. Plueddemann, E. P., *Silane Coupling Agents*, 2 ed. 1991, New York: Plenum Publishing Corporation). If the spread in the starting values and in the values upon removal from storage are taken into account, there is no discernible storage effect on the layer thickness. This relates to both the temperature change from room temperature (25° C.) to 40° C. and the change in pH from 2.0 to 4.5

As regards the impact of the coating concentration, the aforementioned observation can be included in the development of the standard deviation. The spread in terms of the layer thickness also becomes more moderate as the coating concentration increases, which indicates a more homogeneous layer formation at higher concentrations.

2.3.5.2.2 Changes to the Layer Thickness on Glass when Stored at Room Temperature and at 40° C.

The change in the layer thickness on glass when stored at room temperature (25° C.) and at 40° C. was tested. The test results are summarised in Tables 18 and 19.

TABLE 18

Changes to the layer thickness of the MTMS coating on glass when stored at room temperature (25° C.)

| MTMS concentration [mmol/l] | pH | Layer thickness [nm] Starting value | 30 days | Change 90 days | 180 days |
|---|---|---|---|---|---|
| 0.03 | 2.0 | 1.50 | 0.29 | −0.96 | −0.26 |
| 0.03 | 4.5 | 1.50 | −1.03 | −0.27 | −0.27 |
| 0.015 | 2.0 | 1.43 | −0.10 | −0.12 | −0.13 |
| 0.015 | 4.5 | 1.43 | −0.26 | −0.14 | −0.18 |
| 0.003 | 2.0 | 1.34 | −0.19 | n.d.[1] | −0.36 |
| 0.003 | 4.5 | 1.34 | 0.16 | n.d.[1] | −0.28 |

[1]n.d. = not determined

TABLE 19

Changes to the layer thickness of the MTMS coating on glass when stored at 40° C.

| MTMS concentration [mmol/l] | pH | Layer thickness [nm] Starting value | 30 days | Change 90 days | 180 days |
|---|---|---|---|---|---|
| 0.03 | 2.0 | 1.50 | −0.68 | −0.49 | −0.64 |
| 0.03 | 4.5 | 1.50 | −0.17 | −0.28 | −0.19 |
| 0.015 | 2.0 | 1.43 | −0.01 | −0.24 | −0.58 |
| 0.015 | 4.5 | 1.43 | −0.35 | −0.09 | −0.30 |
| 0.003 | 2.0 | 1.34 | 0.06 | n.d.[1] | −0.71 |
| 0.003 | 4.5 | 1.34 | 0.03 | n.d.[1] | −0.38 |

[1]n.d. = not determined

It can be seen that the layer thickness of the film generated on glass is significantly greater than on silicon. When the starting values are considered, the thickness is approximately 2 nm and is thus more than twice as thick as the film generated on silicon. In this case, this is down to a higher density of binding sites (in particular OH bonds) between the generated film and glass (compared with silicon) and/or a greater degree of surface roughness on the glass substrate used (compared with the silicon substrate used).

As has already been demonstrated, there is a discernible concentration effect in terms of layer thickness for the coating on glass. As the concentration of the coating solution increases, the layer thickness tends to become greater. However, this effect is insignificant and is concealed by a considerable degree of spread. Even for the highest coating concentration of 0.03 mol/l, the spread in the starting values is still close to around 0.5 nm.

It can therefore be concluded that the layer is detectable and there are no discernible significant changes to the layer thickness due to the pH or temperature. In addition, an effect of the coating concentration on the layer thickness can be noted. For silicon, the use of higher coating concentrations resulted in a moderate spread within the layer thickness measurements. In the case of glass, at high coating concentrations, increasing the concentration tends to lead to higher layer thicknesses being detected (this effect was within the standard deviation of the measurements determined).

2.3.5.3 Stability Study Results

The results of the stability study show that, under the framework conditions tested here, the coating can be deemed stable. This is demonstrated by the values from both the static contact angle measurement and the ellipsometric layer thickness measurements.

For the substrates used, complete layer detachment was not identified under any of the tested stress conditions; however, the static contact angle measurements on silicon indeed show that the layer becomes slightly more hydrophilic over the storage period. This correlates well with the data from the provocation tests carried out since group III sprays occur in coated nozzles after a certain point of the test in this case too, which can also be considered an indicator of a possible layer thickness change. The rate of the increase in group III sprays in coated nozzles does not match that of an uncoated reference. In this respect, the increase in group III sprays is always much slower in coated nozzles, indicating the layer effect is still present.

The results of the ellipometric layer thickness measurements also indicate a stable layer in all samples. The layer is always detectable and essentially no decrease in the layer thickness is noted.

The results again show that glass and silicon substrates can be coated simultaneously in one coating method.

2.4 Effect of Surface Functionalisation on Atomiser Performance

The effect of coated nozzles on atomiser performance was tested. The nozzles tested were transformed using 1H,1H,2H,2H-tridecafluorooctyltriethoxysilane as a coating agent in accordance with section 1.1.

2.4.1 Effect of the Coating on Priming Behaviour

The effect of coated nozzles on the priming behaviour of the atomiser was tested.

Priming refers to the initial first operation of the device. In this case, the first five strokes immediately after the container used and filled with provocation solution was inserted were compared in terms of delivered mass and metered mass (this was an investigation of the priming behaviour, it being possible to discern the number of strokes it takes for the discharged weight to reach its complete or target value).

2.4.1.1 Priming Behaviour Progression: Delivered Mass (DM) and Metered Mass (MM)

The priming behaviour of atomisers comprising coated and uncoated nozzle bodies was tested.

It was found that, in terms of the priming behaviour progression in relation to delivered mass and metered mass, there was no difference between the results from the atomiser test groups having coated nozzle bodies and uncoated nozzle bodies. Therefore, the coating has no impact on the priming behaviour.

2.4.1.2 Effect on the Metering Behaviour: Comparison Between Delivered Mass and Metered Mass in 120-Day in-Use Mode The effect of coated nozzles on the metering behaviour was tested over an in-use period (provocation mode) of 120 days. The progression of the delivered mass (DM) and metered mass (MM) for atomisers 9 having coated and uncoated nozzles was determined. The determination of the delivered mass and metered mass can be found in section 1.4.3.

2.4.1.2.1 Delivered Mass

The progression of the delivered mass for atomisers 9 having coated and uncoated nozzle bodies was tested over an in-use period of 120 days.

It was clearly shown that, initially, there was no difference between the progression of the delivered mass when using devices having coated and uncoated nozzle bodies. However, this changed after day 20, after which point the test group of devices not having a coating on the nozzle body saw an increase in the delivered mass. By day 45, the increase in the delivered mass reached almost 12 mg and thus remained significantly above the average delivered mass for devices having a coating on the nozzle bodies.

This increase was caused by the appearance of spray pattern anomalies in the group of atomisers not having a coating on the nozzle body. The test was run in provocation mode and, as it progressed, exhibited more group II sprays (spray pattern anomalies) and group III sprays in the reference group. Plaque deposits can indeed have an effect on the delivered mass since they cause deviations in the impact angle (the spray anomalies thus affect the formation of the impact disc in the DJI nozzles and thus also influence the aerosol backscattering or formation of residue droplets on the nozzle).

Fundamentally, however, it was found that the two test groups display totally comparable metering behaviour. This is only changed by the occurrence of undesirable spray pattern anomalies.

2.4.1.2.2 Metered Mass

The progression of the metered mass from atomisers having coated and uncoated nozzle bodies was tested over an in-use period of 120 days.

In this case too, the tests carried out did not show any difference in the progression of the metered mass between atomisers having coated and uncoated nozzle bodies, but rather the results were completely comparable with one another.

Therefore, it can be concluded that the coating does not have any effect on the metering behaviour of the atomiser. This relates to both the priming behaviour and the delivered and metered mass.

2.4.2 Effect of Coated Nozzles on Particle Size Distribution

The effect of coated nozzles on particle size distribution was tested. Experiments were carried out on the progression of particle size distribution for atomisers having coated and uncoated nozzles. The particle size distribution was determined by measurements taken on the Andersen cascade impactor (according to Ph. Eur.) and via laser refraction (in this case, a Helos BF measurement instrument from Sympatec).

The tested atomisers having coated and uncoated nozzle bodies had identical particle size distributions within the accuracy limits of the relevant measurement method.

Experiments were also carried out on the duration of spray of atomisers fitted with coated and uncoated nozzles. In each case, ten devices were tested, with five individual measurements being taken on each one.

It was found that the duration of spray for atomisers having coated and uncoated nozzles did not differ significantly. A duration of spray of $0.99 \pm 0.03$ seconds was determined for coated nozzles, and a duration of spray of $0.96 \pm 0.03$ was determined for uncoated nozzles. Therefore, within the measurement accuracy limits, no difference can be discerned in the duration of spray for coated and uncoated nozzles.

2.4.3 Overall Results Regarding the Effect of the Coating on Spray Performance No significant difference can be discerned between atomisers having coated nozzles and those having uncoated nozzles in terms of the device parameters tested. In this respect, the nozzles can be deemed identical.

The results of this performance analysis of coated and uncoated nozzle bodies showed that the coating has no impact on the device parameters tested in this case. This relates to the priming behaviour, the metering accuracy, the particle size distribution and the duration of spray.

In light of this, the method tested here for coating nozzles and nozzle bodies fulfils a basic requirement for measures intended to counteract the phenomenon of clogged nozzles: The possibility of the coating affecting the characteristic functional parameters of the atomiser can be ruled out.

2.5 Testing Other Coating Reagents: Effect of Alkyl Side Chain Length

The tests described above show that coatings based on fluorinated silanes, in particular fluoroalkylsilanes are exceptionally suitable for preventing clogged or blocked nozzles. In addition, some non-fluorinated silanes, in particular alkylsilanes, showed promising results.

The tests below are aimed at identifying alternative effective coating molecules.

The focus of the following test is analysing the effect of alkyl side chain length. For this purpose, tests were carried out on coating molecules that tend towards the homologous series of alkanes in terms of their alkyl side chain. The test again focuses on alkylalkoxysilanes and alkyldimethylchlorosilanes.

The first tests in relation to producing a successful coating will be carried out on the basis of silicon/glass planar substrates. On the basis of these samples, the homogeneity and hydrophobicity of the coating will then be characterised by means of static contact angle measurements. Using this data, a selection of coating molecules will be determined to be used subsequently for a provocation test.

2.5.1 Coating Silicon and Glass Planar Substrates

The substrates are coated according to the procedure known for alkylalkoxysilanes and alkylchlorosilanes from section 1.1. Table 20 provides an overview of the coating reagents tested.

TABLE 20

List of the alternative coating reagents tested

| Coating reagent | Abbreviation | Description |
|---|---|---|
| Methyltrimethoxysilane | C1 | Homologous series |
| Ethyltrimethoxysilane | C2 | |
| n-butyltrimethoxysilane | C4 | |
| n-octyltriethoxysilane | C8 | |
| n-decyltriethoxysilane | C10 | |
| n-dodecyltriethoxysilane | C12 | |
| Trimethylchlorosilane | C1-Cl | Homologous series |
| Ethyldimethylchlorosilane | C2-Cl | |
| n-butyldimethylchlorosilane | C4-Cl | |
| n-octyldimethylchlorosilane | C8-Cl | |
| 1H,1H,2H,2H-perfluorodecyldimethylchlorosilane | F13C8-Cl | Perfluorinated |

2.5.1.1 Screening the Coating Reagents Using Static Contact Angle Measurement

Table 21 shows the results of the static contact angle measurements for silicon and glass planar substrates.

TABLE 21

Averages together with standard deviation for water contact angle for additional coating reagents

| | Glass | | Silicon | |
|---|---|---|---|---|
| Coating reagent | Average [°] | Standard deviation [°] | Average [°] | Standard deviation [°] |
| Methyltrimethoxysilane | 85.14 | 1.97 | 85.85 | 1.98 |
| Ethyltrimethoxysilane | 88.38 | 2.08 | 88.29 | 1.80 |
| n-butyltrimethoxysilane | 88.05 | 2.13 | 87.83 | 0.99 |
| n-octyltriethoxysilane | 108.35 | 1.39 | 103.38 | 1.15 |
| n-decyltriethoxysilane | 108.15 | 2.17 | 108.96 | 2.09 |
| n-dodecyltriethoxysilane | 108.19 | 1.89 | 104.45 | 2.88 |
| Trimethylchlorosilane | 91.51 | 4.77 | 86.20 | 6.55 |
| Ethyldimethylchlorosilane | 88.45 | 2.05 | 76.67 | 1.95 |
| n-butyldimethylchlorosilane | 90.46 | 2.20 | 81.38 | 0.88 |
| n-octyldimethylchlorosilane | 100.99 | 1.76 | 88.87 | 6.30 |
| 1H,1H,2H,2H-perfluorodecyldimethylchlorosilane | 115.36 | 2.703 | 110.47 | 1.158 |
| 1H,1H,2H,2H-tridecafluoro-octyltriethoxysilane (reference) | 110.47 | 2.20 | 105.40 | 2.88 |

Whereas for alkyltrialkoxysilanes an increase in the contact angle is recorded as the length of the alkyl chain increases, this observation cannot be made for alkylmonochlorosilanes, in which a non-uniform development was observed in the water contact angles in relation to chain length.

In almost all the reagents, the contact angle on glass was always slightly higher than on silicon, i.e. for glass surfaces, there was a higher density of binding sites on the surface than for silicon surfaces. The largest contact angle was reached by the perfluorinated coating reagent F13C8-Cl. All the silicon/glass planar substrates tested showed stable contact angles with moderate standard deviation. No substrate showed layer detachment.

For the provocation test carried out afterwards using atomiser devices, the following selection was made on the basis of the coating reagents tested here:
methyltrimethoxysilane (C1)
n-octyltriethoxysilane (C8)
n-decyltriethoxysilane (C10)
n-dodecyltriethoxysilane (C12)
trimethylchlorosilane (C1-Cl)
n-octyldimethylchlorosilane (C8-Cl)
1H,1H,2H,2H-perfluorooctyldimethylchlorosilane (F13C8-Cl)

The selection makes it possible study the effect of the alkyl side chain and the effect of the coating chemistry. In addition, the selection includes coating reagents having very high and very low contact angles. Furthermore, this selection makes it possible check whether the contact angle is actually a suitable parameter for assessing whether a reagent is suitable for coating the DJI nozzles in question in order to prevent the phenomena of spray anomalies or jet divergency.

The results of the contact angle study showed that the coating was fundamentally detectable on all the substrates. All the coating reagents provided stable contact angles above 80°, and with a very moderate spread. However, the results also showed that there were significant differences in the resultant water contact angle.

In general, tightly packed, methyl-terminated monolayers have water contact angles of more than 110°. The contact angle becomes smaller as the molecules are packed less densely in the monolayer. This effect is presumably demonstrated in this case too in the small-chain alkyl chains C1, C2 and C2, and is thus representative of both the alkyltriethoxysilanes and alkyldimethylmonochlorosilanes. Overall, the reagents displayed water contact angles of less than 100° on both silicon and glass substrates.

It was found that the water contact angle increases as the chain length increases. This effect can be noted in both glass and silicon for the two reagent classes tested. In relation to the materials used here, C10 and C12 also showed the highest contact angles; this is most likely due to the higher packing density of the resultant layer. Sieval et al. disclosed that the maximum load of Si (111) is generally only around 0.5-0.55 of the molecular modelling simulation (cf. Sieval, A. B., et al., *Molecular modeling of covalently attached alkyl monolayers on the hydrogen-terminated Si (111) surface*. Langmuir, 2001. 17(7): pp. 2172-2181).

2.5.2 Performance of Additional Coating Reagents in a Provocation Test

As already known, the basic method for a provocation test can be taken from section 1.3.

The provocation test is set up as follows:
Formulation: as in 1.3.3
Coating:
Alkyltrialkoxysilanes:
methyltrimethoxysilane (C1),
n-octyltriethoxysilane (C8),
n-decyltriethoxysilane (C10),
n-dodecyltriethoxysilane (C12)
1H,1H,2H,2H-tridecafluorooctyltriethoxysilane (F13-C8)
Alkyldimethylchlorosilanes:
trimethylchlorosilane (C1-Cl),
n-octyldimethylchlorosilane (C8-Cl), 1H,1H,2H,2H-perfluorooctyldimethylchlorosilane (F1308-Cl),
1H,1H,2H,2H-perfluorodecyldimethylchlorosilane (F17010-Cl)
Concentration: 0.03 mol/l in each case
Number of inhalers: 30 for each reagent and reference
In-use mode: 1×1 stroke/day
Test parameters: Spray pattern according to spray pattern catalogue
Test Duration:
Decyltriethoxysilane (C10) and n-dodecyltriethoxysilane (C12), 1H,1H,2H,2H-tridecafluorooctyltriethoxysilane (F13-C8): 120 days, all other reagents 28 days 2.5.2.1 Group I Spray Pattern Curve FIG. 17 shows the group I ("good sprays") spray curves for the coated nozzles and the uncoated reference.

The figure shows that the long-chain alkylalkoxysilanes ensured a high number of group I sprays ("good sprays") for a long period of time, whereas all the other coating reagents showed no advantage over the uncoated reference. Within the alkylalkoxysilanes tested here, C12 (n-dodecyltriethoxysilane) showed the best results. In this test, it even had a slight advantage over the perfluorinated F1308 (1H,1H,2H,2H-tridecafluorooctyltriethoxysilane). The alkyl monochlorosilanes also performed relatively poorly again in this test. The test result from section 2.2.3 is thus confirmed and can even be extended to cover fluorinated compounds. In this test too, there was no advantage over the uncoated reference.

This therefore shows that the best spray performance is ensured by coatings having an alkyltrialkoxysilane (both fluorinated and non-fluorinated) having a long side chain (i.e. in this case by $C_{10}$ and $C_{12}$ chain lengths tested here).

2.5.2.2 Group II Spray Pattern Curve

FIG. 18 shows the group II spray curves (spray pattern anomalies) for the coated nozzles and the uncoated reference.

FIG. 18 very clearly shows that the long-chain alkylalkoxysilanes produced significantly fewer group II sprays than the chlorosilanes or short-chain alkylalkoxysilanes. It can also be seen here that both the short-chain alkoxysilanes and all the chlorosilanes barely brought any benefit compared with the uncoated reference. The long-chain alkylalkoxysilanes had a clear advantage over all the other reagents tested.

2.5.2.3 Group III Spray Pattern Curve

FIG. 19 shows the group III spray ("jet divergency") curves for the coated nozzles and the uncoated reference.

Examining the group III spray curve also confirms the idea gained from the previous spray pattern curves. The long-chain alkylalkoxysilanes did not once pass the 20% mark over 120 days of in-use time, whereas all the other reagents tested already exceeded this level after around 20 days.

2.5.2.4 Group III Sprays: 10-Day Average Rate Towards the End of the Test

The advantage that alkylalkoxysilanes have over the alkylmonochlorosilanes is particularly evident again when examining the 10-day average rate of the group III sprays, as shown in FIG. 20.

FIG. 20 shows the 10-day average rate of group III sprays for the alternative coating reagents after day 28. In this case, the uncoated reference reached a rate of around 40% group III sprays. The coatings using C1 (methyltrimethoxysilane), F1308-Cl (1H,1H,2H,2H-perfluorooctyldimethylchlorosilane) and F17010-Cl (1H,1H,2H,2H-perfluorodecyldimethylchlorosilane) are similarly poor. They show no advantage in terms of their coating. The aforementioned coating reagents F1308 (1H,1H,2H,2H-tridecafluorooctyltriethoxysilane), C10 (n-decyltriethoxysilane) and C12 (n-dodecyltriethoxysilane) achieve very good performance. For the cartridge period shown here (28-day mode), F1308 (1H,1H,2H,2H-tridecafluorooctyltriethoxysilane) and C12 (n-dodecyltriethoxysilane) was able to largely prevent the occurrence of group III sprays.

The results show very good performance for the alkyltrialkoxysilane group. The relatively poor performance of alkyl monochlorosilanes is surprising, all the more so since stable contact angles were achieved in the study carried out previously. No member of the group of tested alkylchlorosilanes could reach a group III spray rate of less than 10%. This is in contrast to the alkyltrialkoxysilanes, three members of which achieved a value of 5% for the 10-day average group III spray rate.

2.5.2.5 Results of the Provocation Test

As the results of the provocation test show, the alkyldimethylmonochlorosilanes performed relatively poorly, similarly to in section 2.2.3. For the alkyldimethylmonochlorosilanes, the 10-day average group III spray rate was much higher than the longer-chain alkyltrialkoxysilanes. Surprisingly, in this test methyltrimethoxysilane also showed similar performance to the alkyldimethylmonochlorosilanes.

The reasons for the poor performance of methyltrimethoxysilane are unclear. However, the spray pattern curve showed that the progression was very similar to the range of the uncoated reference over the entire duration of the test.

One possible explanation for the poor result for methyltrimethoxysilane could be an absent or insufficiently stable coating, or inadequate packing density.

The alkylmonochlorosilanes had a similar curve to the uncoated reference, although some members of the group did indeed show a slight layer effect. Looking at the 10-day average rate for group III sprays, a slight effect can be identified for trimethylchlorosilane (C1-Cl) or n-octyldimethylmonochlorosilane (C8-Cl).

The alkyltrialkoxysilanes have two sites more than the alkylmonochlorosilanes for coordinating with the surface. Therefore, they are bound to the surface much more strongly than the alkyldimethylmonochlorosilanes. This would explain the systematic difference between the alkylmonochlorosilanes and the alkyltrialkoxysilanes. However, this possible explanation does not apply to the poor performance of methyltrialkoxysilane since this reagent also has three sites for coordinating with the surface. Layer erosion or the aforementioned effect of the alkyl chain length on the packing density are assumed here too.

The provocation tests showed that n-decyltriethoxysilane (C10) and n-dodecyltriethoxysilane (C12) were well suited as coating reagents. They display similarly good results in their spray pattern curves as 1H,1H,2H,2H-tridecafluorooctyltriethoxysilane (F1308). Examining the 10-day average rate, it can be seen that n-dodecyltriethoxysilane (C12) was even slightly better. These results show that non-fluorinated alkylsilanes are a serious alternative to fluorinated silanes. This is surprising but fluoroalkylsilanes generally do produce the better anti-adhesion effect (cf. Giessler, S., E. Just, and R. Stôrger, *Easy-to-clean properties—Just a temporary appearance*, Thin Solid Films, 2006. 502(1): pp. 252-256). However, the data from the provocation test shows that a long alkyl chain length in the range of 010 and C12 was sufficient.

The data collected here also leads to the conclusion that a higher water contact angle alone is not necessarily an indicator of an effective coating reagent. In the previous study, the perfluorinated chlorosilane F17010-Cl had showed excellent contact angles of around 110° but performed very badly in the subsequent provocation test. Therefore, it is not possible to use the contact angle alone to deduce the spray performance in the provocation test, since the stability of the coating and its packing density also have to be considered. However, a high contact angle as defined by Ishizaki et al. can indicate a high packing density.

2.5.2.6 Yield of Category I Nozzles from Coating with Alternative Coating Reagents FIG. 21 shows the results of the microscopic analysis of the coated nozzle bodies in accordance with the nozzle body categorisation catalogue.

It can be seen in FIG. 21 that the coating reagent F1308 (1H,1H,2H,2H-tridecafluorooctyltriethoxysilane) generates the cleanest nozzles under the laboratory conditions tested. More than 90% of the nozzles tested here were classed as category I. The yield of category I nozzles is only around 25% for C12 (n-dodecyltriethoxysilane), which actually performed better than Dynasylan® F8261 in the provocation test. C10 (n-decyltriethoxysilane) also achieves a very good category I nozzle yield of around 55%.

1H,1H,2H,2H-tridecafluorooctyltriethoxysilane generates the most clean category I nozzles by far. In this test, the yield was surprisingly high at 90% and was achieved by additionally separating the nozzles at the drying phase before tempering.

In principle, the yield of clean nozzles could be increased further by using additional automated process steps. This could be done, for example, by using an aforementioned spin rinse dryer, which expels residual solution from the nozzle by means of rotation. Alternatively or additionally, rinsing processes, e.g. using alcoholic solvents, can be carried out. This should further increase the yield of clean nozzles since much less residual solution is present in the nozzle bodies when they are dried further.

2.5.2.7 Overall Results in Terms of Additional Coating Reagents

In conclusion, it is evident that the best results are achieved using a long-chain alkylalkoxysilane. In this test, good alternatives to the fluorinated compounds were found, namely n-decyltriethoxysilane (C10) and n-dodecyltriethoxysilane (C12).

LIST OF REFERENCE NUMERALS

| | |
|---|---|
| 1 | microstructured component |
| 2 | inlet opening |
| 3 | outlet opening |
| 4 | channels |
| 5 | fine filter |
| 6 | plenary chamber |
| 7 | column structure |
| 8 | coating |
| 9 | atomiser |
| 10 | liquid |
| 11 | aerosol |
| 12 | pressure chamber |
| 13 | upper housing part |
| 14 | inner housing part |
| 15 | lower housing part |
| 16 | container |
| 17 | mainspring |
| 18 | pressure generator |
| 19 | locking ring |
| 20 | button |
| 21 | tubular piston |
| 22 | return valve |

-continued

| | |
|---|---|
| 23 | mount |
| 24 | meter |
| 25 | filter system |

The invention claimed is:

1. A discharge apparatus for fluids comprising a microstructured component comprising a surface modification obtained by contacting the surface of the microstructured component with a modification reagent, thereby modifying the properties of the surface by the chemical and/or physical interaction between the microstructured component surface and the modification reagent;

wherein the modification reagent comprises at least one modifier, wherein the modifier is a silane of the general formula (III):

$$R_{4-n}SiX_n$$

wherein

R is $C_{10}$-$C_{16}$ alkyl,

X is selected from $C_1$ alkoxy and $C_2$ alkoxy, and n is 3; and wherein the at least one modifier is at a concentration of from 0.001 to 2 mol/L based on the modification reagent.

2. The discharge apparatus according to claim 1, comprising at least one liquid medicinal product.

3. The discharge apparatus according to claim 2, wherein the liquid medicinal product is a dispersion or solution of at least one pharmaceutical active ingredient.

4. A microstructured component for use in a microfluidic system, comprising an outer surface, at least one inlet opening, at least one outlet opening, and inner surfaces formed by microstructures, wherein the inner surfaces are modified, at least in part, with a silane modifier of general formula (III):

$$R_{4-n}SiX_n$$

wherein

R is $C_{10}$-$C_{16}$ alkyl,

X is selected from $C_1$ alkoxy and $C_2$ alkoxy, and n is 3.

5. The microstructured component according to claim 4, wherein the outer surface of the component is modified.

6. The microstructured component according to claim 4, wherein the inner surface of the component is modified to be rendered hydrophobic.

7. A microstructured component according to claim 4, wherein the silane is selected from the group consisting of $C_{12}$ alkyltrialkoxysilanes, $C_{14}$ alkyltrialkoxysilanes and $C_{16}$ alkyltrialkoxysilanes, and mixtures thereof.

8. The microstructured component according to claim 4, wherein the inner surface of the microstructured component is activated before modification.

9. The microstructured component according to claim 4, wherein the microstructured component comprises two outlet openings and the microstructured component has channels which connect the outlet openings directly or indirectly with the at least one inlet opening.

10. The microstructured component according to claim 9, wherein the channels of the outlet openings are oriented towards one another at an angle of from 50° to 130°.

11. The microstructured component according to claim 4, wherein the microstructured component further comprises a filter region between the inlet opening and the outlet opening.

12. The microstructured component according to claim 4, wherein the component consists of two different materials.

13. The microstructured component according to claim 12, wherein the component consists of glass and silicon wherein the inner surfaces of the component are modified, at least in part, with a silane modifier of general formula (III).

14. The microstructured component according to claim 12, wherein at least one of the materials is microstructured on a side on which the material is bonded to a second material and thus there is a microstructure located within the component as a result of the bonding between the different materials.

* * * * *